United States Patent
Ran et al.

(10) Patent No.: US 12,048,245 B2
(45) Date of Patent: Jul. 23, 2024

(54) COMPOUND, ORGANIC LIGHT-EMITTING ELEMENT INCLUDING THE SAME, DISPLAY PANEL AND DISPLAY DEVICE

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Quan Ran, Shanghai (CN); Wei Gao, Shanghai (CN); Jinghua Niu, Shanghai (CN); Lei Zhang, Shanghai (CN); Wenpeng Dai, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 774 days.

(21) Appl. No.: 17/011,997

(22) Filed: Sep. 3, 2020

(65) Prior Publication Data
US 2020/0403161 A1 Dec. 24, 2020

(30) Foreign Application Priority Data
Jun. 16, 2020 (CN) .......................... 202010547222.0

(51) Int. Cl.
*H10K 85/60* (2023.01)
*C07D 493/10* (2006.01)
(Continued)

(52) U.S. Cl.
CPC ......... *H10K 85/657* (2023.02); *C07D 493/10* (2013.01); *C07D 493/22* (2013.01);
(Continued)

(58) Field of Classification Search
CPC .. H10K 85/657; H10K 85/636; H10K 85/626; H10K 85/40; H10K 85/6574;
(Continued)

(56) References Cited

FOREIGN PATENT DOCUMENTS

| CN | 1157461 C | 7/2004 |
|---|---|---|
| CN | 107709297 A | 2/2018 |

*Primary Examiner* — Shane Fang
(74) *Attorney, Agent, or Firm* — KILPATRICK TOWNSEND & STOCKTON LLP

(57) ABSTRACT

Provided are a compound, an organic light-emitting element including the same, a display panel and a display device. The compound has a structure represented by Formula I. The organic light-emitting element includes an anode, a cathode and an organic thin film layer disposed between the anode and the cathode; where the organic thin film layer includes a light-emitting layer, and further includes any one or a combination of at least two of a hole transport layer, an electron blocking layer and an auxiliary light-emitting layer, and at least one of the hole transport layer, the electron blocking layer and the auxiliary light-emitting layer contains at least one of the compounds. The compound has a relatively shallow HOMO energy level, a relatively shallow LUMO energy level, a relatively high triplet energy level, an appropriate hole mobility, a relatively high $T_g$, a large molecular torque and good thermal stability.

9 Claims, 2 Drawing Sheets

(51) Int. Cl.

| | |
|---|---|
| *C07D 493/22* | (2006.01) |
| *C07D 495/10* | (2006.01) |
| *C07D 495/22* | (2006.01) |
| *C07D 519/00* | (2006.01) |
| *C07F 7/08* | (2006.01) |
| *C09K 11/06* | (2006.01) |
| *H10K 50/11* | (2023.01) |
| *H10K 50/15* | (2023.01) |
| *H10K 50/16* | (2023.01) |
| *H10K 50/17* | (2023.01) |
| *H10K 50/18* | (2023.01) |
| *H10K 85/40* | (2023.01) |

(52) U.S. Cl.
CPC ......... *C07D 495/10* (2013.01); *C07D 495/22* (2013.01); *C07D 519/00* (2013.01); *C07F 7/0816* (2013.01); *C09K 11/06* (2013.01); *H10K 85/40* (2023.02); *H10K 85/626* (2023.02); *H10K 85/636* (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 85/6574* (2023.02); *H10K 85/6576* (2023.02)

(58) Field of Classification Search
CPC ........ H10K 50/17; H10K 50/15; H10K 50/16; H10K 50/18; H10K 50/11; H10K 50/171; H10K 85/6576; C07D 493/10; C07D 493/22; C07D 495/10; C07D 495/22; C07D 519/00; C07F 7/0816; C09K 11/06; C09K 2211/1018; H01L 51/006; H01L 51/0059; H01L 51/5056; H01L 51/0052; H01L 51/0058; H01L 51/0012; C07C 211/54; C07C 211/58

See application file for complete search history.

COMPOUND, ORGANIC LIGHT-EMITTING ELEMENT INCLUDING THE SAME, DISPLAY PANEL AND DISPLAY DEVICE

CROSS-REFERENCE TO RELATED APPLICATION(S)

The application claims the benefit of the earlier filing date of Chinese Patent Application No. 202010547222.0, filed on Jun. 16, 2020 to the China National Intellectual Property Administration, the contents of which are incorporated by reference herein in its entirety.

FIELD

The present disclosure belongs to the field of organic optoelectronic materials and, in particular, relates to a compound, an organic light-emitting element including the same, a display panel and a display device.

BACKGROUND

Organic light-emitting elements (such as OLED elements) are light-emitting elements based on organic light-emitting materials and have attracted wide attention due to the advantages of efficient light-emitting, simple manufacturing processes and a large area of flexibility. At present, the OLED elements have substantially met the requirements of small and medium-sized displays and are widely applied in the fields of flat panel display and lighting such as instruments and meters, high-end smart phones and televisions.

In addition to the necessary light-emitting layer, an OLED element generally includes one or more functional layers selected from a hole injection layer, a hole transport layer, an electron blocking layer, a hole blocking layer, an electron transport layer, an electron injection layer, etc., which are used for adjusting the injection and transport of electrons and holes. Many small and medium-sized OLED displays of mobile phones and other consumer products adopt an RGB sub-pixel display method. To improve a production yield, some functional layers tend to be designed as common layers, so that fewer fine metal masks (FFMs) can be used. The hole transport layer tends to adopt the common layer, and generally the common hole transport layer may be prepared by using commercially available materials.

An existing hole transport material has the following problems: first, the material has poor solubility, which will result in a poor cleaning effect of an evaporation mask during mass production; second, the material has extremely low mobility, which will result in a high overall voltage of the element; third, the material has extremely high mobility, especially extremely high lateral mobility, which will result in cross-talk between adjacent pixels; fourth, a LUMO energy level of the material is too deep to effectively block electrons that might migrate beyond the light-emitting layer; fifth, a triplet energy level of the material is too low to effectively block excitons in the light-emitting layer, resulting in low light-emitting efficiency of the element.

At present, some hole transport materials have been developed and applied, but part of the preceding problems exists more or less. For example, a commercially available hole transport layer material, a compound H1

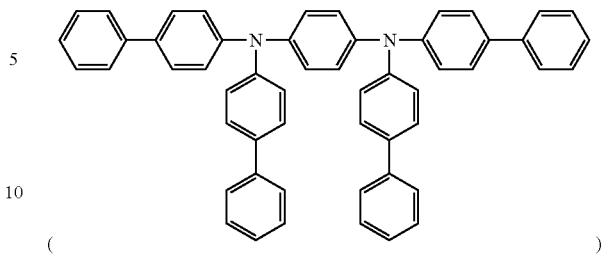

has a relatively high longitudinal mobility and a relatively low lateral mobility which are within an acceptable range, poor solubility, and a relatively low triplet energy level. A compound H2

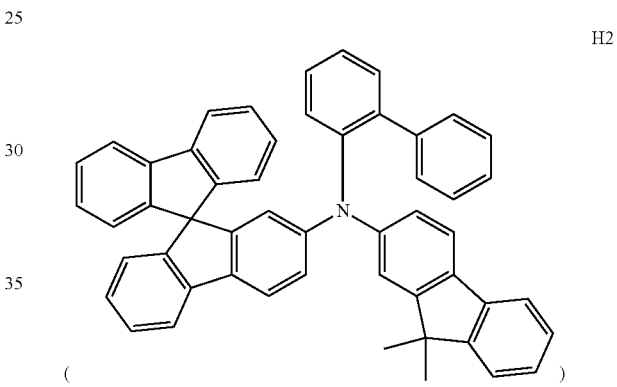

disclosed in CN 103108859A has good solubility and extremely high mobility, and the crosstalk between adjacent pixels might occur.

Current researches on the OLED elements are still in a development stage, and there are a few types of good hole transport materials. Therefore, hole transport materials with better performance are to be developed.

SUMMARY

In view of defects in the related art, the present disclosure aims to provide a compound, an organic light-emitting element including the same, a display panel and a display device. The compound has a relatively shallow HOMO energy level, a relatively shallow LUMO energy level, a relatively high triplet energy level, an appropriate hole mobility, a relatively high $T_g$, a large molecular torque and good thermal stability, is not easy to crystallize, and may be used in a hole transport layer, an electron blocking layer and/or an auxiliary light-emitting layer of an organic light-emitting element, to reduce a working voltage of the element and improve light-emitting efficiency and a lifetime of the element.

To achieve the object, the present disclosure adopts solutions below.

In a first aspect, the present disclosure provides a compound which has a structure represented by Formula I:

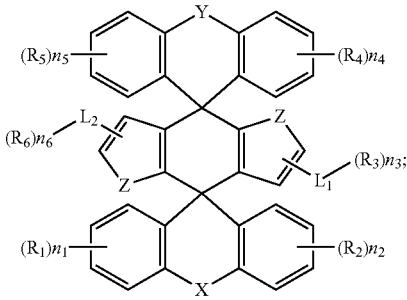

formula I where in Formula I, $R_1$ to $R_6$ are each independently selected from any one of a deuterium atom, substituted or unsubstituted C1 to C20 alkyl, substituted or unsubstituted C1 to C20 alkoxy, substituted or unsubstituted C1 to C20 alkylthio, substituted or unsubstituted C3 to C20 cycloalkyl, substituted or unsubstituted C3 to C20 heterocycloalkyl, substituted or unsubstituted C6 to C40 aryl or substituted or unsubstituted C3 to C30 heteroaryl;

$n_1$ to $n_6$ are each independently an integer from 0 to 4, and $n_3$ and $n_6$ are not 0 at the same time;

$L_1$ and $L_2$ are each independently selected from any one of a single bond or substituted or unsubstituted C6 to C30 arylene;

X and Y are each independently selected from any one of a single bond, an O atom, a S atom,

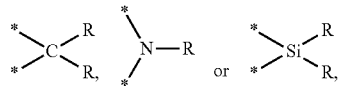

where * represents a position where groups are joined, and R is selected from any one of substituted or unsubstituted C6 to C30 aryl, substituted or unsubstituted C1 to C10 alkyl, substituted or unsubstituted C1 to C10 alkoxy or substituted or unsubstituted C1 to C10 alkylthio;

Z is an oxygen atom or a sulfur atom; and when a substituent is contained in the above groups, the substituent is selected from any one of cyano, a halogen atom, hydroxyl, nitro, C1 to C10 alkyl, C1 to C10 alkoxy, C1 to C10 alkylthio, C3 to C12 cycloalkyl, C6 to C18 aryl or C2 to C18 heteroaryl.

In a second aspect, the present disclosure provides an organic light-emitting element, including an anode, a cathode and an organic thin film layer disposed between the anode and the cathode; where the organic thin film layer includes a light-emitting layer, and further includes any one or a combination of at least two of a hole transport layer, an electron blocking layer and an auxiliary light-emitting layer.

At least one of the hole transport layer, the electron blocking layer and the auxiliary light-emitting layer contains at least one of the compounds described in the first aspect.

In a third aspect, the present disclosure provides a display panel including the organic light-emitting element described in the second aspect.

In a fourth aspect, the present disclosure provides a display device including the display panel described in the third aspect.

Compared with the related art, the present disclosure has beneficial effects below.

The compound provided by the present disclosure has a relatively shallow HOMO energy level, a relatively shallow LUMO energy level, a relatively high triplet energy level, an appropriate hole mobility, a relatively high $T_g$, a large molecular torque and good thermal stability, is not easy to crystallize, and may be used in the hole transport layer, the electron blocking layer and/or the auxiliary light-emitting layer of the organic light-emitting element, to reduce the working voltage of the element and improve the light-emitting efficiency and the lifetime of the element.

BRIEF DESCRIPTION OF DRAWINGS

To more clearly illustrate solutions in examples of the present disclosure or the related art, the drawings to be used in the description of the examples or the related art will be briefly described below.

Figure 1:
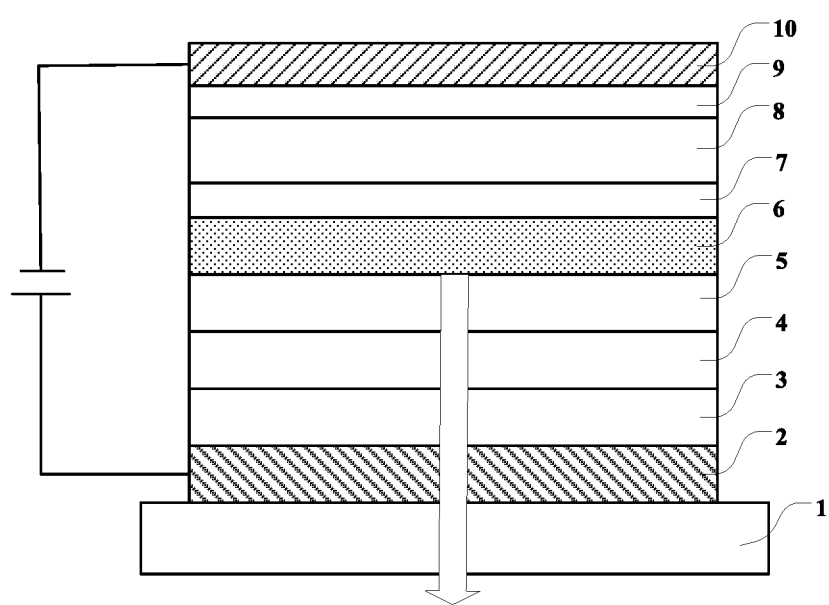
FIG. 1 is a structural diagram of an OLED element according to an application example of the present disclosure.

In the drawings: 1: substrate; 2: anode; 3: hole injection layer; 4: first hole transport layer; 5: second hole transport layer; 6: light-emitting layer; 7: hole blocking layer; 8: electron transport layer; 9: electron injection layer; 10: cathode; 11: display of a mobile phone

DETAILED DESCRIPTION

The solutions of the present disclosure will be further described below in conjunction with the drawings and examples. The examples described herein are used for a better understanding of the present disclosure and should not be construed as specific limitations to the present disclosure.

In a first aspect, the present disclosure provides a compound which has a structure represented by Formula I:

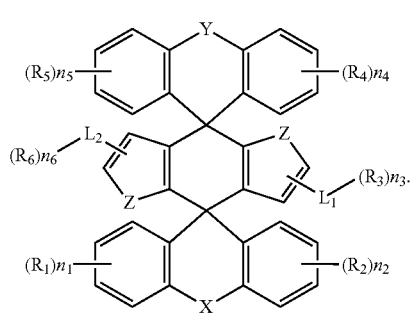

formula I

In Formula I, $R_1$ to $R_6$ are each independently selected from any one of a deuterium atom, substituted or unsubstituted C1 to C20 (which may be, for example, C1, C2, C3, C5, C8, C10, C12, C15, C18 or C20, etc.) alkyl, substituted or unsubstituted C1 to C20 (which may be, for example, C1, C2, C3, C5, C8, C10, C12, C15, C18 or C20, etc.) alkoxy, substituted or unsubstituted C1 to C20 (which may be, for example, C1, C2, C3, C5, C8, C10, C12, C15, C18 or C20, etc.) alkylthio, substituted or unsubstituted C3 to C20 (which may be, for example, C3, C5, C8, C10, C12, C15, C18 or C20, etc.) cycloalkyl, substituted or unsubstituted C3 to C20 (which may be, for example, C3, C5, C8, C10, C12, C15, C18 or C20, etc.) heterocycloalkyl, substituted or unsubstituted C6 to C40 (which may be, for example, C6, C8, C10, C12, C15, C18, C21, C24, C28, C30, C34, C36 or C40, etc.) aryl or substituted or unsubstituted C3 to C30 (which may be, for example, C3, C4, C5, C6, C8, C10, C12, C15, C18, C21, C24, C28 or C30, etc.) heteroaryl.

In Formula I, $n_1$ to $n_6$ are each independently an integer from 0 to 4 (which may be, for example, 0, 1, 2, 3 or 4), and $n_3$ and $n_6$ are not 0 at the same time.

In Formula I, $L_1$ and $L_2$ are each independently selected from any one of a single bond or substituted or unsubstituted C6 to C30 (which may be, for example, C6, C8, C10, C12, C15, C18, C21, C24, C28 or C30, etc.) arylene.

In Formula I, X and Y are each independently selected from any one of a single bond, an O atom, a S atom,

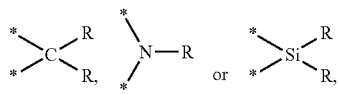

where * represents a position where groups are joined, and R is selected from any one of substituted or unsubstituted C6 to C30 (which may be, for example, C6, C8, C10, C12, C15, C18, C21, C24, C28 or C30, etc.) aryl, substituted or unsubstituted C1 to C10 (which may be, for example, C1, C2, C3, C5, C6, C8 or C10, etc.) alkyl, substituted or unsubstituted C1 to C10 (which may be, for example, C1, C2, C3, C5, C6, C8 or C10, etc.) alkoxy or substituted or unsubstituted C1 to C10 (which may be, for example, C1, C2, C3, C5, C6, C8 or C10, etc.) alkylthio.

In Formula I, Z is an oxygen atom or a sulfur atom.

When a substituent is contained in the above groups, the substituent is selected from any one of cyano, a halogen atom, hydroxyl, nitro, C1 to C10 (which may be, for example, C1, C2, C3, C5, C8 or C10, etc.) alkyl, C1 to C10 (which may be, for example, C1, C2, C3, C5, C8 or C10, etc.) alkoxy, C1 to C10 (which may be, for example, C1, C2, C3, C5, C8 or C10, etc.) alkylthio, C3 to C12 (which may be, for example, C3, C5, C6, C8, C10 or C12, etc.) cycloalkyl, C6 to C18 (which may be, for example, C6, C8, C10, C12, C15 or C18, etc.) aryl or C2 to C18 (which may be, for example, C2, C3, C4, C5, C6, C8, C10, C12, C15 or C18, etc.) heteroaryl; the substituent is preferably any one of C1 to C10 alkyl, C1 to C10 alkoxy, C1 to C10 alkylthio, C3 to C12 cycloalkyl, C6 to C18 aryl or C2 to C18 heteroaryl.

The compound provided by the present disclosure has a structure of double spiro-cycles, a center of which is joined to an electron-donating thiophene or furan ring, and at least one of $R_3$ and $R_6$ is an electron-donating group, so that the compound has a relatively strong electron-donating ability and a relatively shallow HOMO energy level, which reduces a hole injection barrier and helps the injection of holes; the compound has a relatively shallow LUMO energy level, which can effectively block electrons; the compound has a relatively high triplet energy level, which can effectively block excitons, confine the excitons in a light-emitting layer, and increase an utilization rate of the excitons, thereby improving efficiency of an organic light-emitting element using the compound.

In the compound provided by the present disclosure, the electron-donating group in $R_3$ and $R_6$ is conjugated with the thiophene ring or the furan ring, which facilitates the transport of holes, so that the compound has an appropriate hole mobility.

The compound provided by the present disclosure has a relatively high $T_g$ (glass transition temperature), and the plane where condensed rings

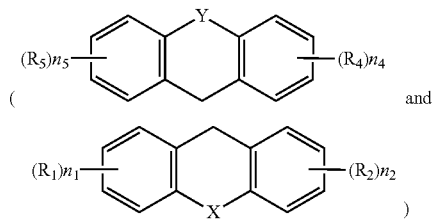

on two ends and a condensed ring

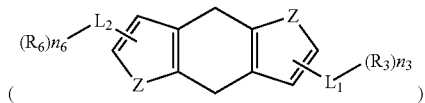

in center are located is distorted to a greater degree, which avoids molecular planarization and reduces the compound's crystallinity. In this way, the compound has relatively good thermal stability, thereby improving the stability of the organic light-emitting device using the compound; and the compound has good solubility and ease to be sublimated, and is convenient to be evaporated and deposited.

It is to be noted that the LUMO energy level and the HOMO energy level of the compound provided by the present disclosure have negative values, a "high" or "shallow" HOMO energy level or LUMO energy level in the present disclosure means a smaller absolute value relative to a certain HOMO or LUMO energy level, and a "low" or "deep" HOMO energy level or LUMO energy level means a larger absolute value relative to a certain HOMO or LUMO energy level.

In the present disclosure, $n_1$ to $n_6$ represent the number of groups $R_1$ to $R_6$, respectively, and a value of 0 means no substituents.

In an embodiment of the present disclosure, the compound has a structure represented by Formula II or Formula III:

formula II

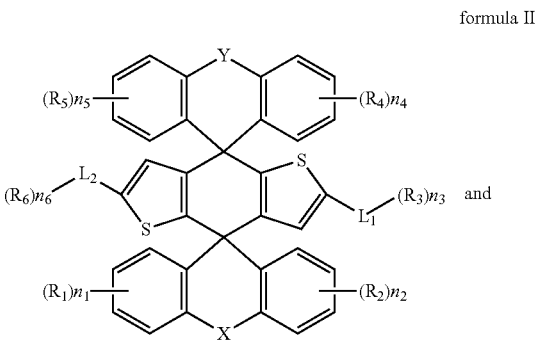

and formula III

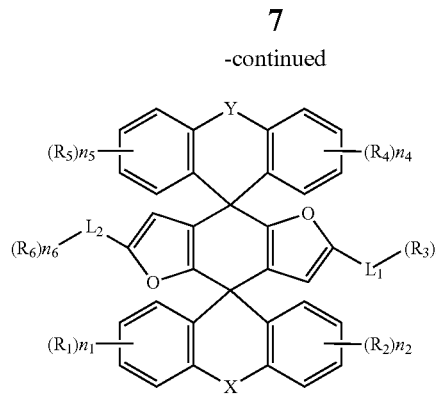

In an embodiment of the present disclosure, the compound has a structure represented by Formula IV or Formula V:

formula IV

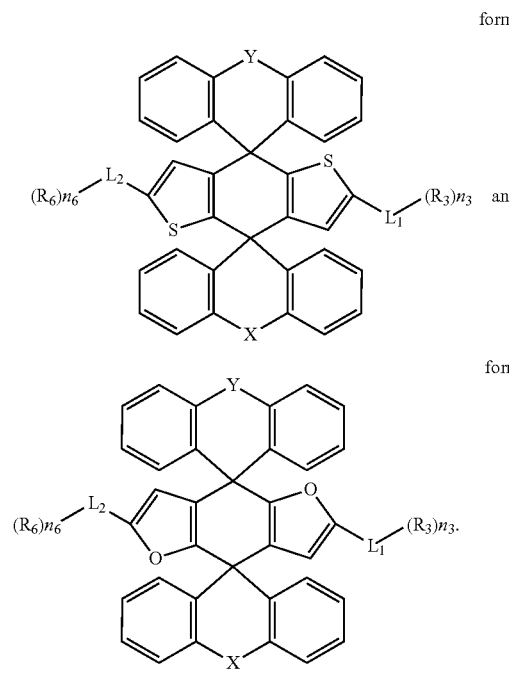
and formula V

In an embodiment of the present disclosure, the compound has a structure represented by Formula VI or Formula VII:

formula VI

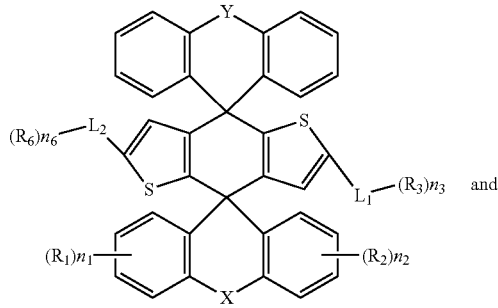
and formula VII

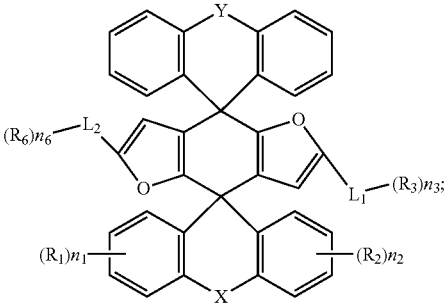

where $n_1$ and $n_2$ are each independently an integer from 1 to 4 (which may be, for example, 1, 2, 3 or 4).

In an embodiment of the present disclosure, $L_1$ and $L_2$ are each independently a single bond,

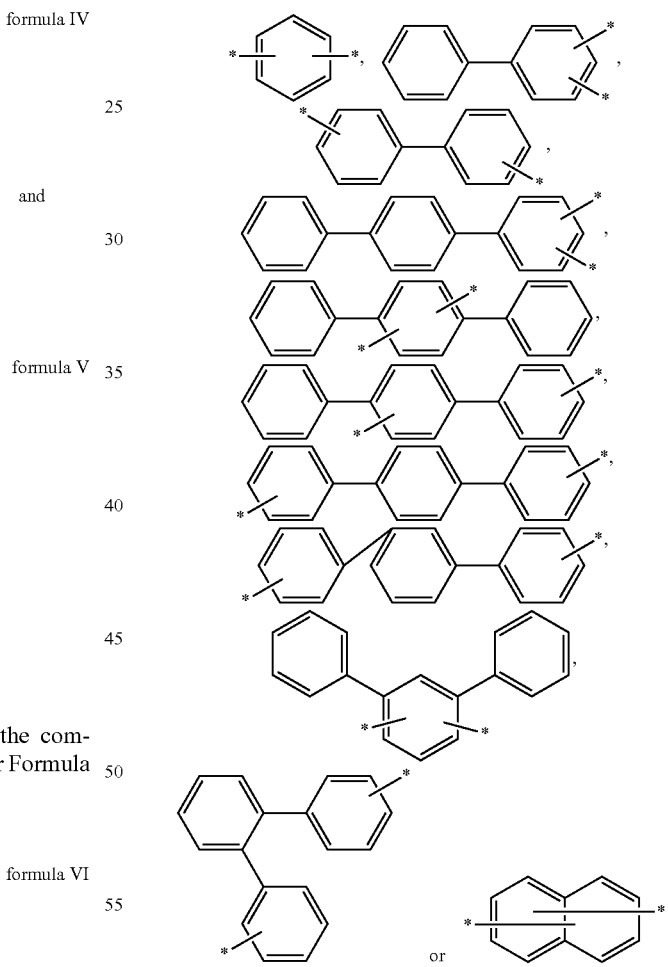

where * represents a position where groups are joined.

In an embodiment of the present disclosure, $R_3$ and $R_6$ are independent of each other, and at least one of $R_3$ and $R_6$ is selected from any one of substituted or unsubstituted C6 to C40 (which may be, for example, C6, C8, C10, C12, C15, C18, C21, C24, C28, C30, C34, C36 or C40, etc.) aryl, substituted or unsubstituted carbazolyl, substituted or unsubstituted arylamino, substituted or unsubstituted acridinyl, substituted or unsubstituted furyl, substituted or unsubstituted thienyl, substituted or unsubstituted benzofuryl, substituted or unsubstituted benzothicnyl, substituted or unsubstituted diphenylfuryl, substituted or unsubstituted diphenylthienyl, substituted or unsubstituted phenothiazinyl, substituted or unsubstituted phenoxazinyl, substituted or unsubstituted fluorenyl or substituted or unsubstituted spirofluorenyl.

When a substituent is contained in the above groups, the substituent is selected from any one of C1 to C10 alkyl, C1 to C10 alkoxy, C1 to C10 alkylthio, C3 to C12 cycloalkyl, C6 to C18 aryl or C2 to C18 heteroaryl.

In an embodiment of the present disclosure, $R_3$ and $R_6$ are independent of each other, and at least one of $R_3$ and $R_6$ is selected from any one of the following groups:

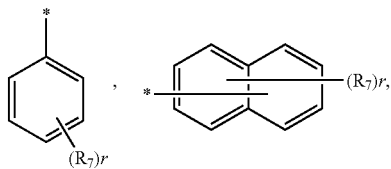

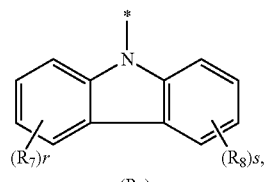

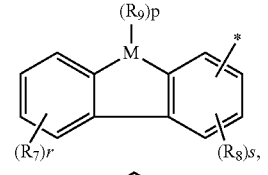

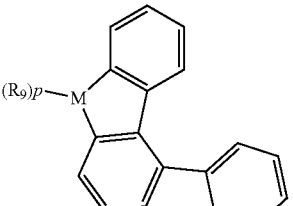

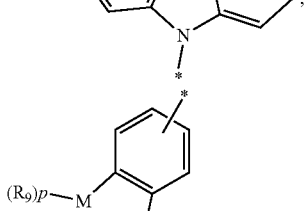

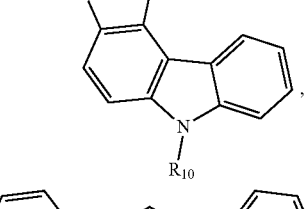

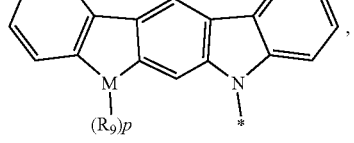

-continued

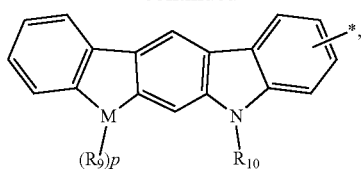

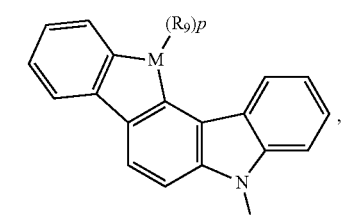

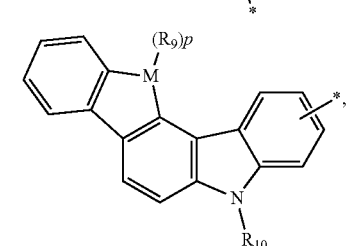

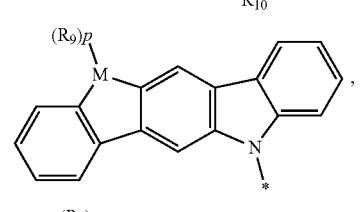

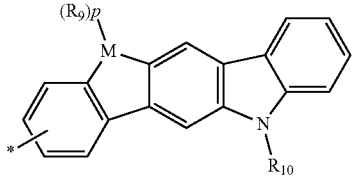

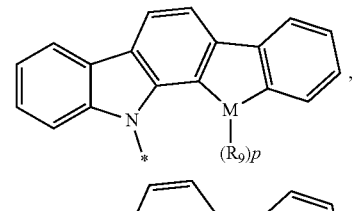

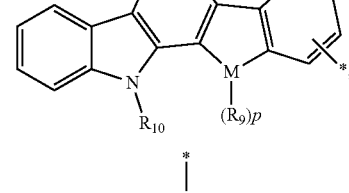

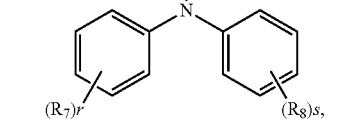

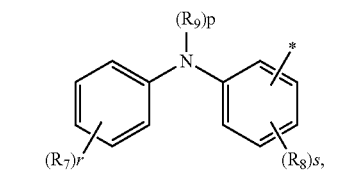

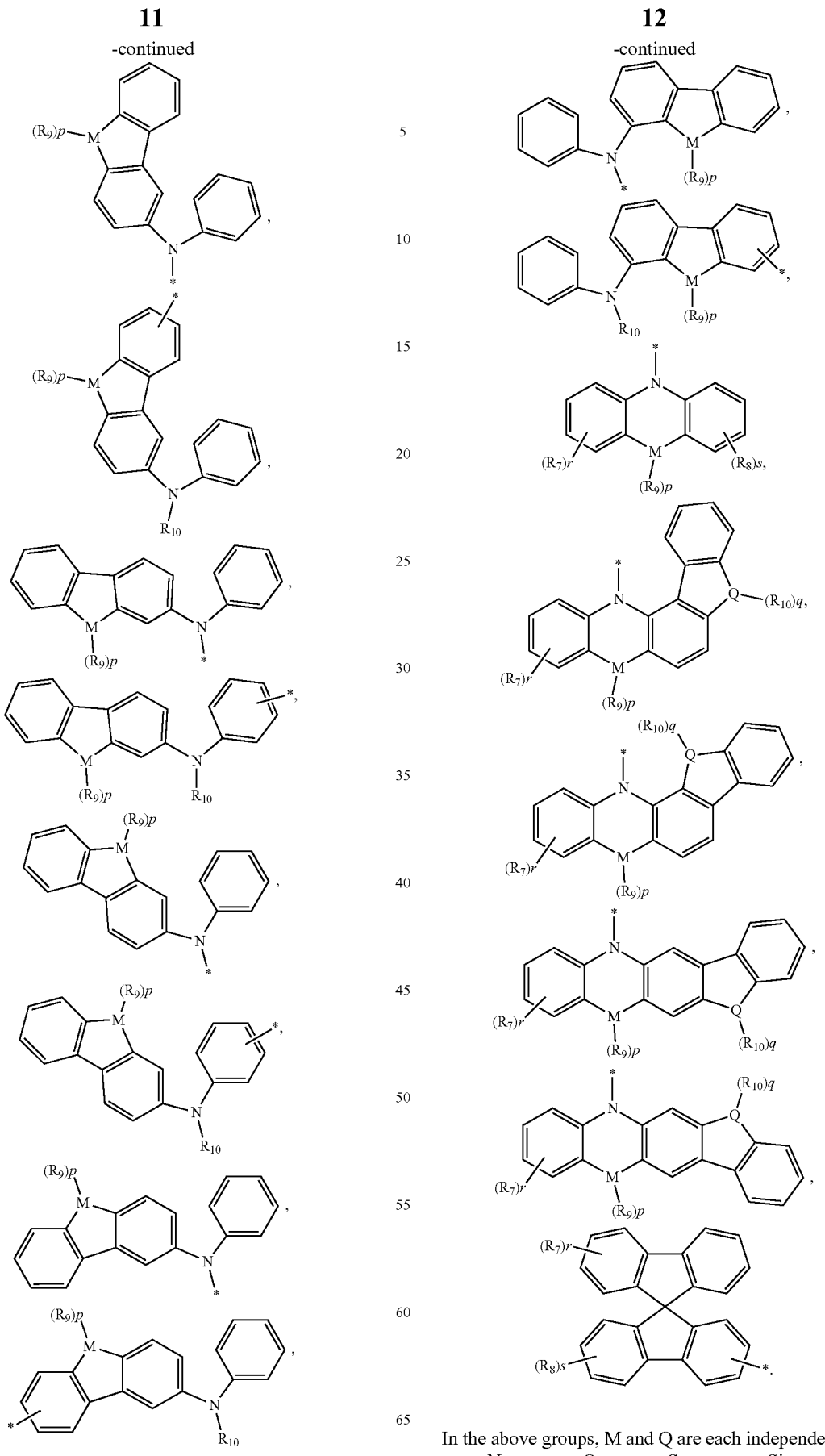
In the above groups, M and Q are each independently a C atom, a N atom, an O atom, a S atom or a Si atom.

In the above groups, $R_7$ and $R_8$ are each independently selected from any one of C1 to C20 alkyl, C1 to C20 alkoxy, C1 to C20 alkylthio or the following groups:

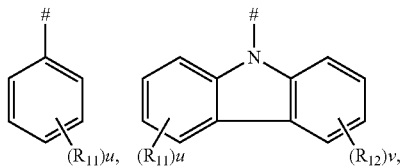

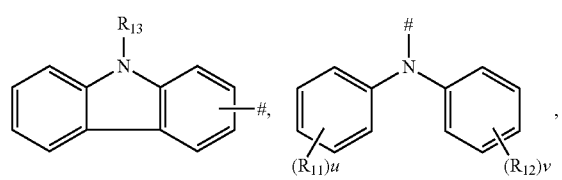

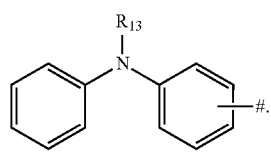

In the above groups, $R_7$ and $R_{10}$ are each independently selected from any one of a hydrogen atom, C1 to C20 alkyl, C1 to C20 alkoxy, C1 to C20 alkylthio or the following groups:

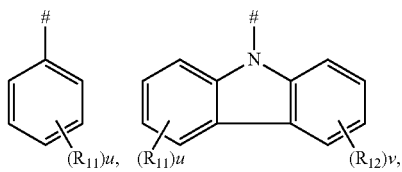

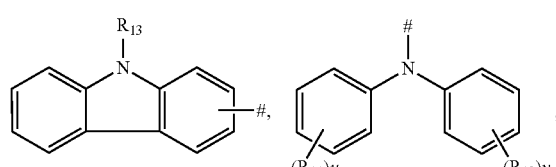

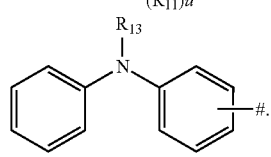

In the above groups, r, s, p and q are each independently 0, 1 or 2.

In the above groups, $R_{11}$, $R_{12}$ and $R_{13}$ are each independently selected from any one of C1 to C20 alkyl, C1 to C20 alkoxy, C1 to C20 alkylthio or phenyl.

In the above groups, u and v are each independently 0, 1 or 2.

In the above groups, * and # each represent a position where groups are joined.

It is to be noted that in the present disclosure, r, s, u and v represent the number of substituents $R_7$, $R_8$, Rn and $R_{12}$, respectively. A value of 0 means that there is no substituent and a corresponding position is occupied by a H atom to satisfy a chemical environment.

In the above groups, p and q respectively represent the number of monovalent substituents or atoms to be linked by M and Q atoms to satisfy the chemical environment. Apparently, when M and Q are O atoms or S atoms, p and q are 0; when M and Q are N atoms, p and q are 1; when M and Q are C atoms or Si atoms, p and q are 2.

In an embodiment of the present disclosure, $n_3$ is equal to no, and $R_3$ and $R_6$ are same groups.

In an embodiment of the present disclosure, $n_1$ and $n_2$ are each independently an integer from 1 to 4 (which may be, for example, 1, 2, 3 or 4), and $R_1$ and $R_2$ are each independently selected from any one of C1 to C5 alkyl, C1 to C5 alkoxy, C1 to C5 alkylthio or phenyl.

In an embodiment of the present disclosure, $n_1$ is equal to $n_2$, and $R_1$ and $R_2$ are same groups.

In an embodiment of the present disclosure, $n_4$ and $n_5$ are each independently an integer from 1 to 4, and $R_4$ and $R_8$ are each independently selected from any one of C1 to C5 alkyl, C1 to C5 alkoxy, C1 to C5 alkylthio or phenyl.

In an embodiment of the present disclosure, $n_4$ is equal to $n_5$, and $R_4$ and $R_8$ are same groups.

In an embodiment of the present disclosure, X is the same as Y.

In an embodiment of the present disclosure, X and Y are each a single bond, an O atom, a S atom or

In the present disclosure, compared with X and Y which are

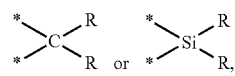

X and

Y which are O atoms, S atoms or

are advantageous for further improving the HOMO energy level of the compound; and when X and Y are single bonds, the compound has better stability.

In an embodiment of the present disclosure, the compound is selected from any one of the following compounds 1 to 488:

15
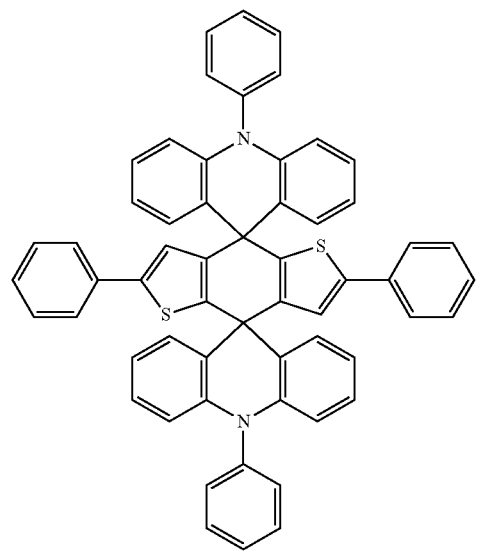
1
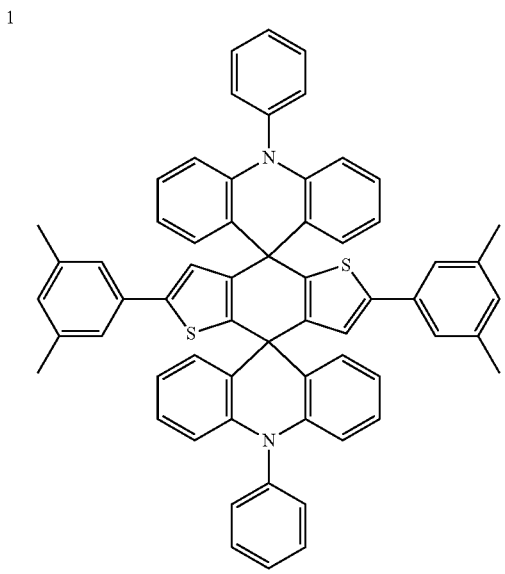
2
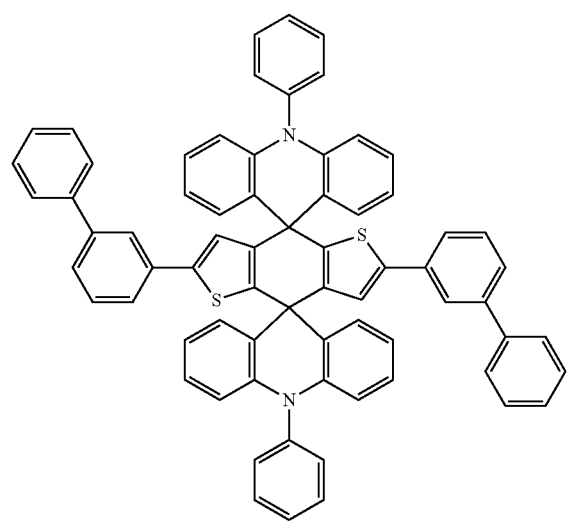
3
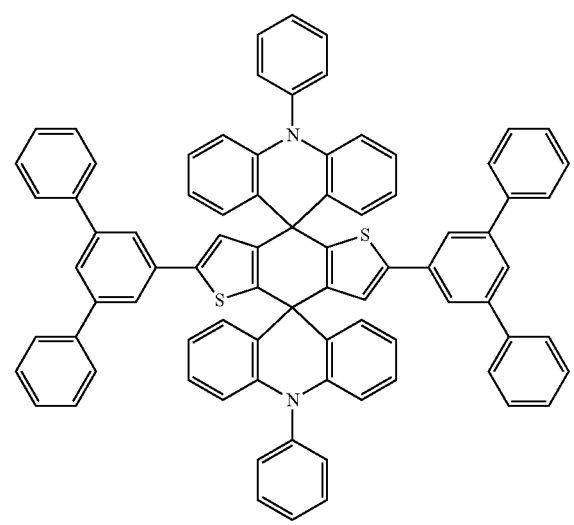
4
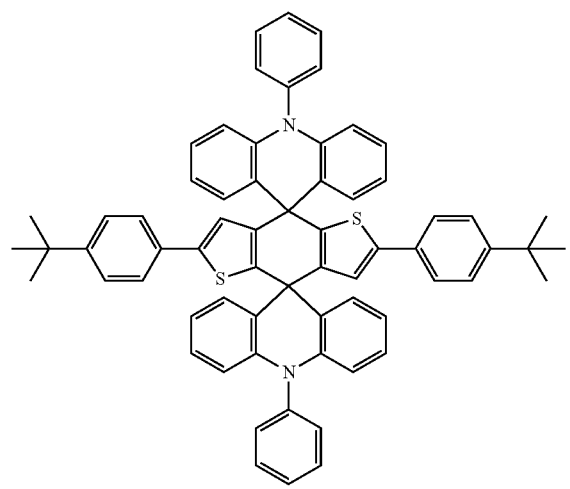
5
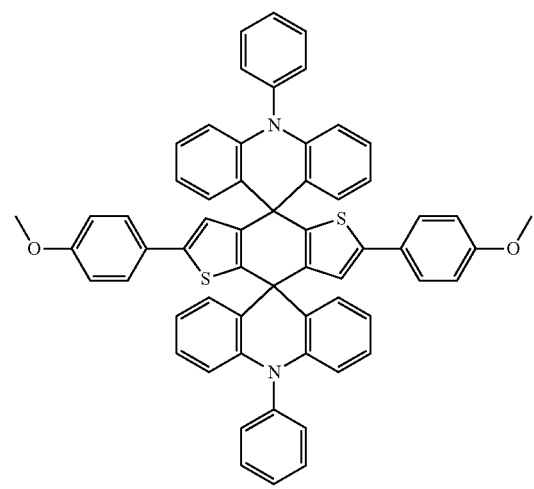
6

7
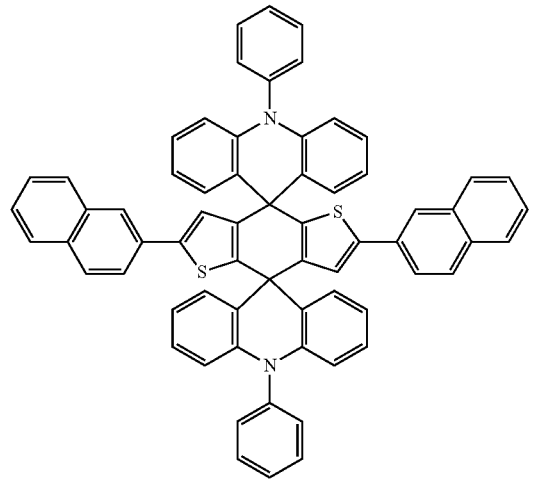
8
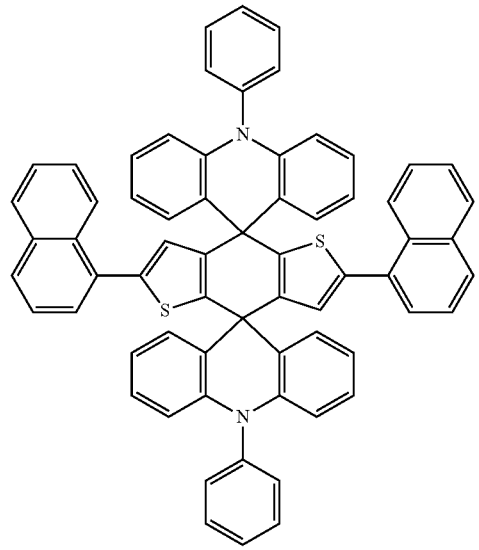
9
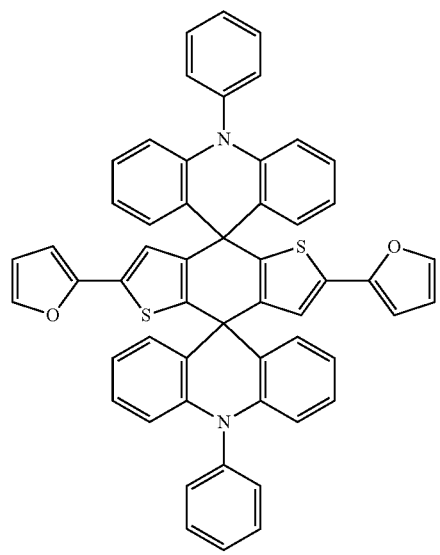
10
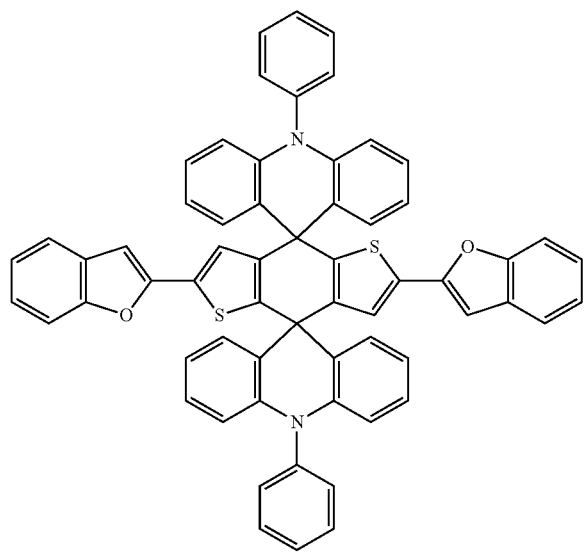

-continued
11
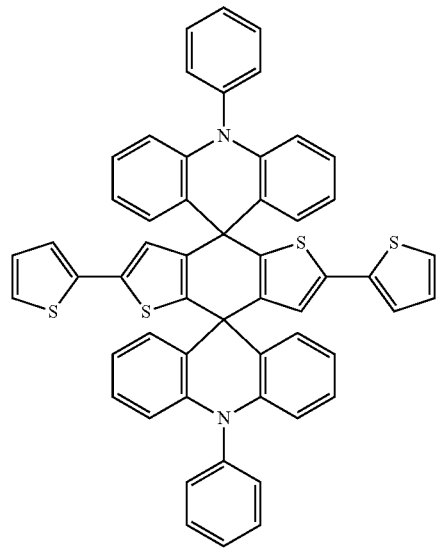
12
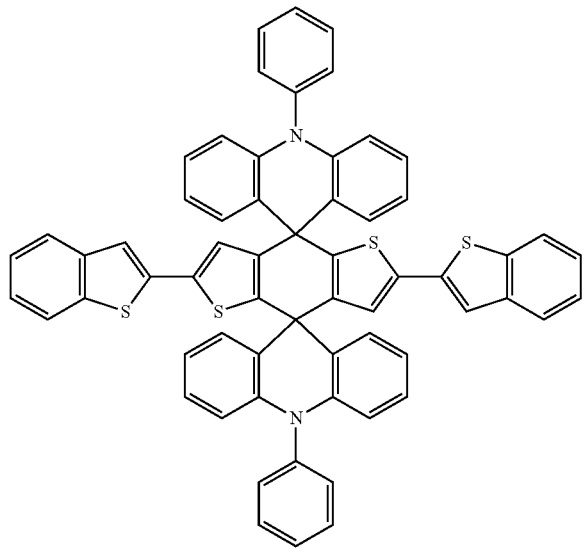
13
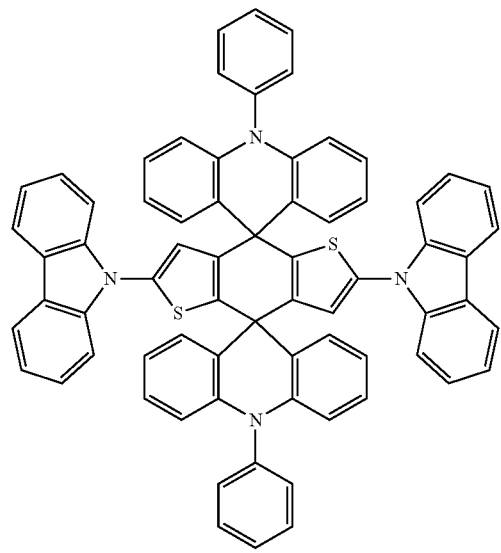
14
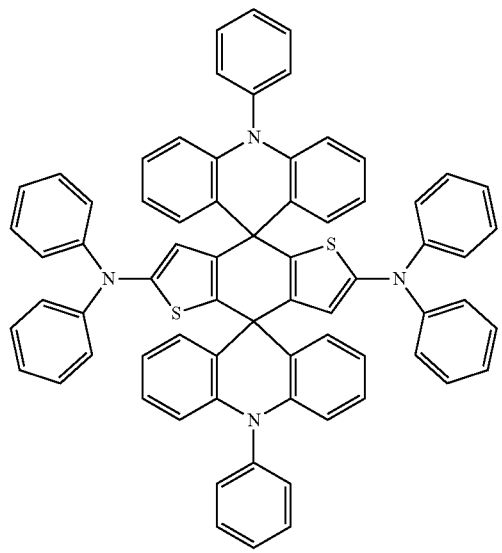
15
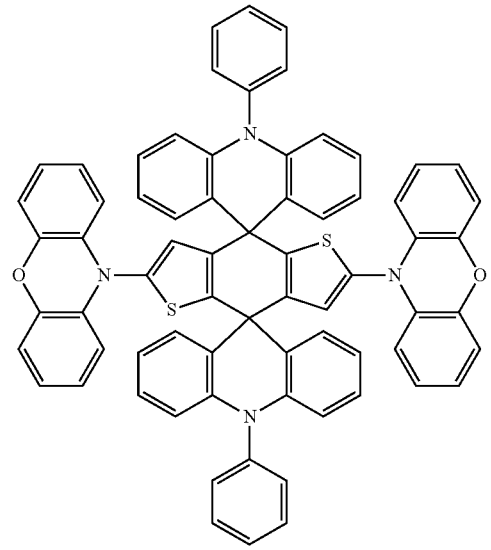
16
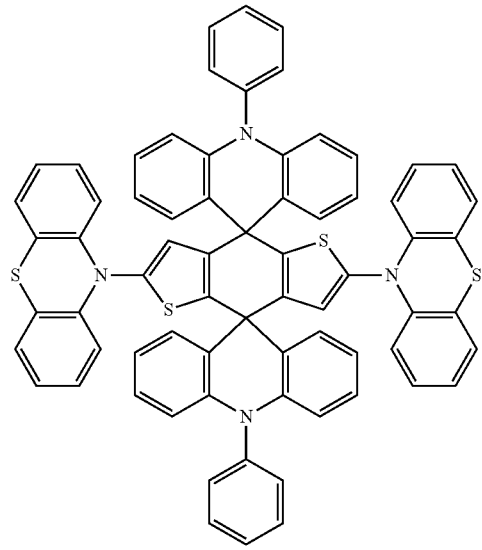

-continued
17
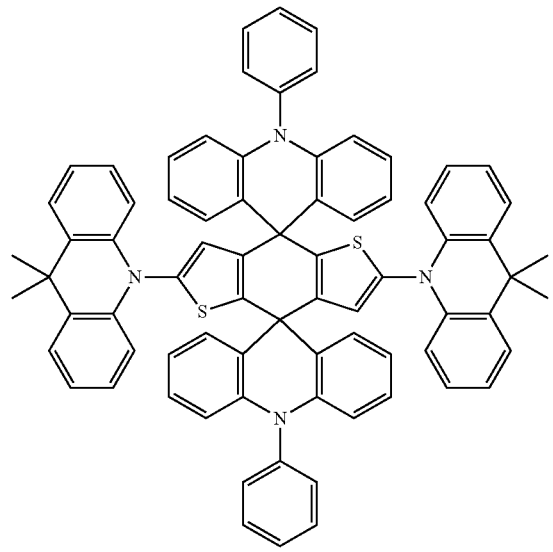
18
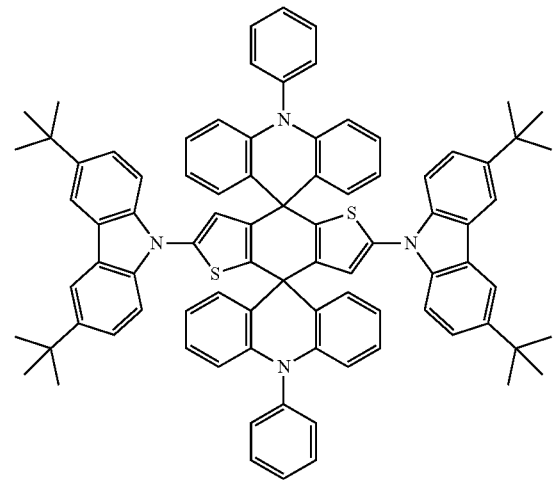
19
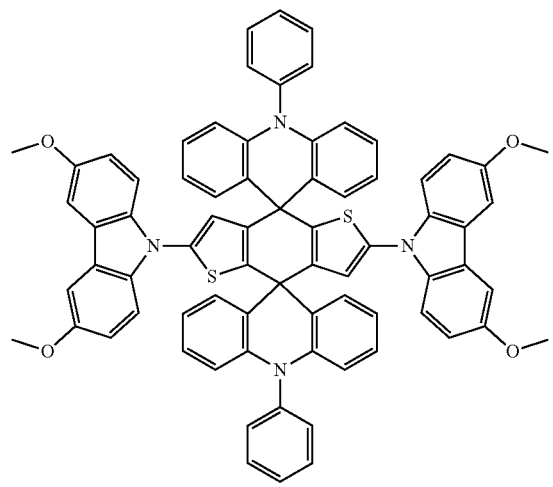
20
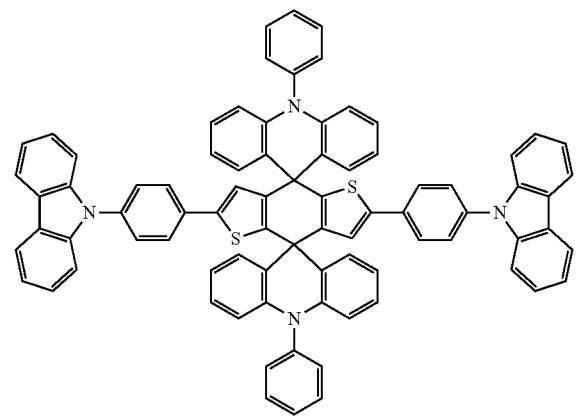
21
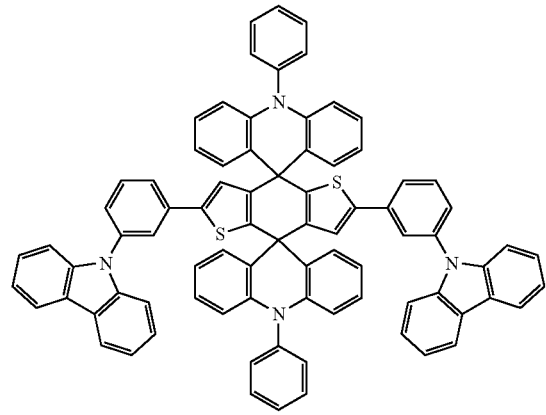
22
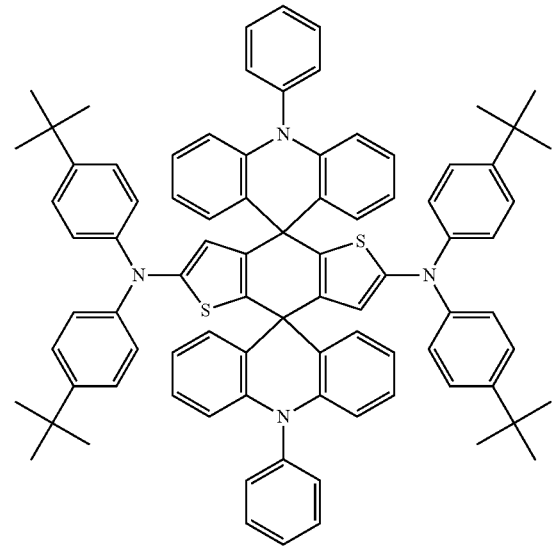

-continued
| 23 | 24 |
|---|---|
| 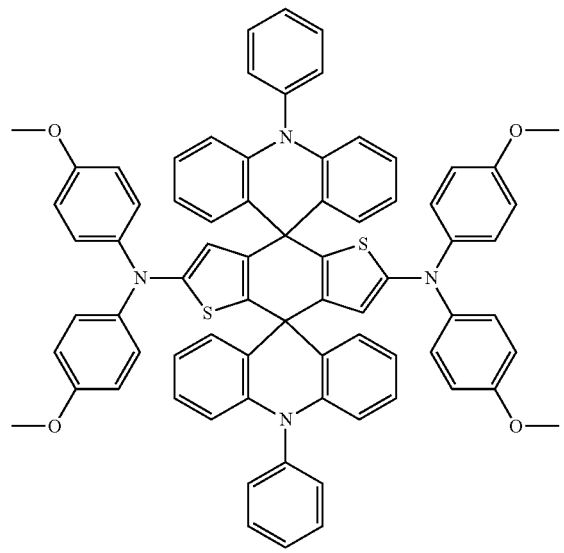 | 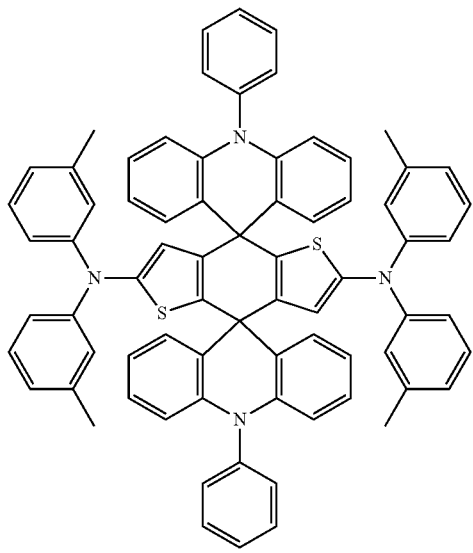 |
| 25 | 26 |
|---|---|
| 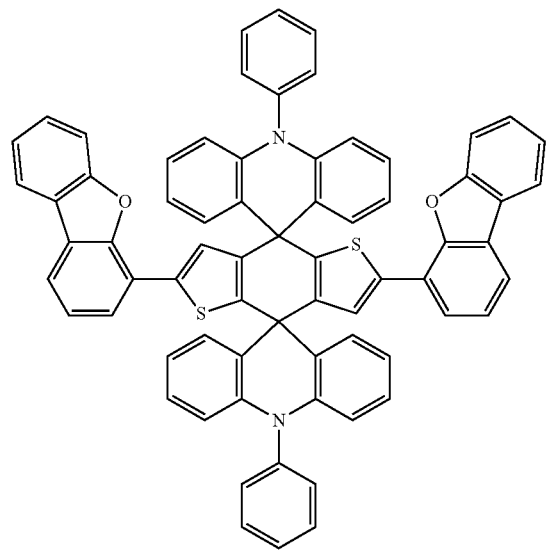 | 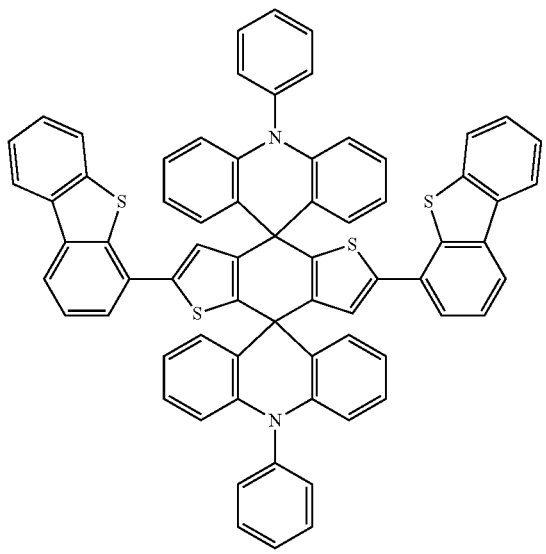 |
| 27 | 28 |
|---|---|
| 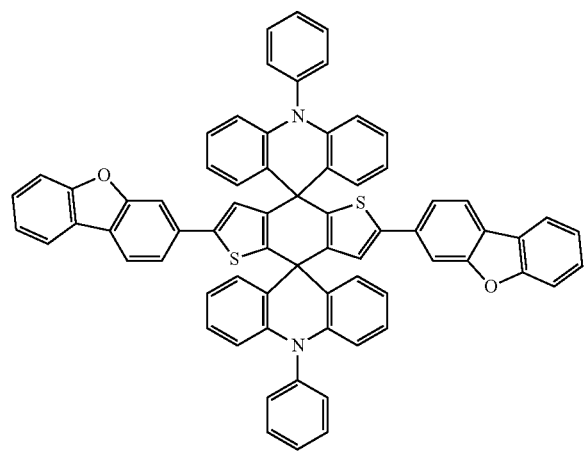 | 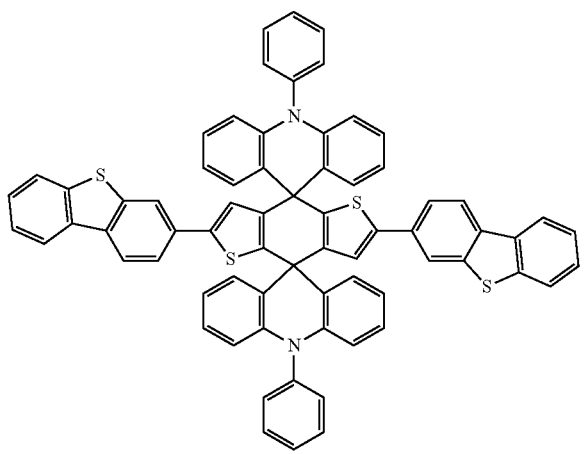 |

-continued
29
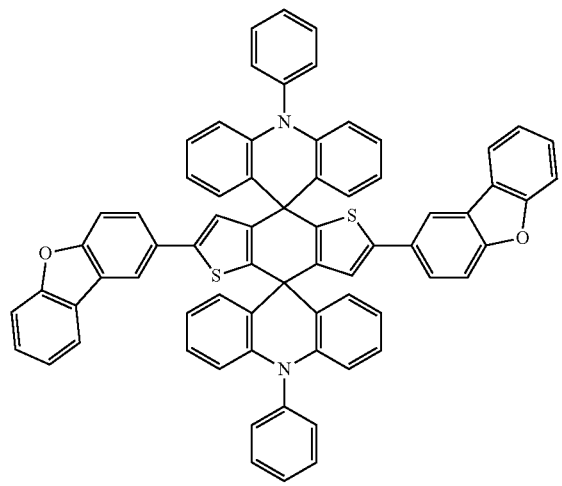
30
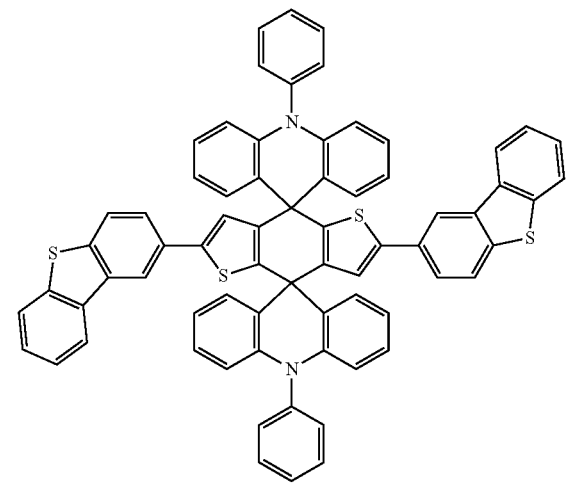
31
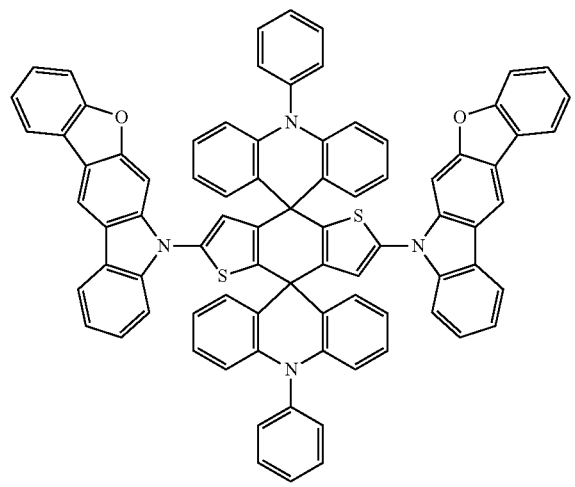
32
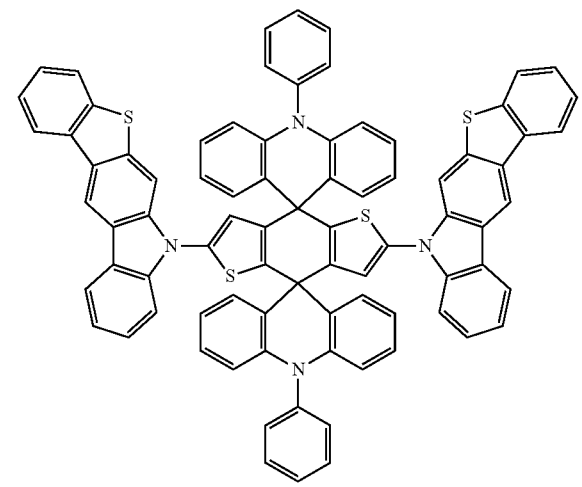
33
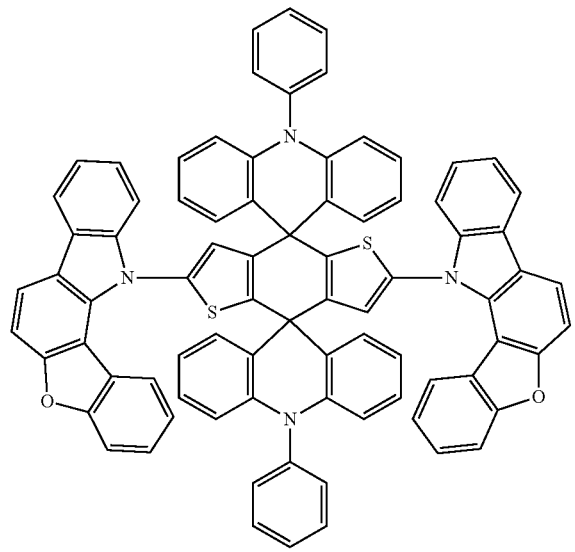
34
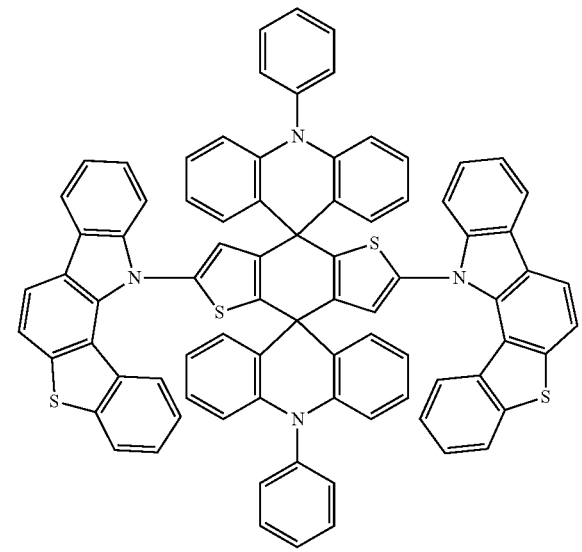

35
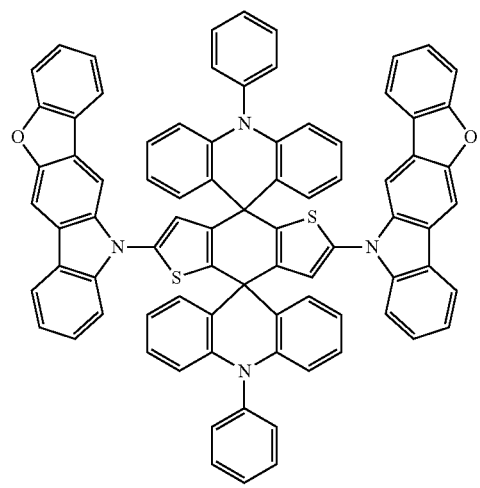
36
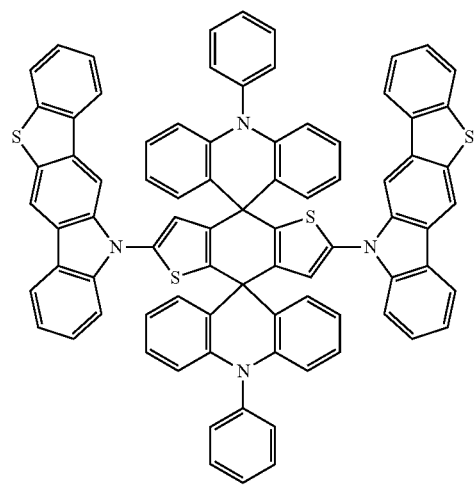
37
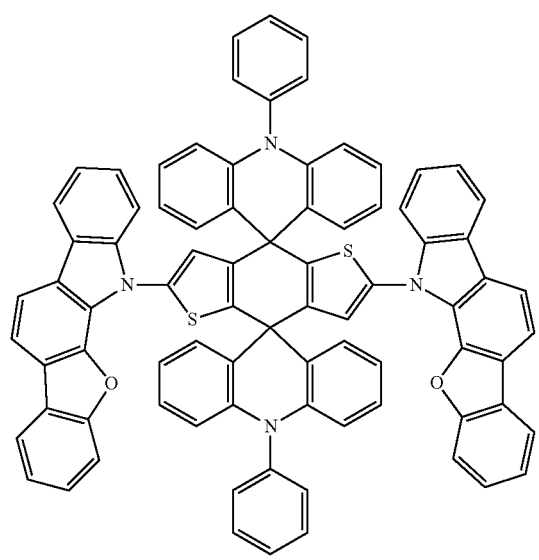
38
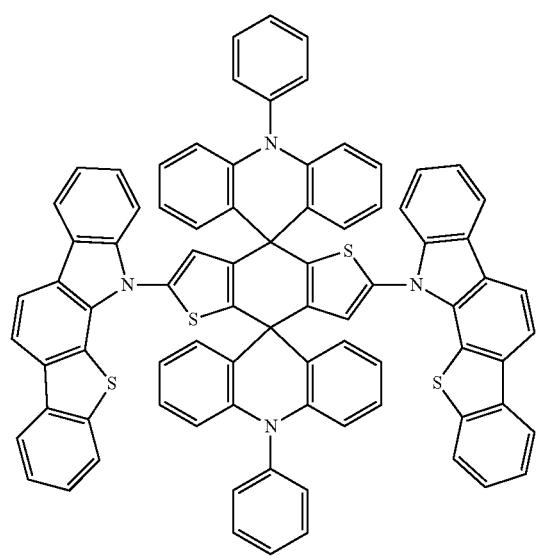
39
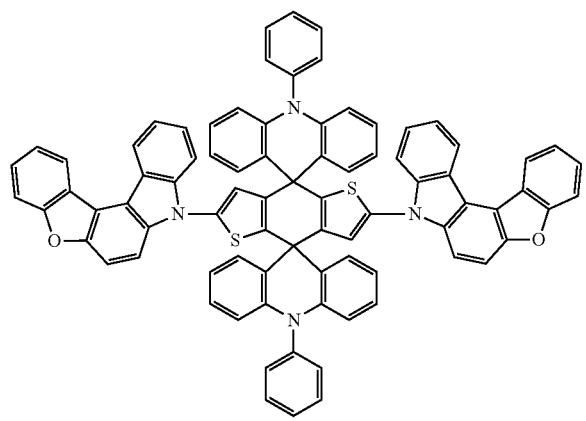
40
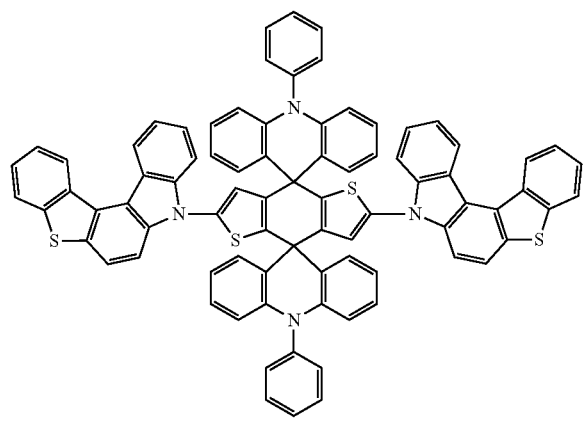

-continued
41
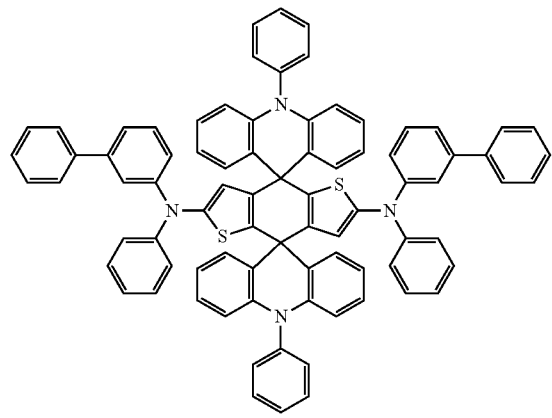
42
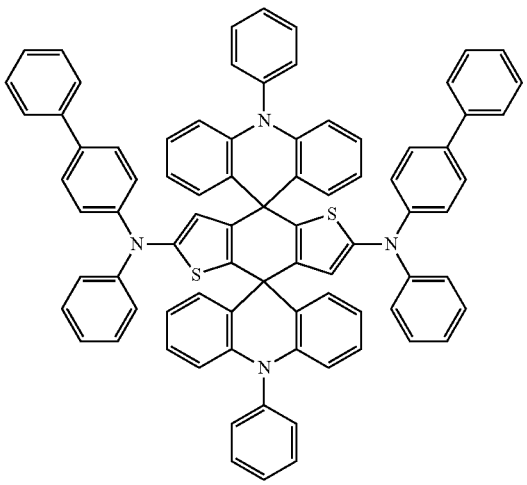
43
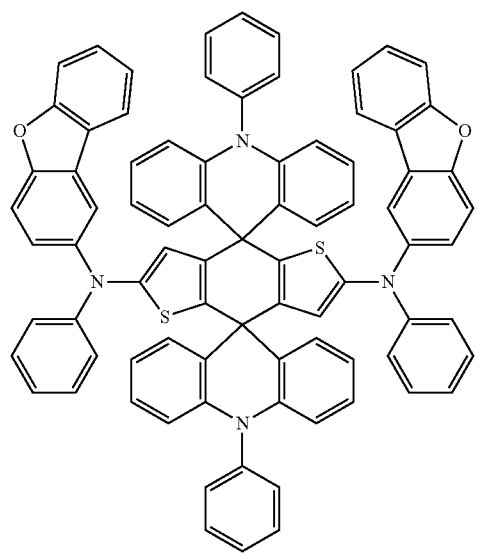
44
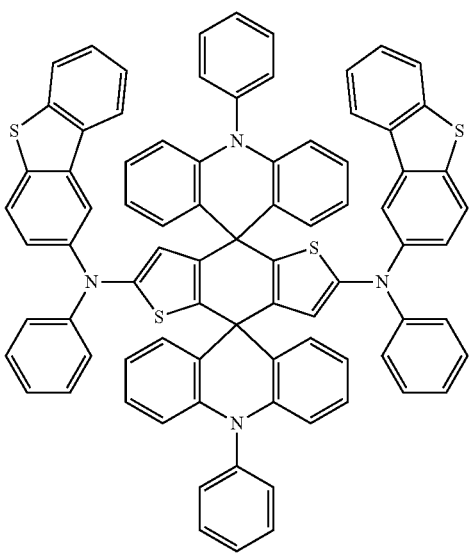
45
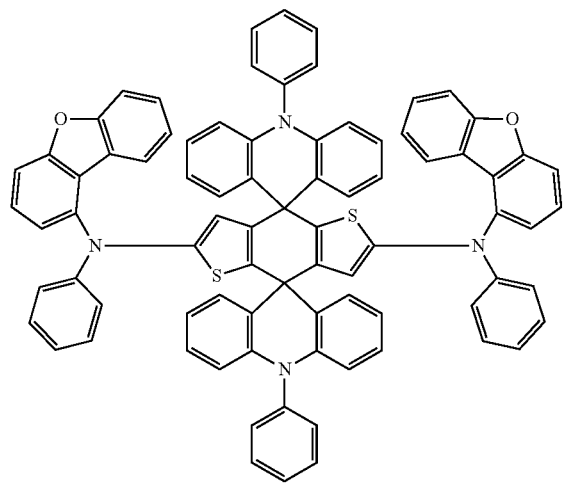
46
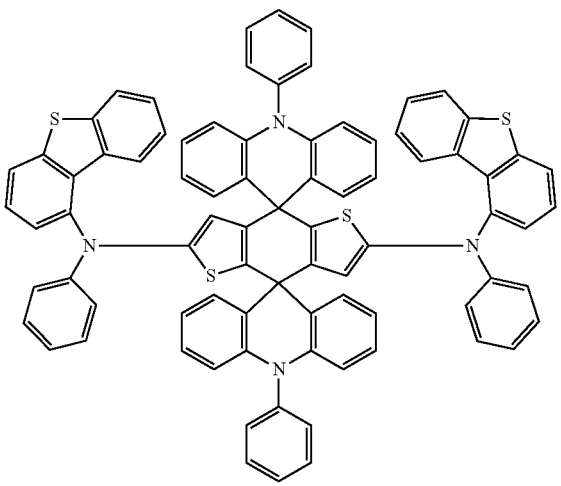

-continued
47
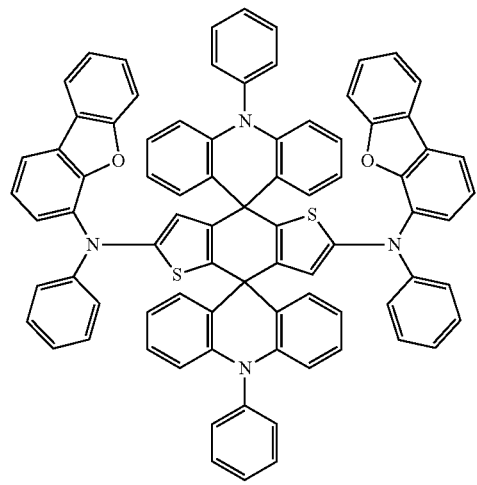
48
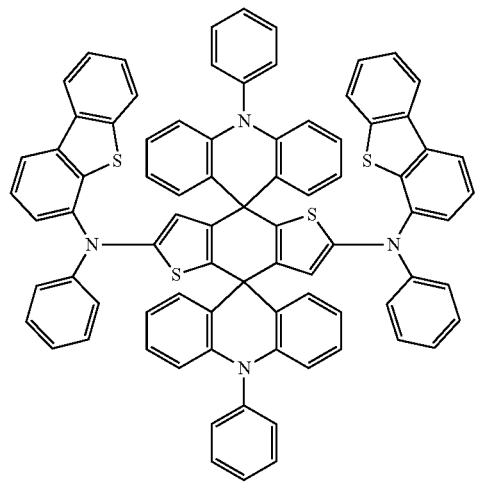
49
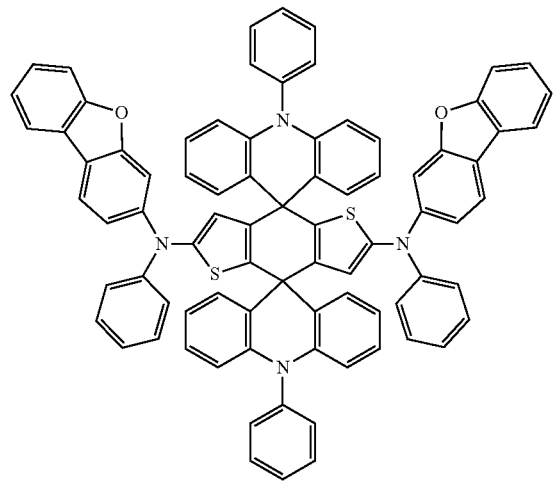
50
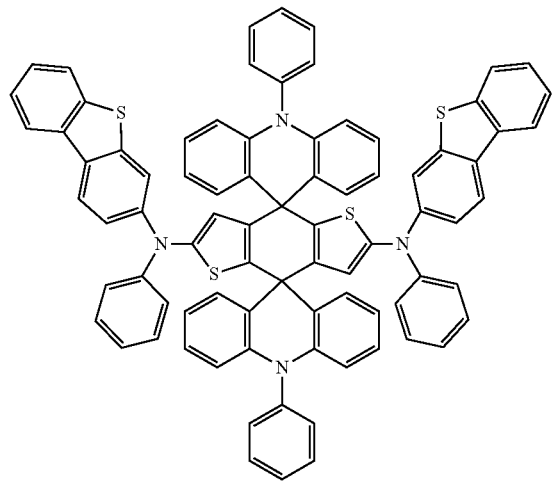
51
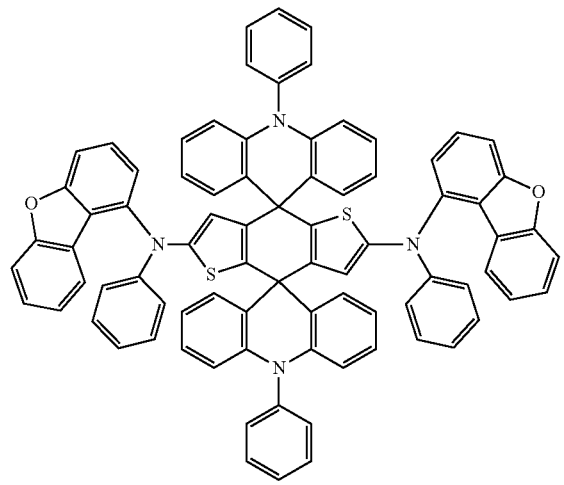
52
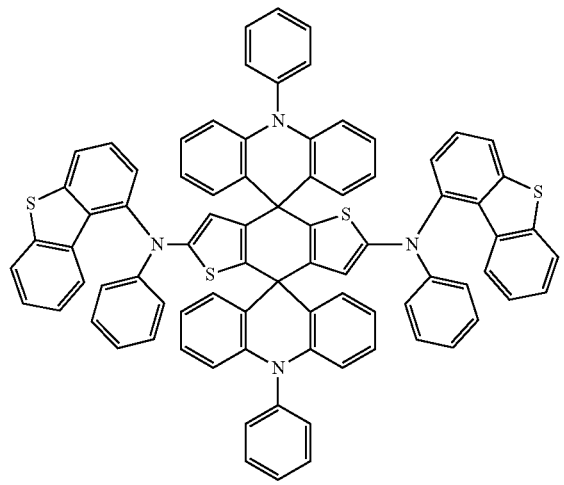

-continued
53
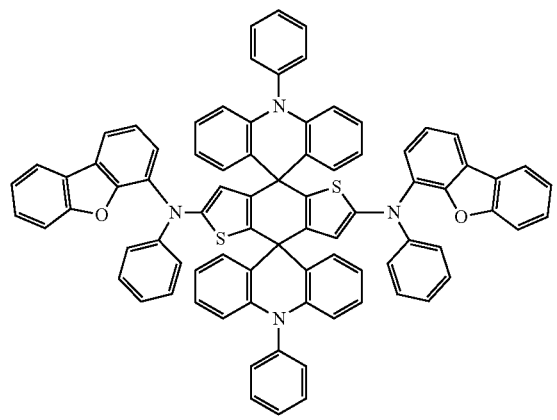
54
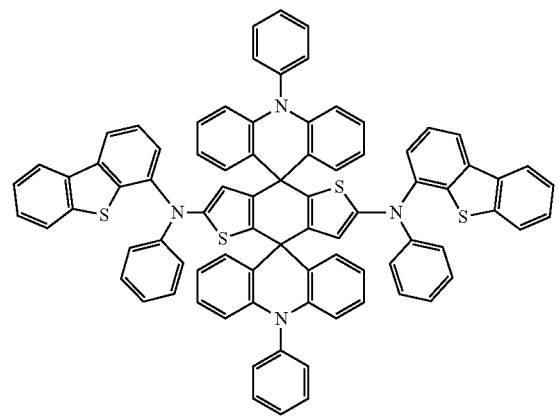
55
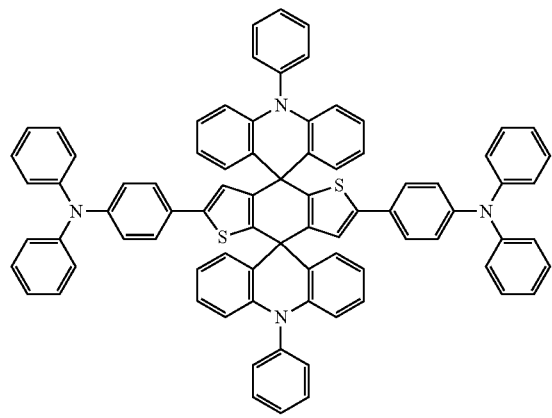
56
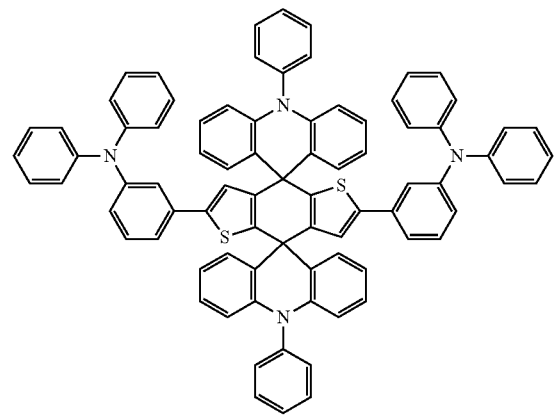
57
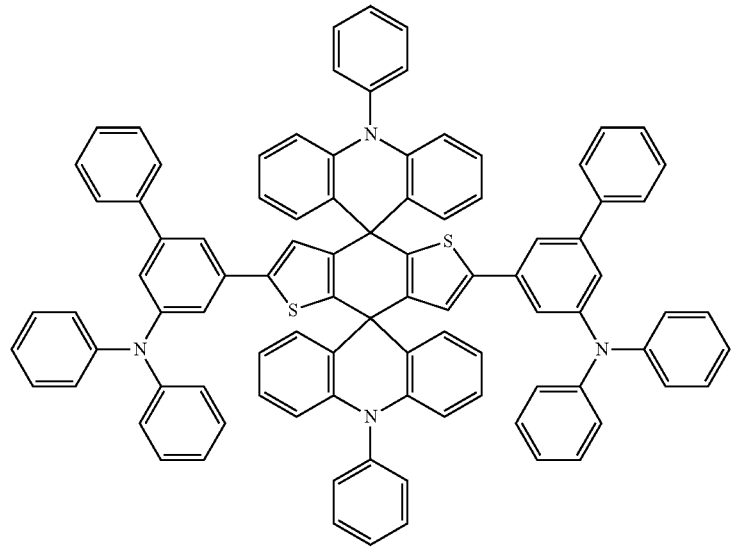

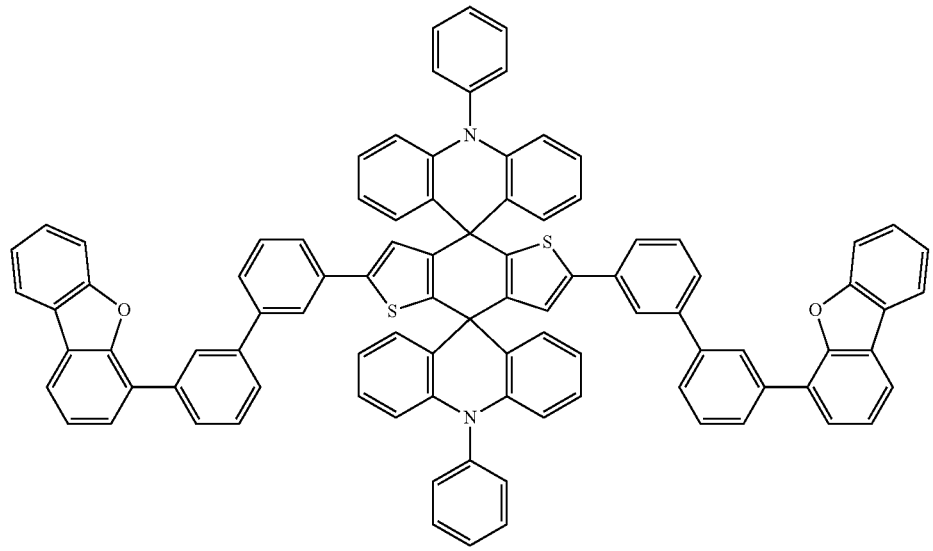
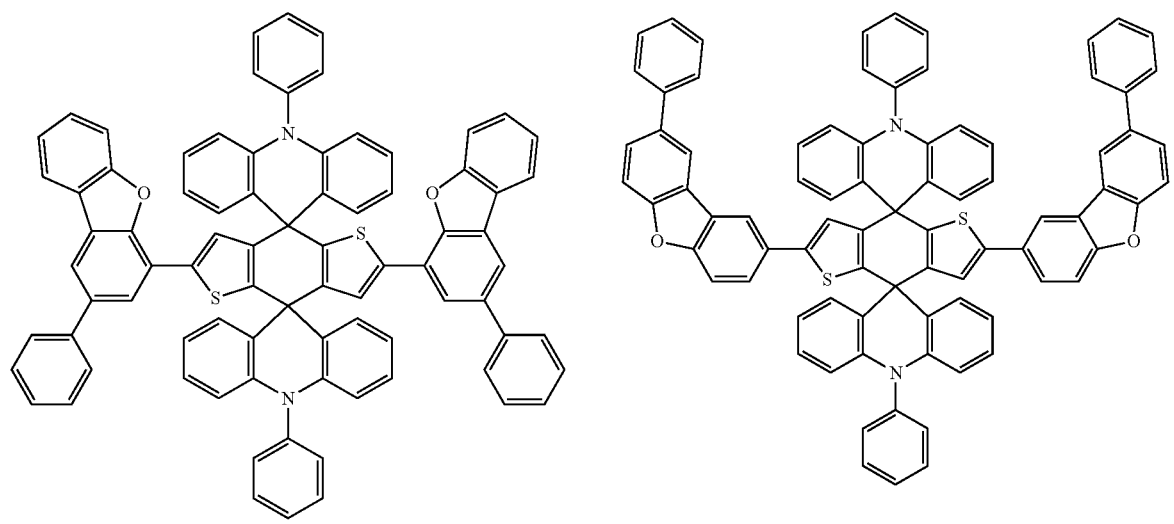
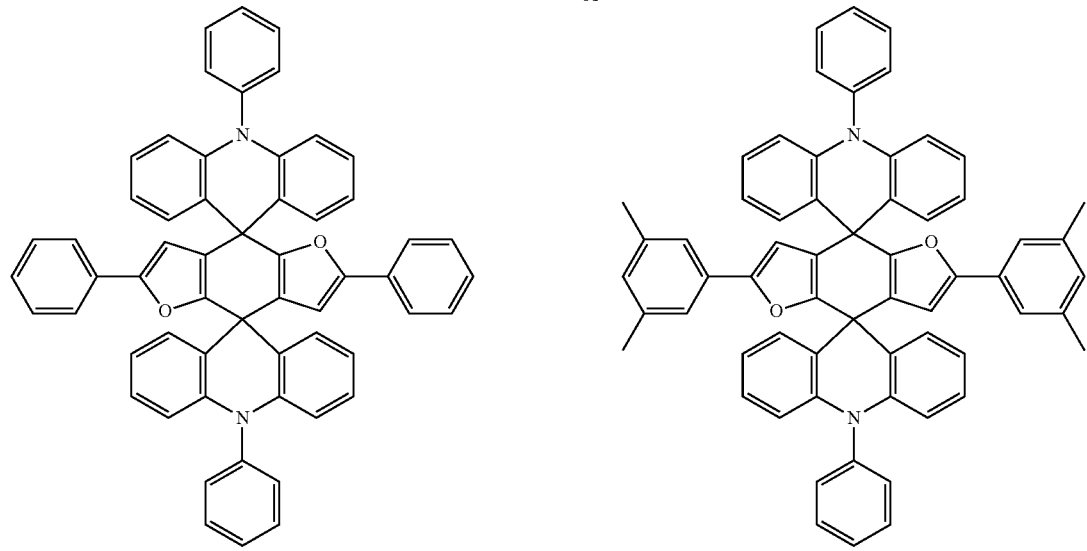

-continued
63
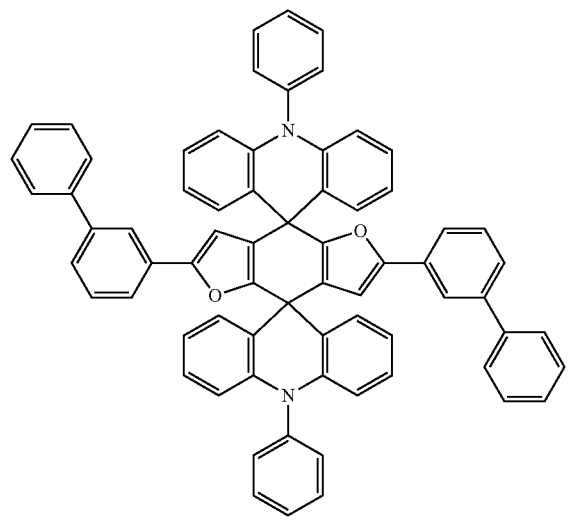
64
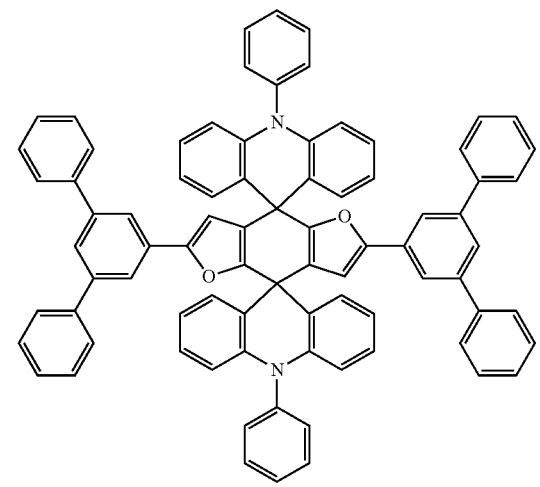
65
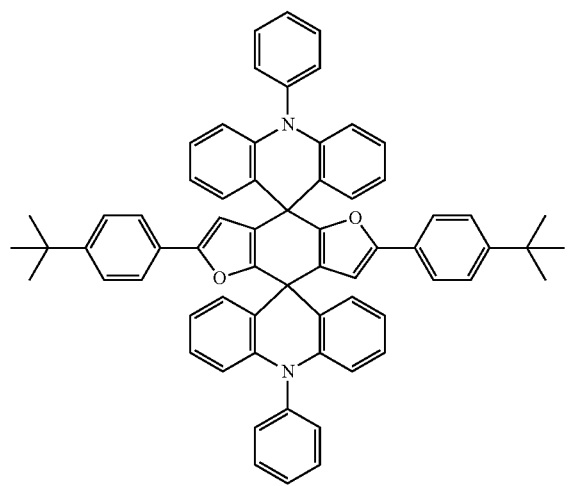
66
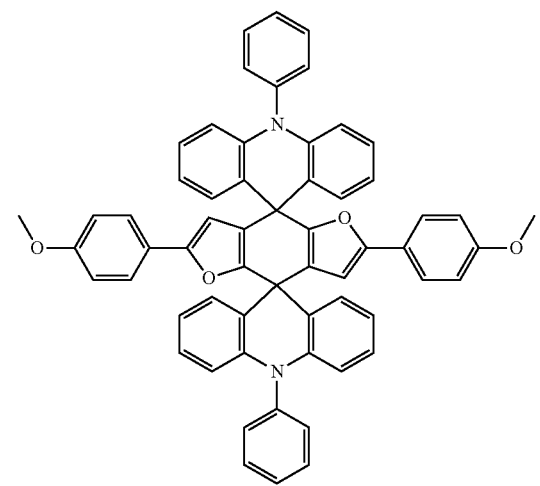
67
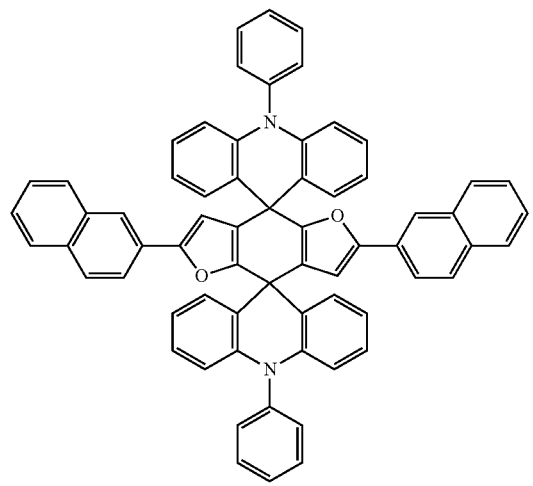
68
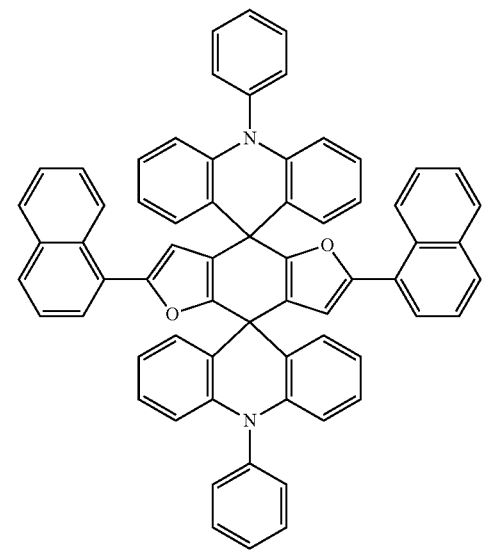

69
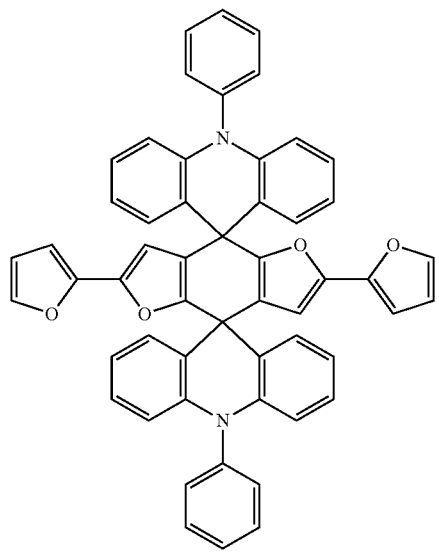
70
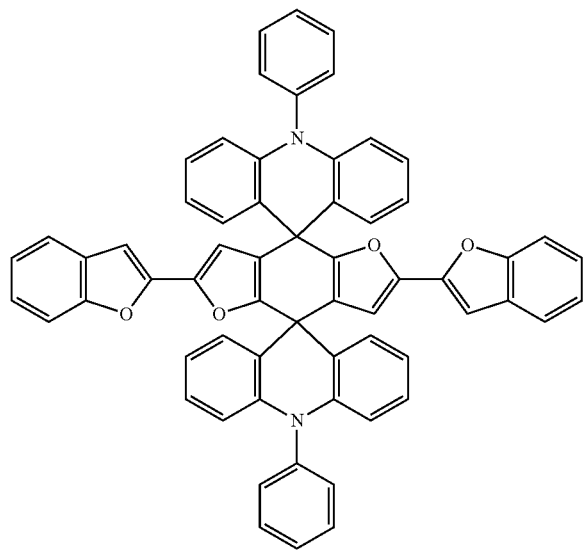
71
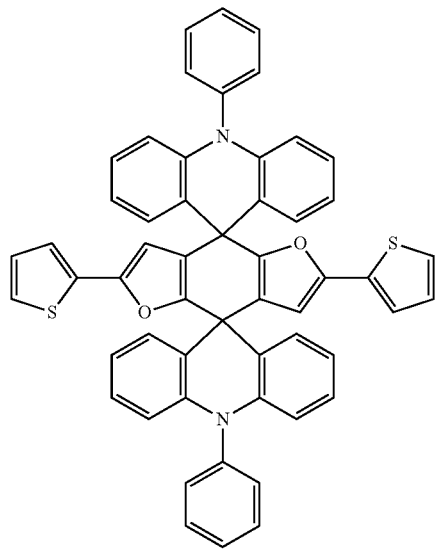
72
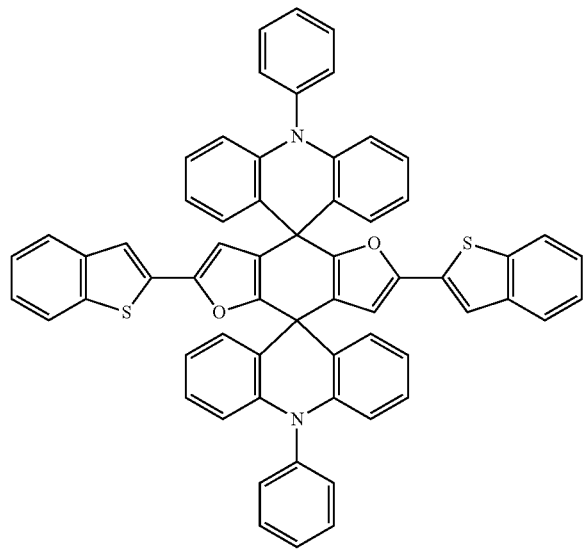

-continued
73
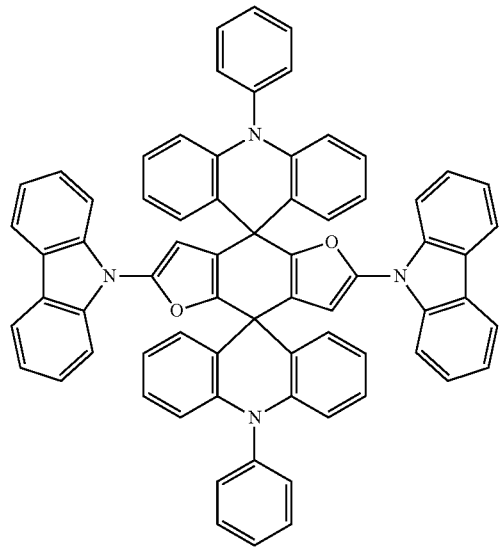
74
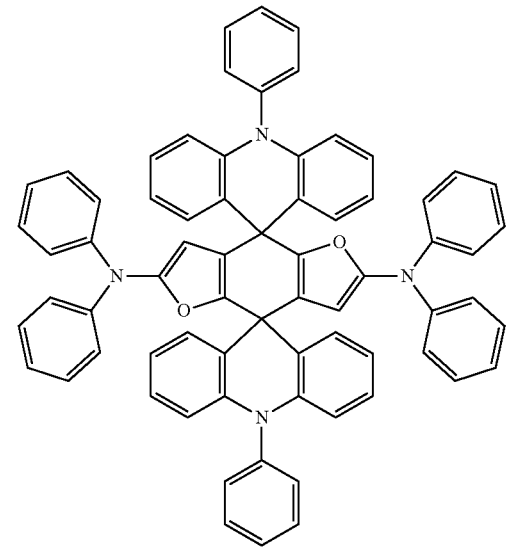
75
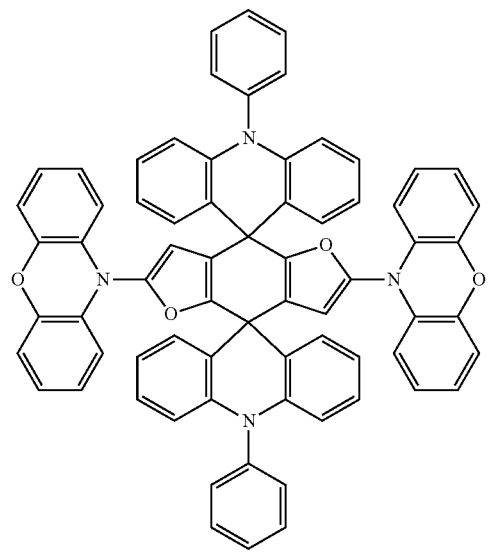
76
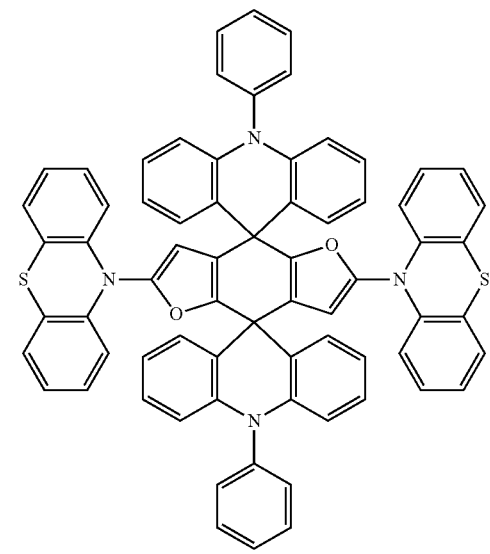
77
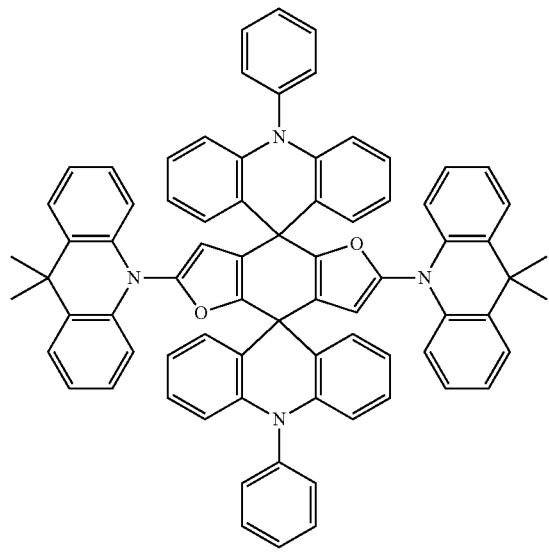
78
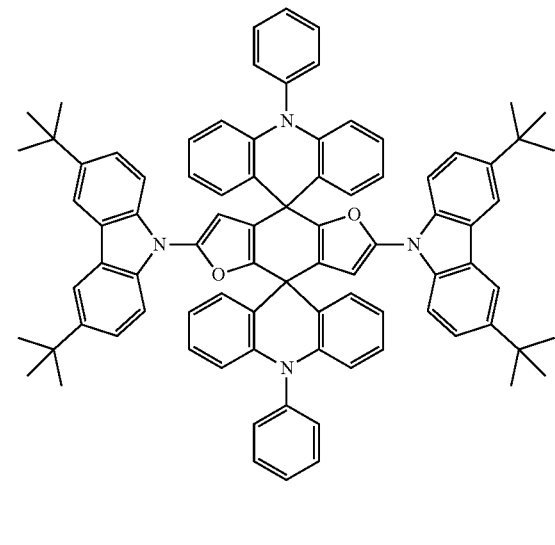

-continued
79
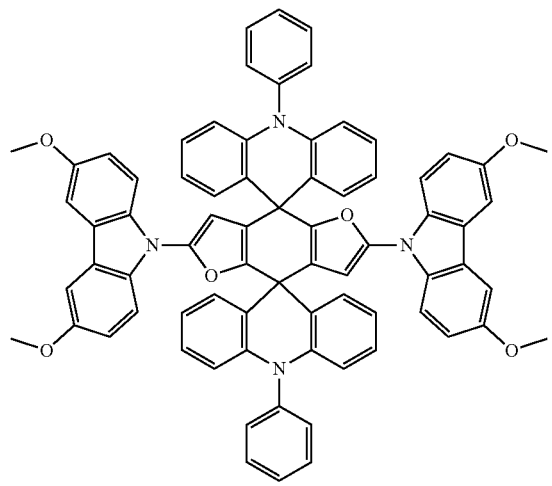
80
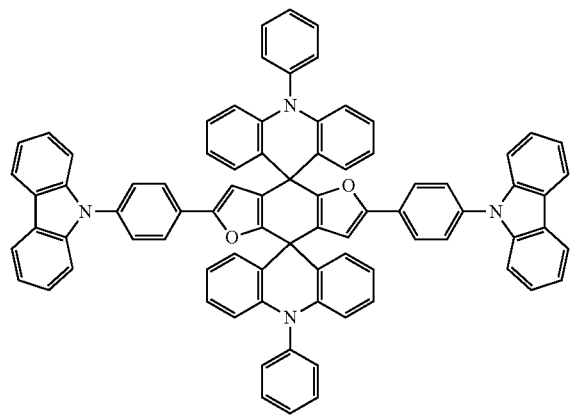
81
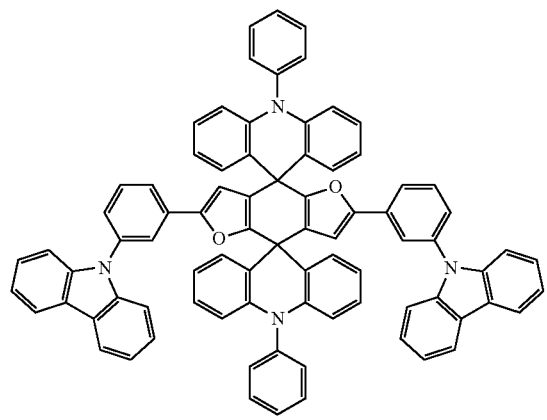
82
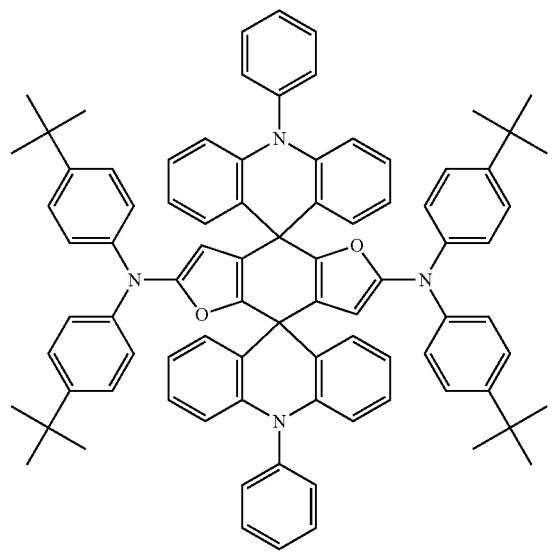
83
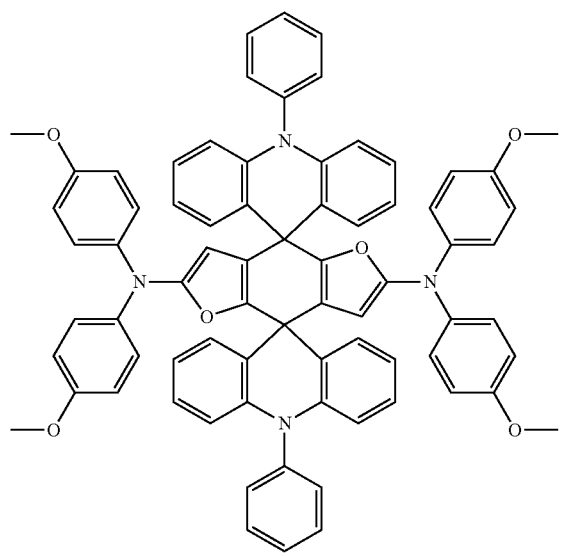
84
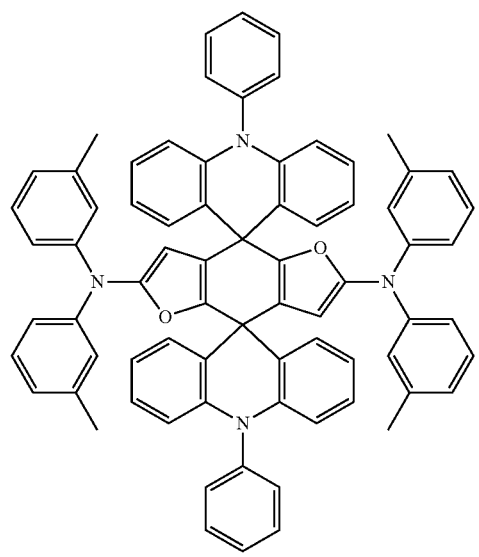

85
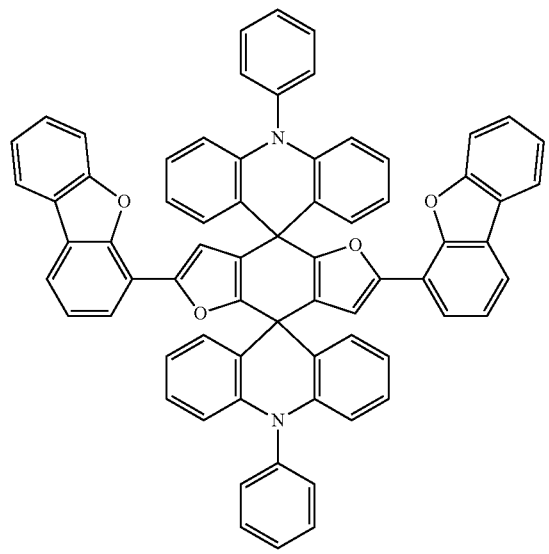
86
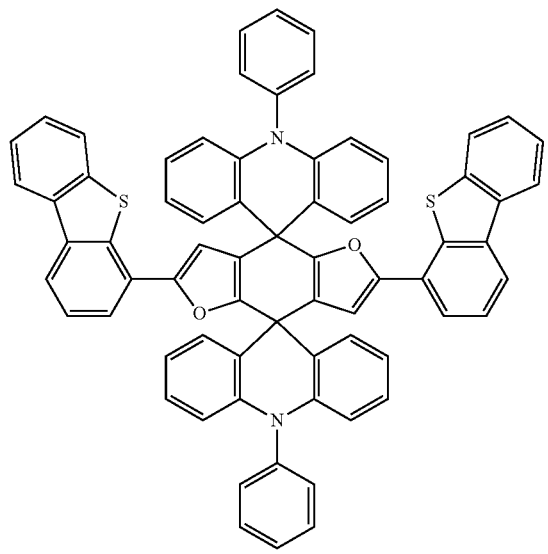
87
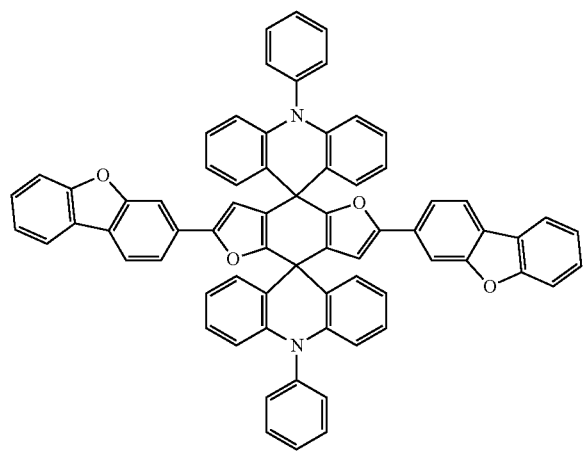
88
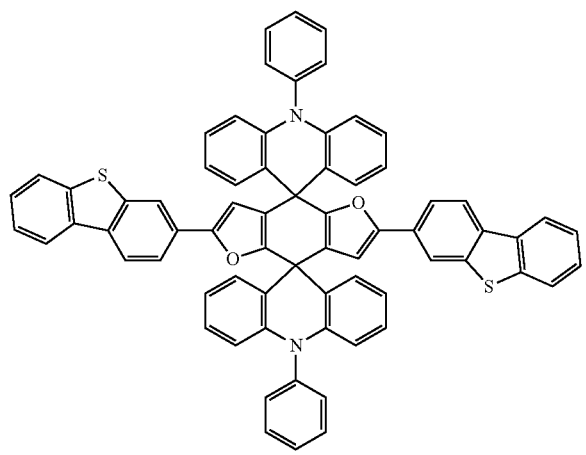
89
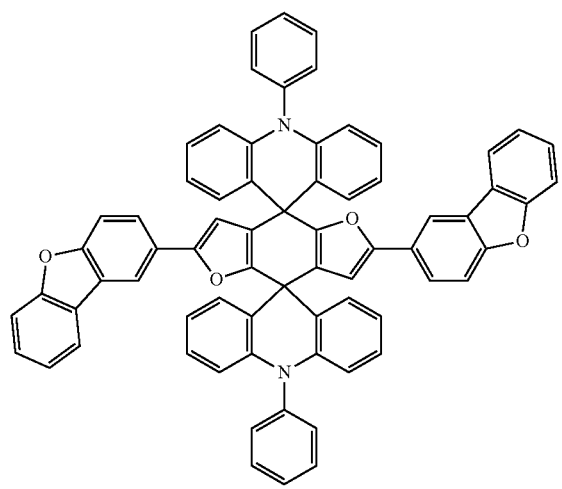
90
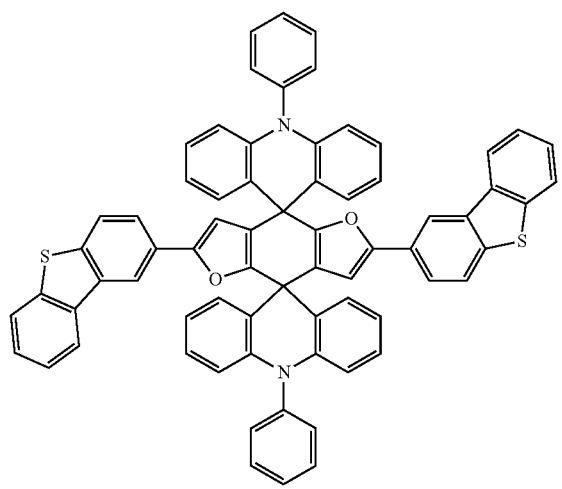

-continued
91
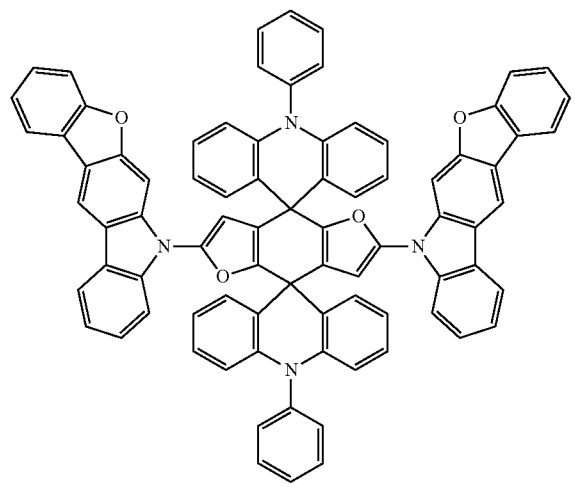
92
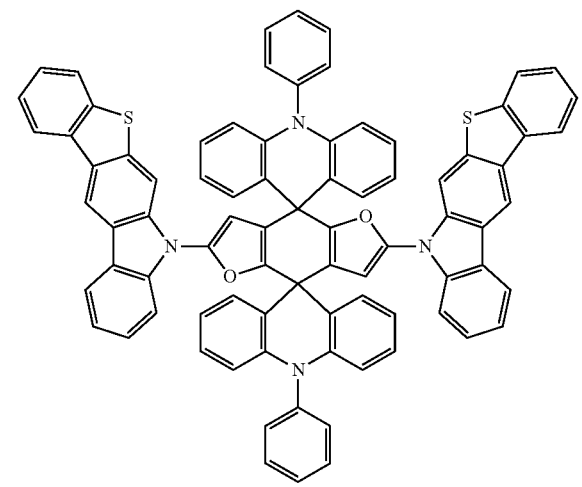
93
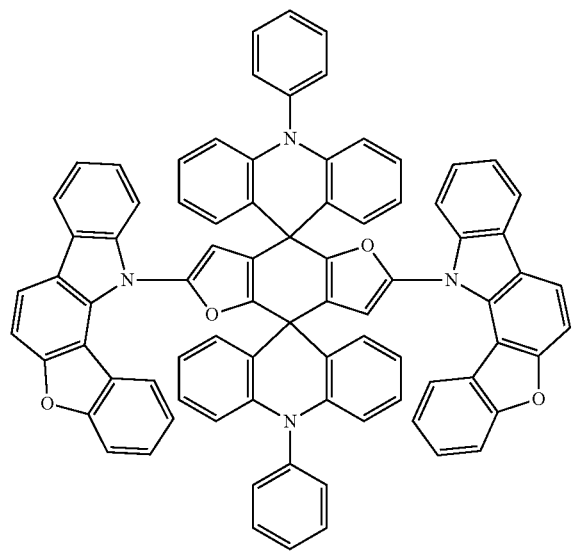
94
95
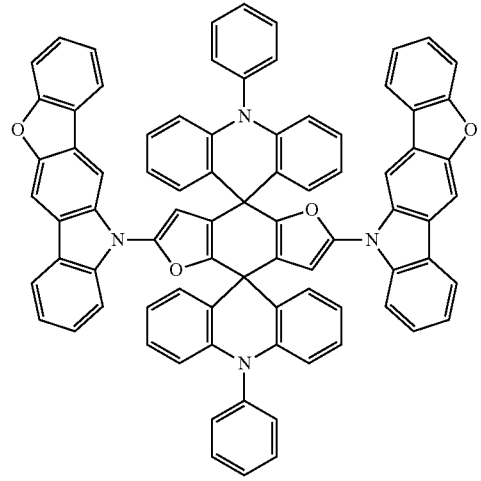
96
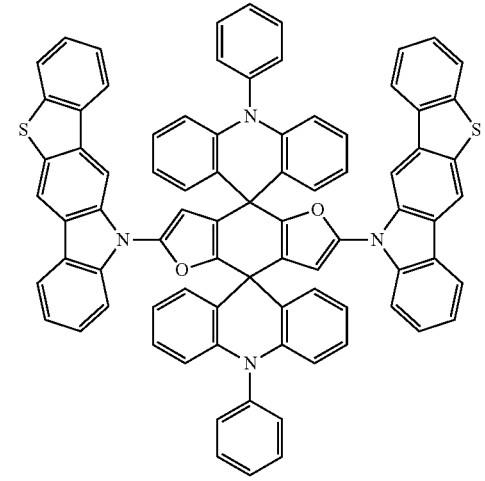

97
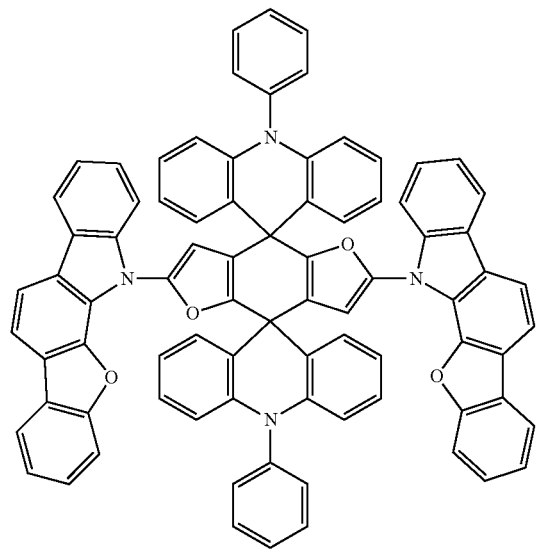
98
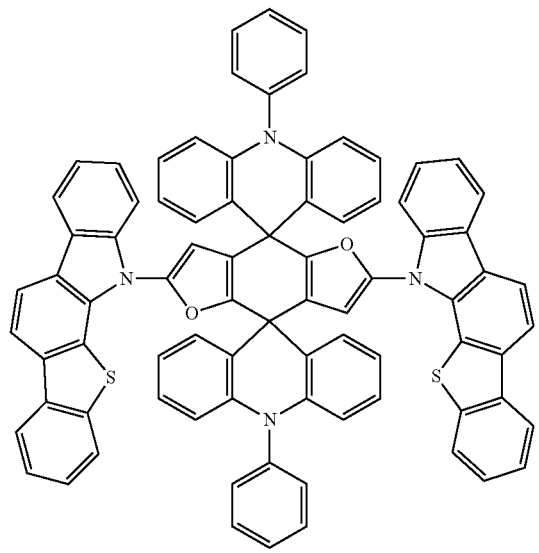
99
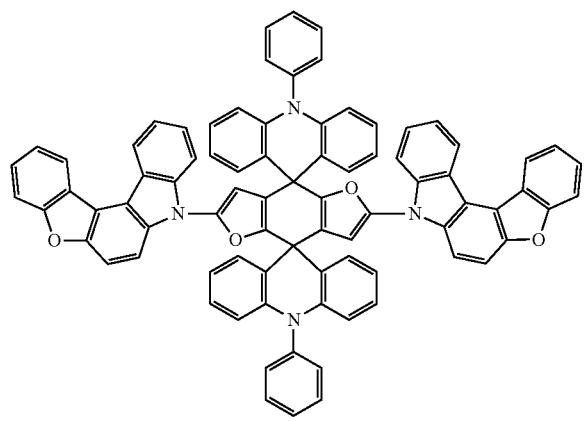
100
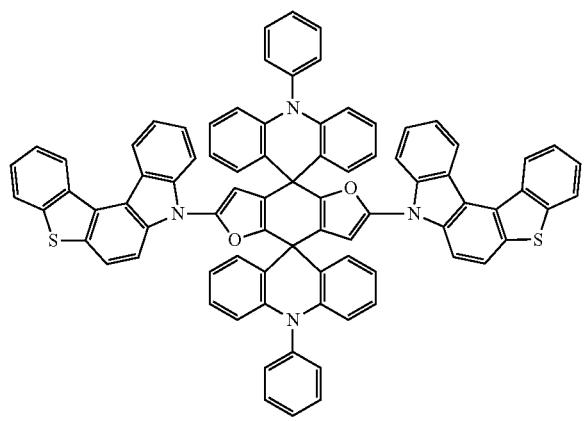
101
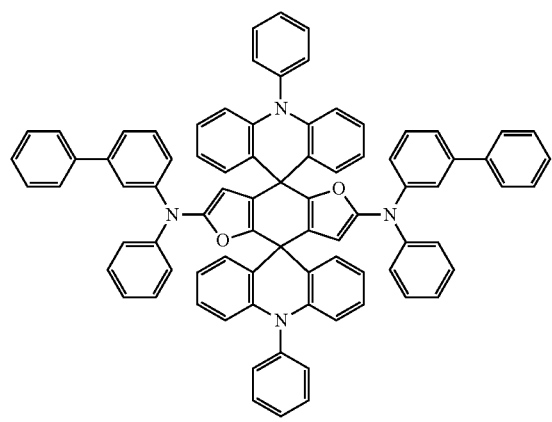
102
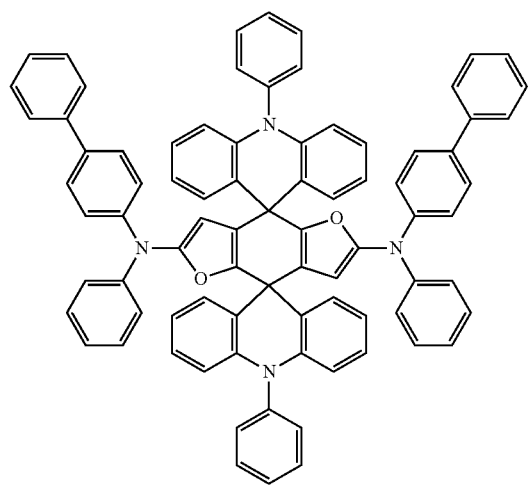

-continued
103
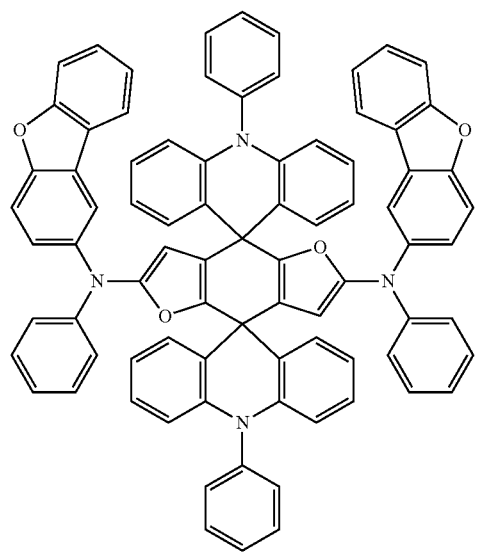
104
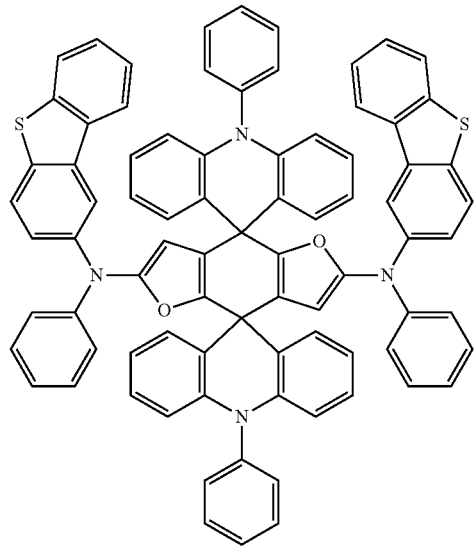
105 106
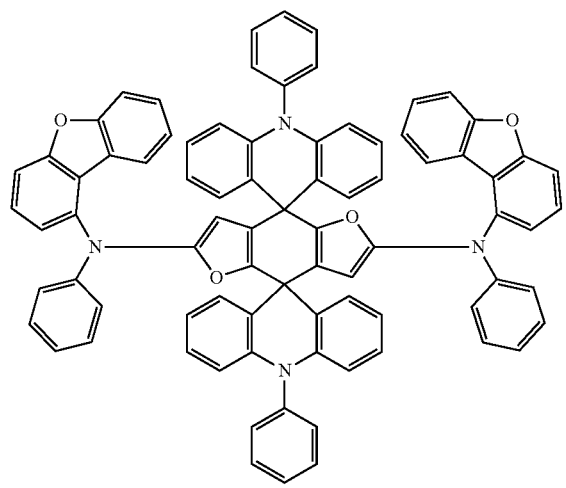
107
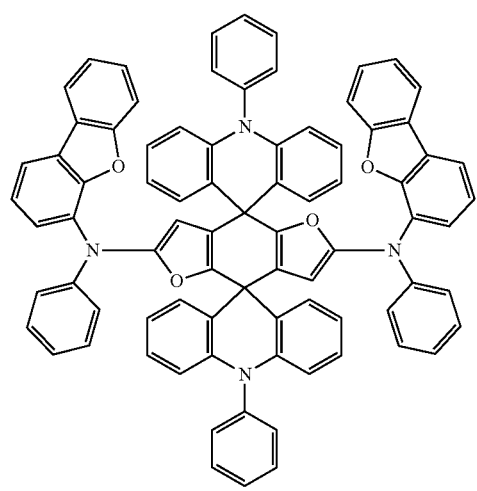
108
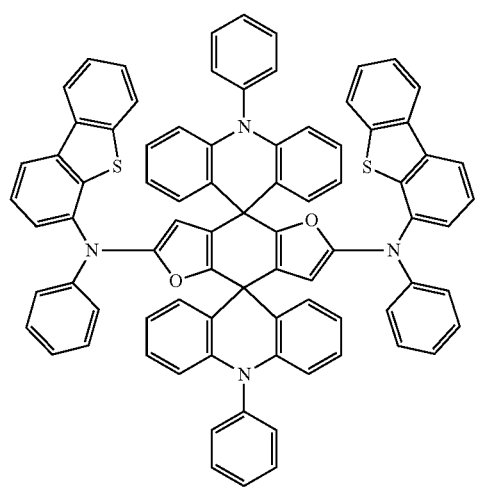

-continued
109
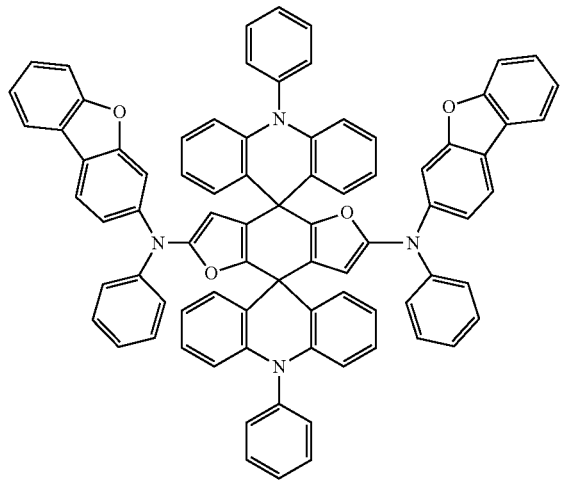
110
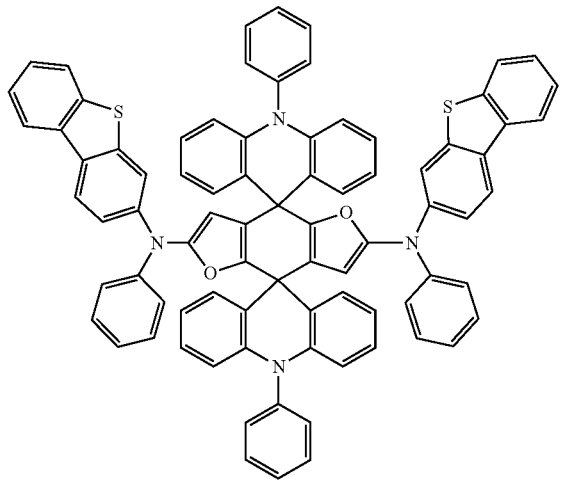
111
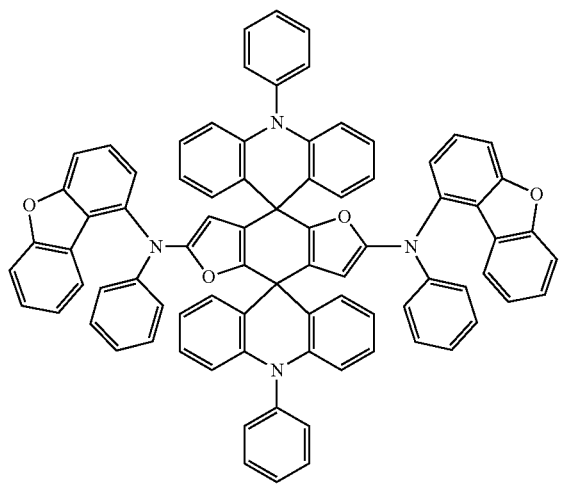
112
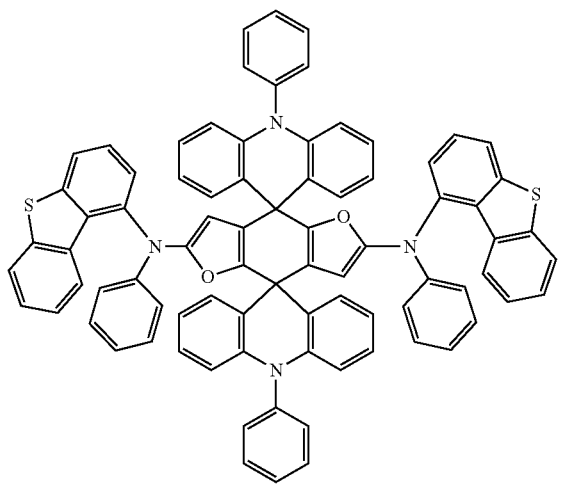
113
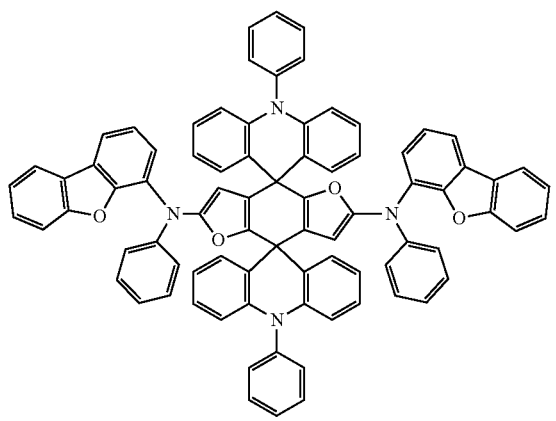
114
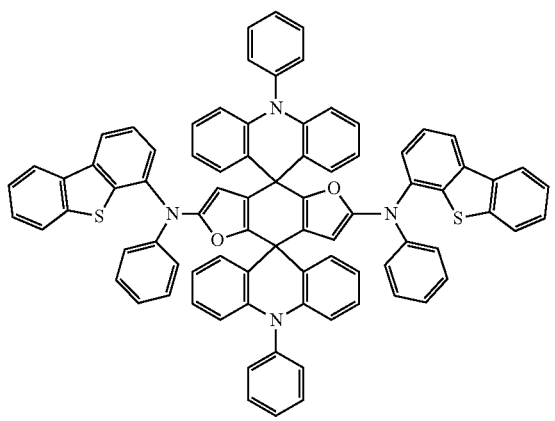

-continued
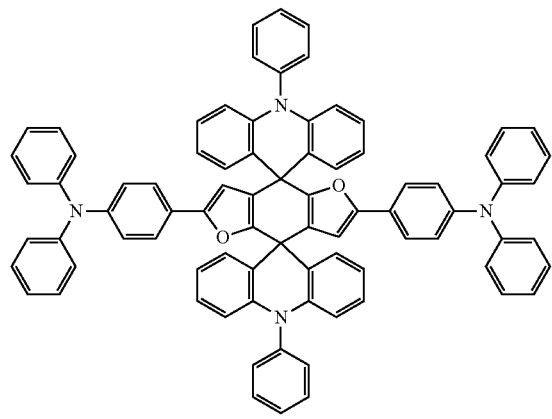
115
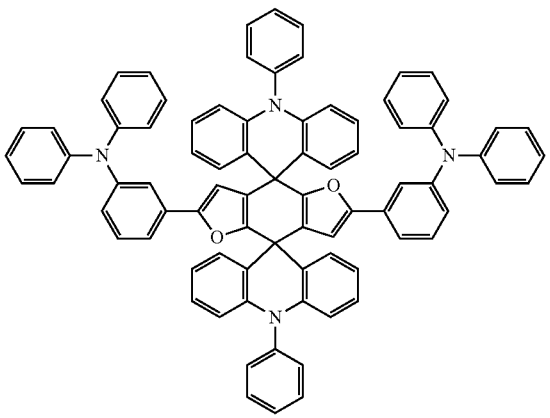
116
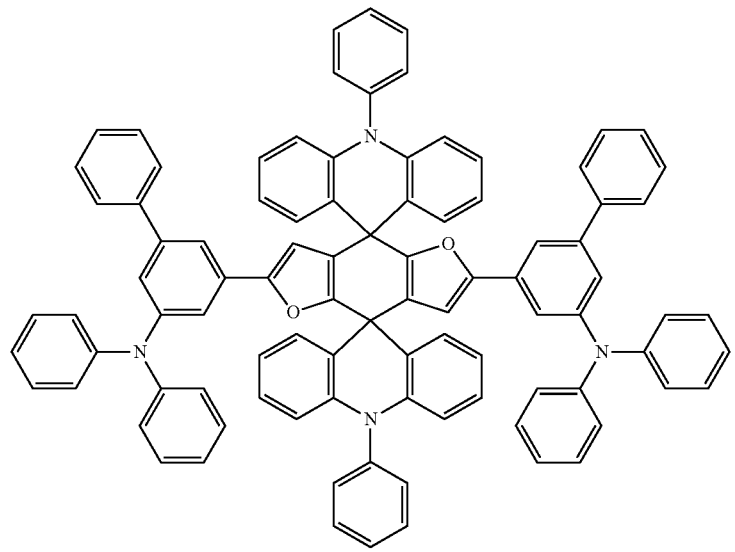
117
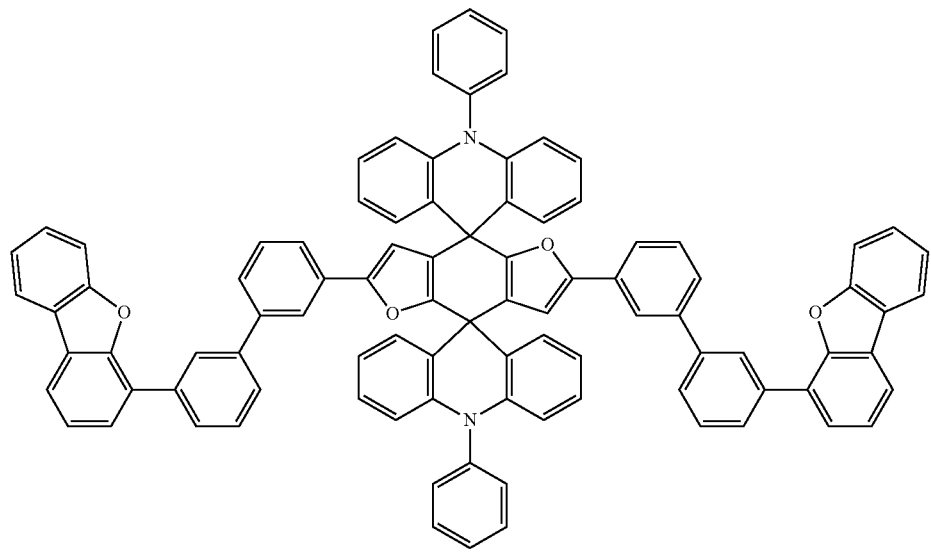
118

-continued
119
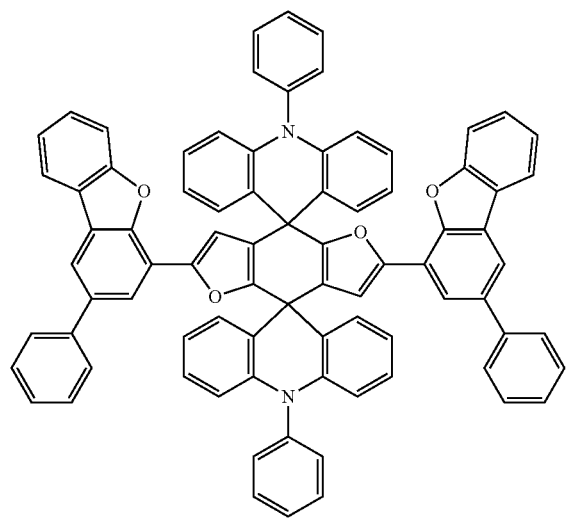
120
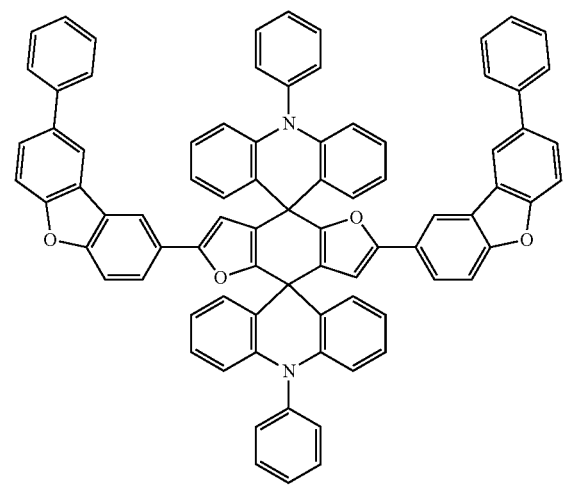
121
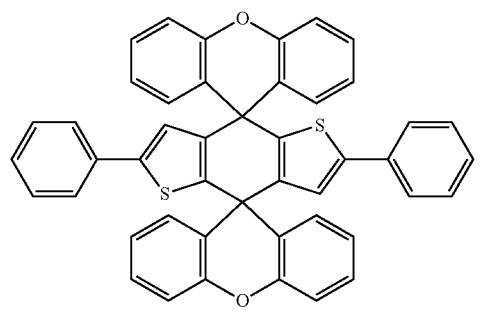
122
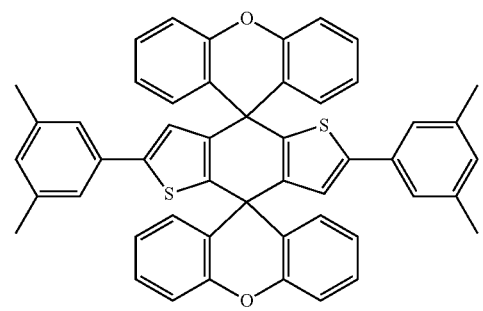
123
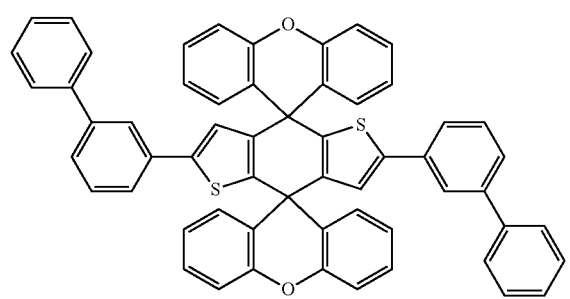
124
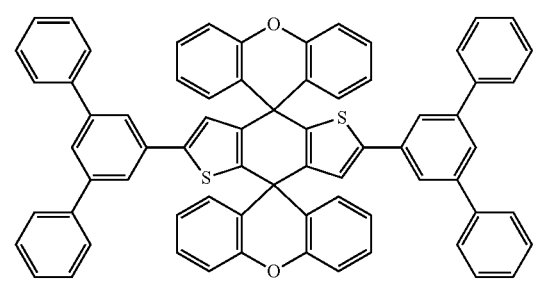
125
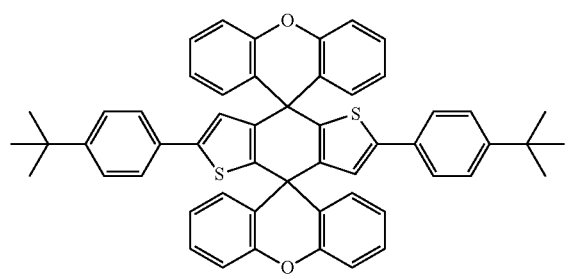
126
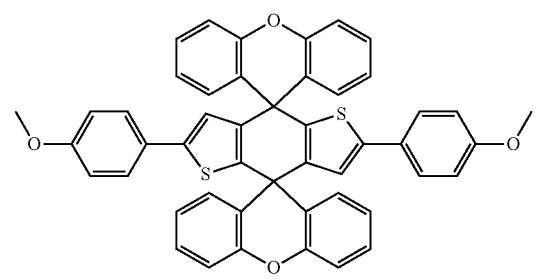

-continued
127 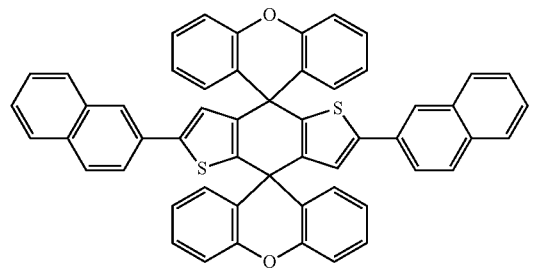 128 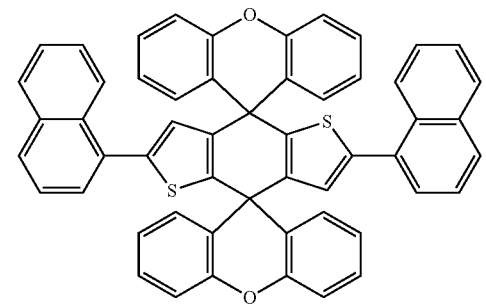
129 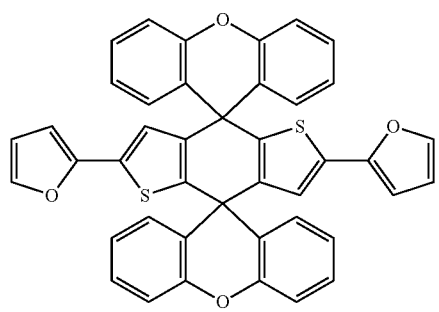 130 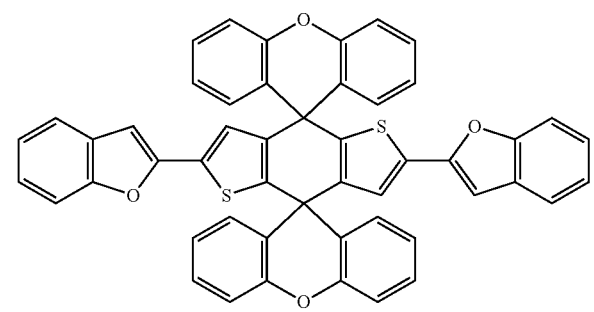
131 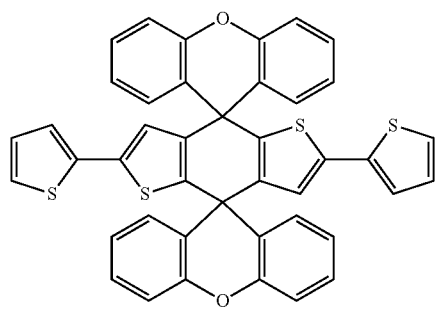 132 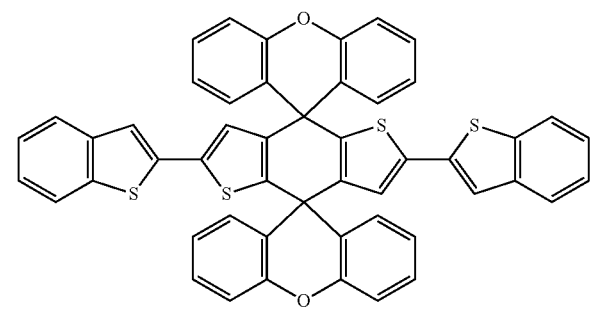
133 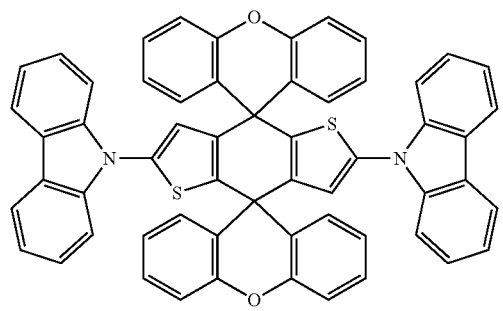 134 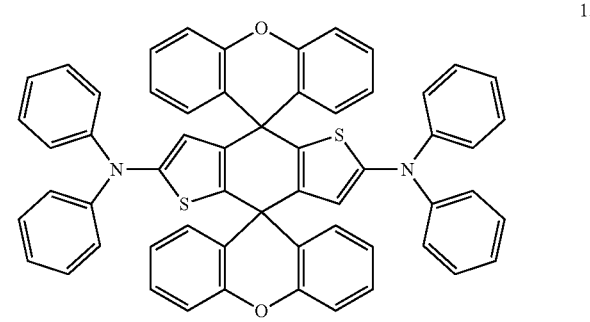
135 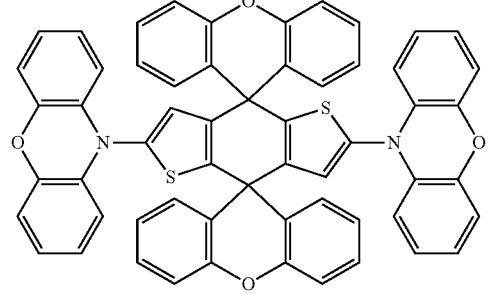 136 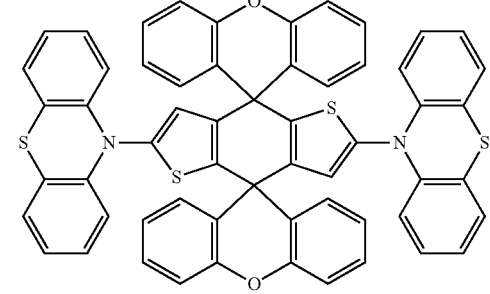

-continued
| 137 | 138 |
|---|---|
| 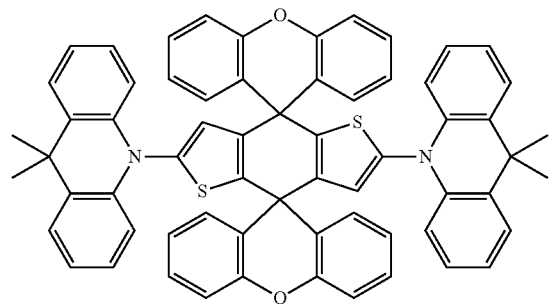 | 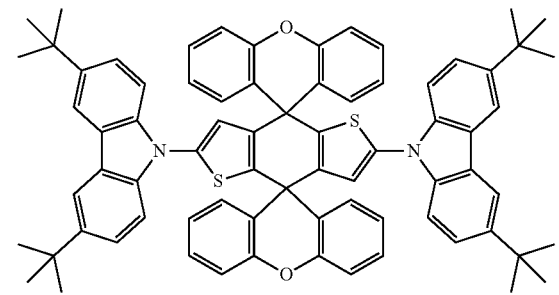 |
| 139 | 140 |
| 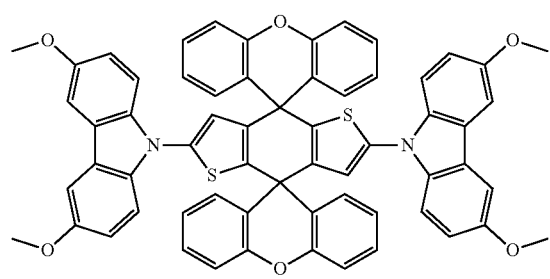 | 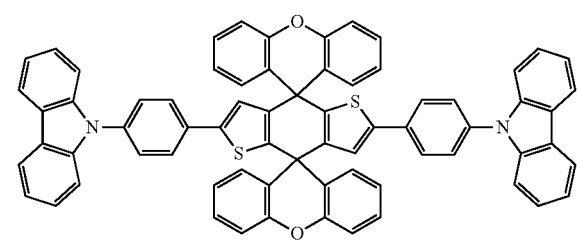 |
| 141 | 142 |
| 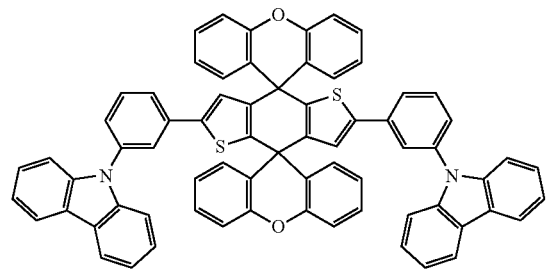 | 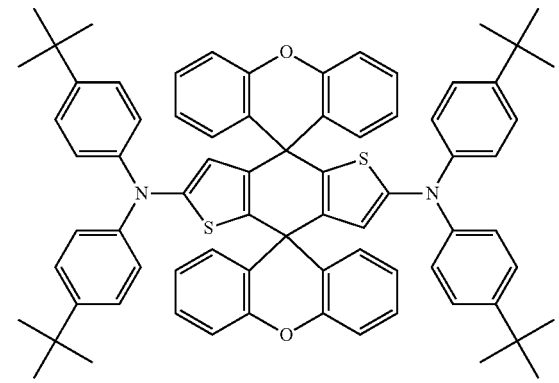 |
| 143 | 144 |
| 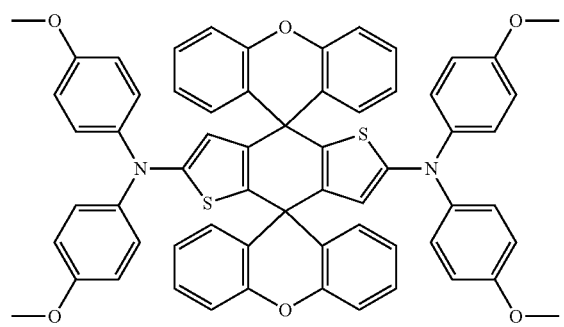 | 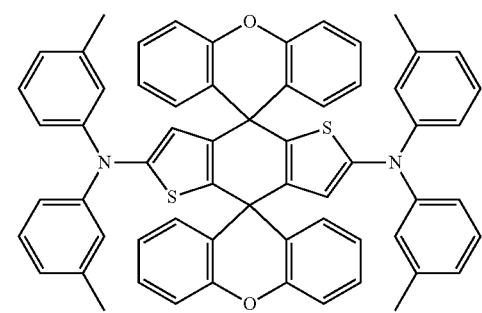 |

-continued
145
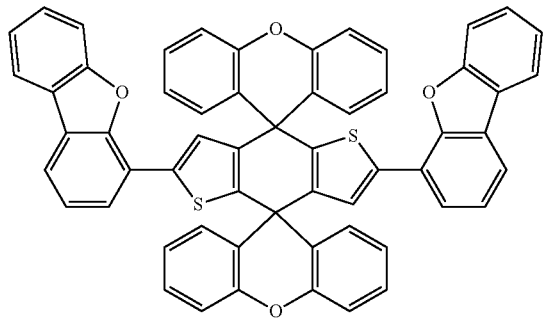
146
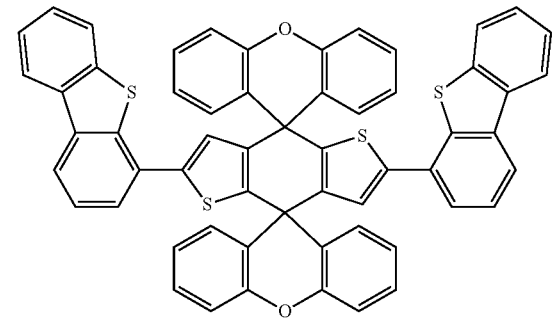
147
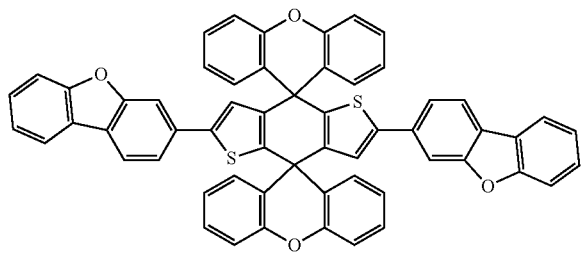
148
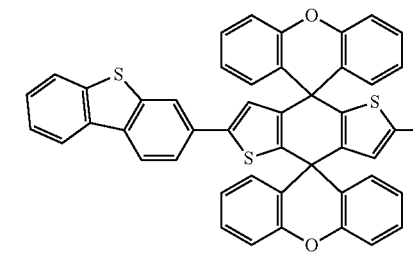
149
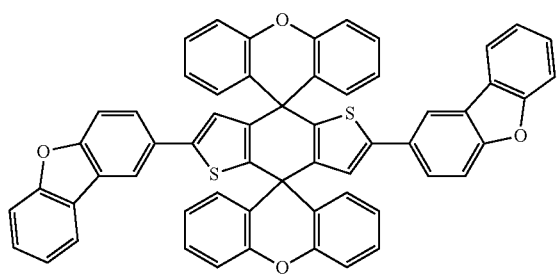
150
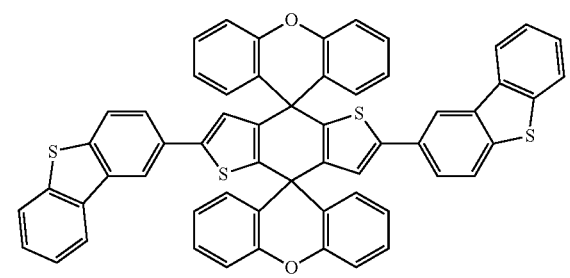
151
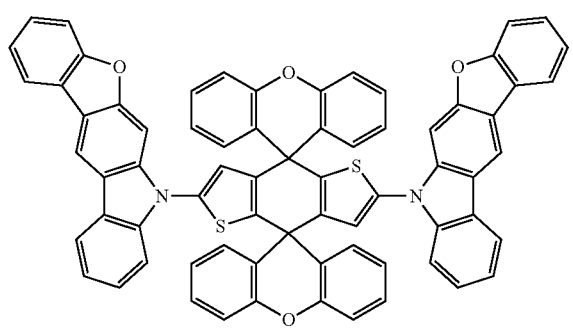
152
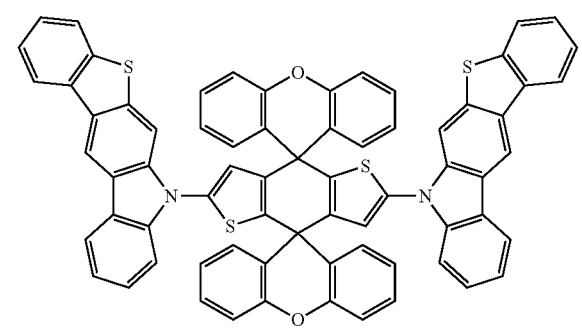
153
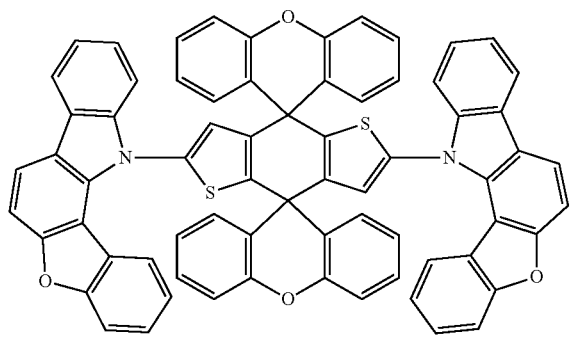
154
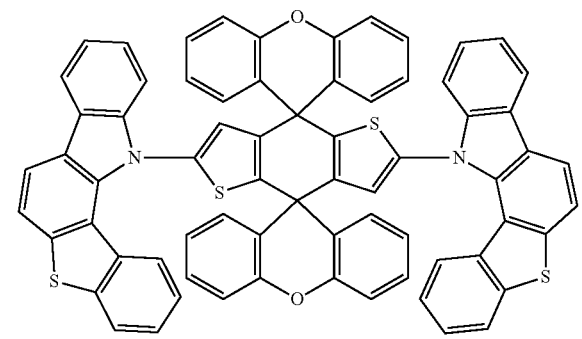

-continued
155
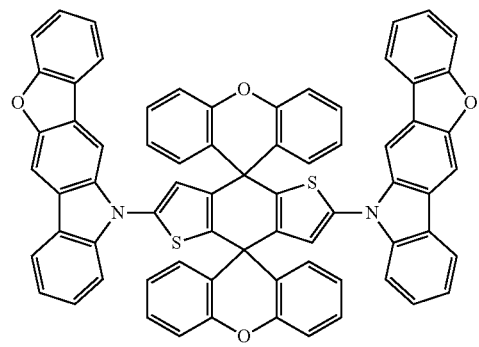
156
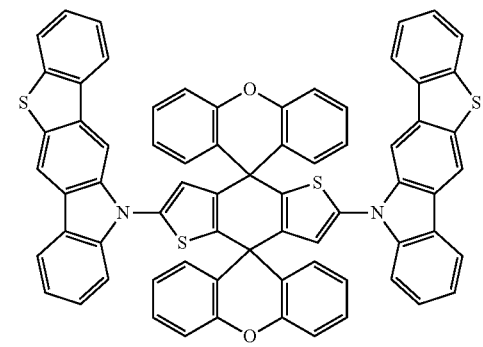
157
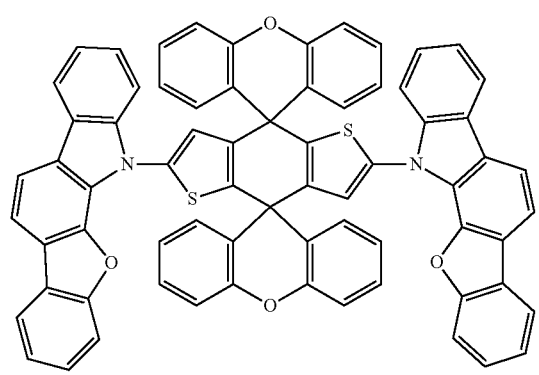
158
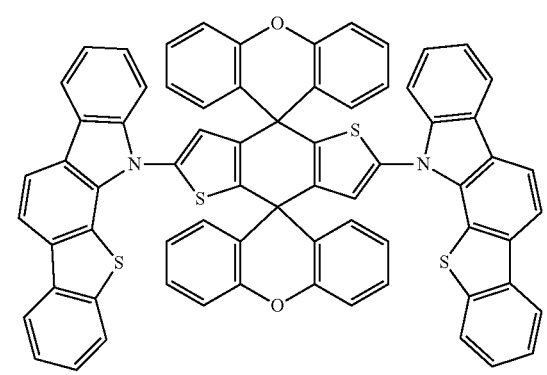
159
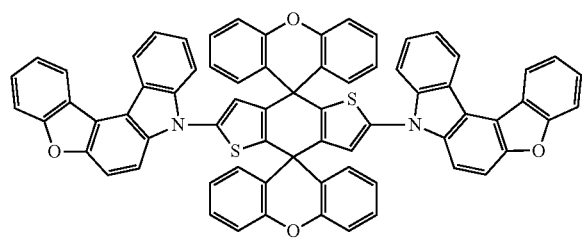
160
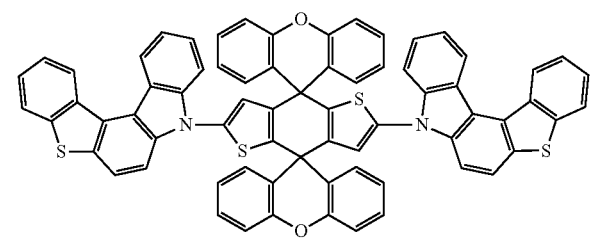
161
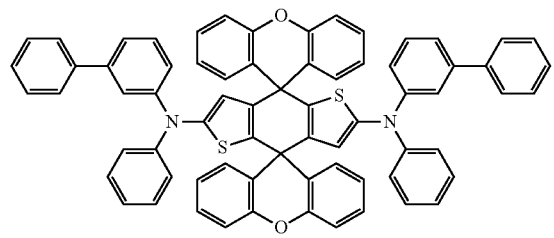
162
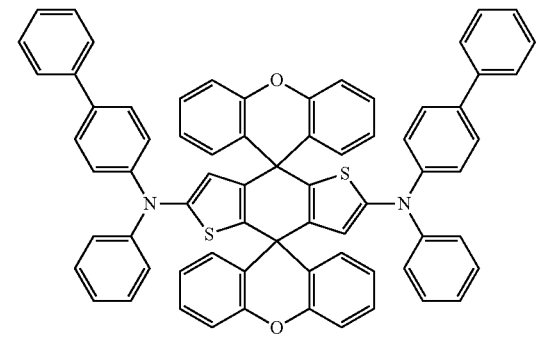

-continued
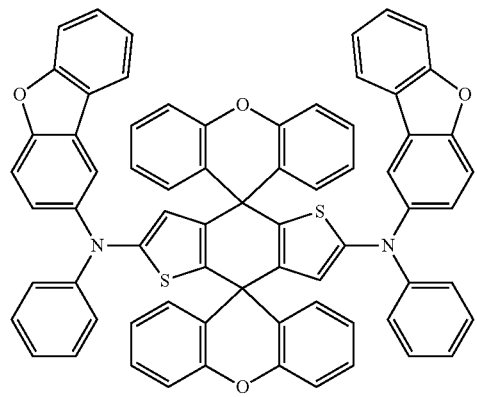
163
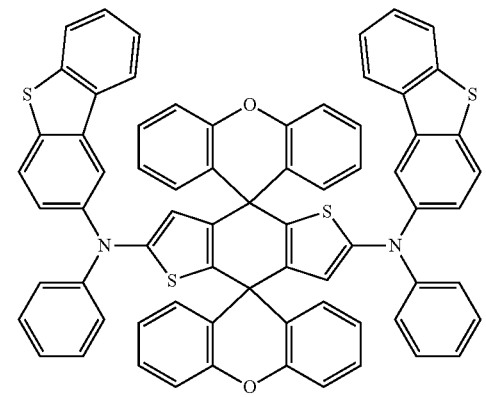
164
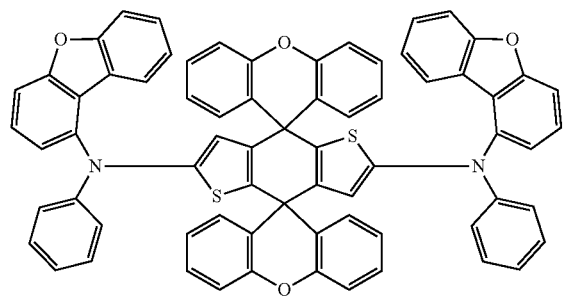
165
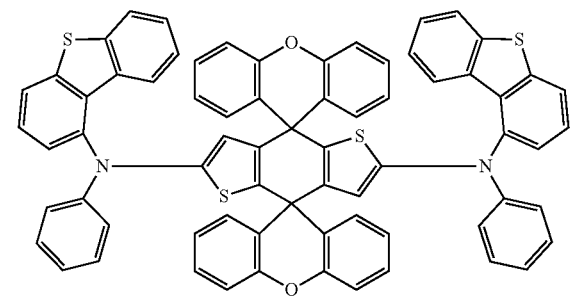
166
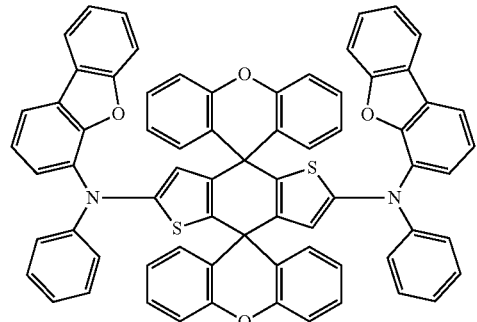
167
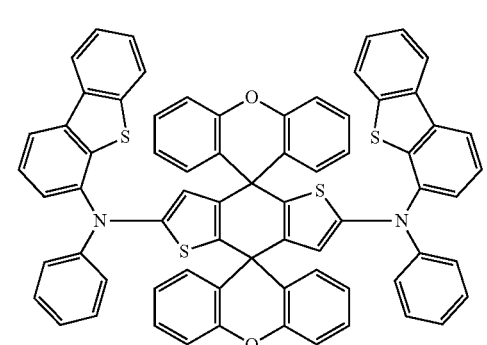
168
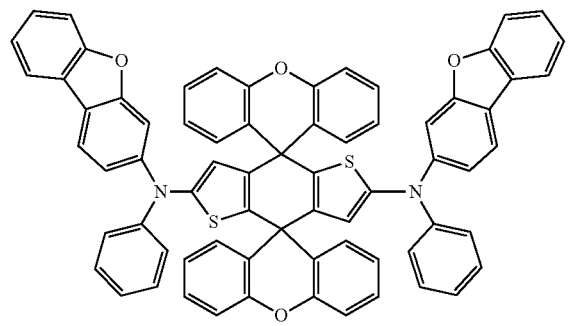
169
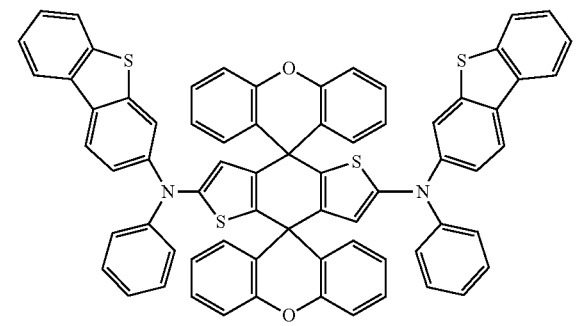
170

-continued
171 172
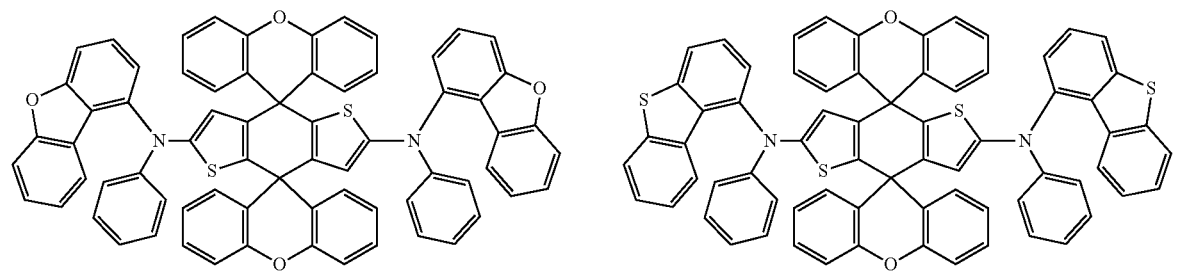
173 174
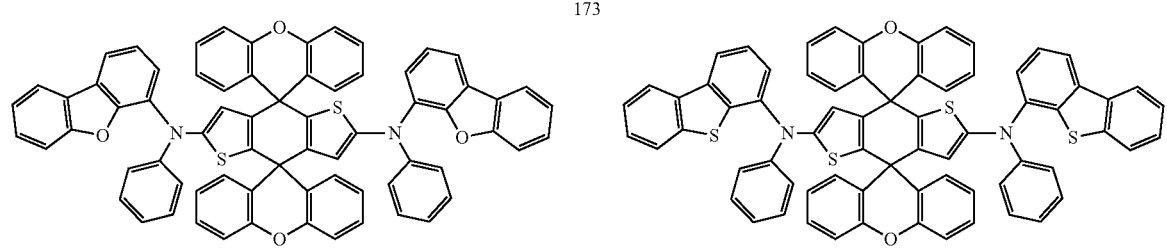
175 176
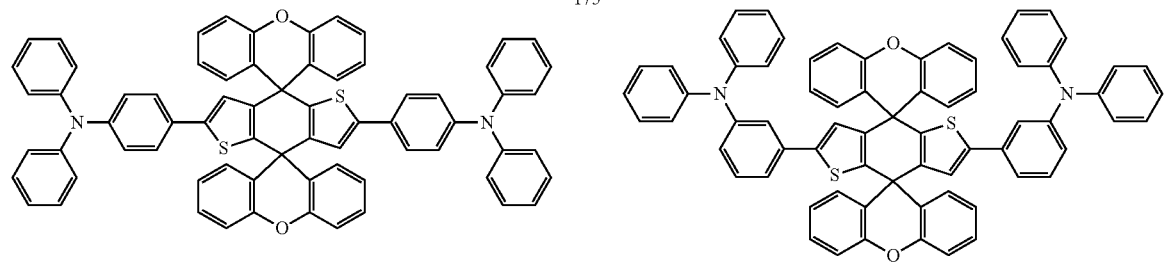
177
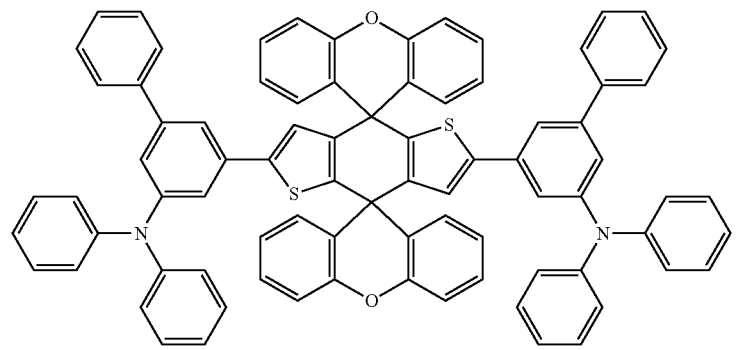
178
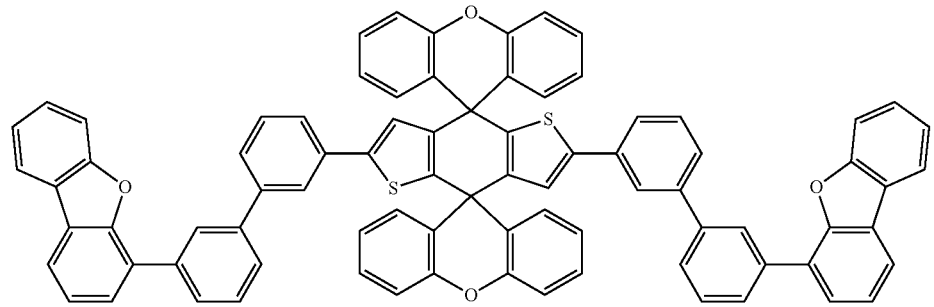

179
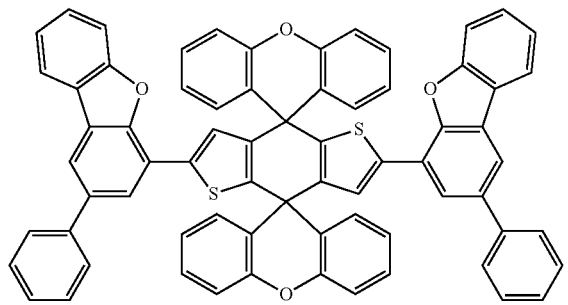
180
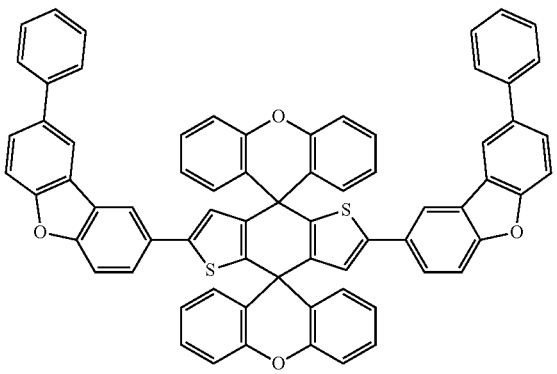
181
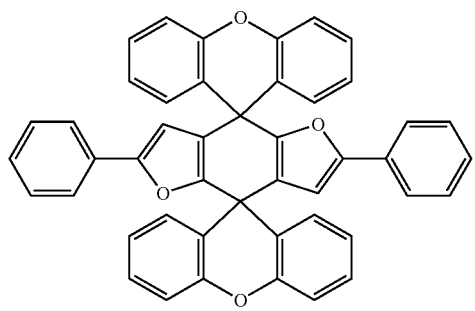
182
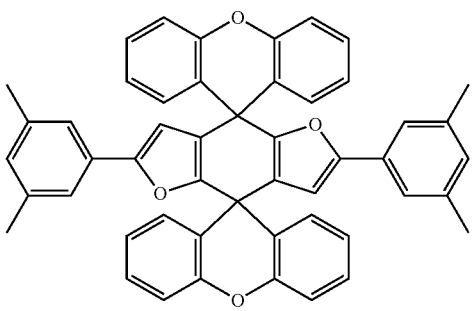
183
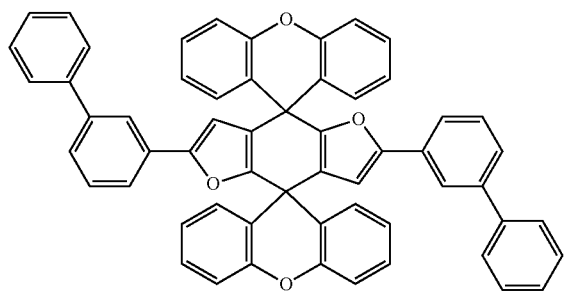
184
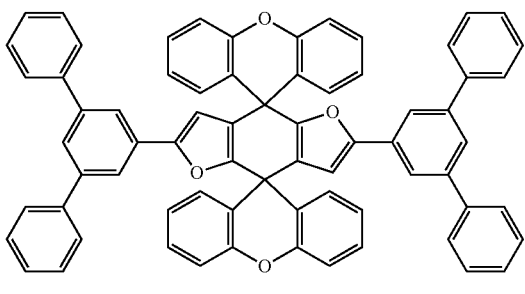
185
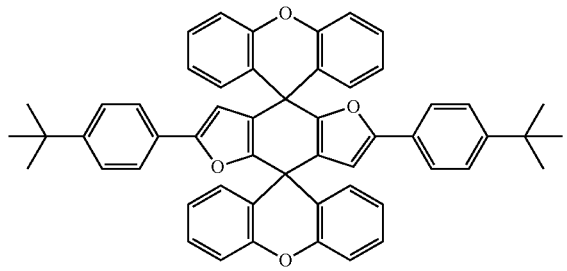
186
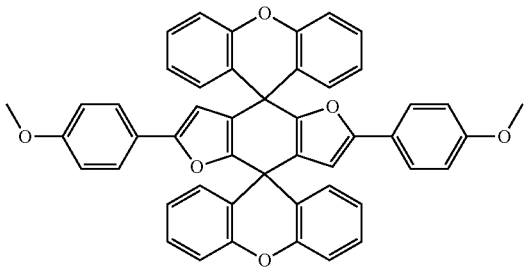
187
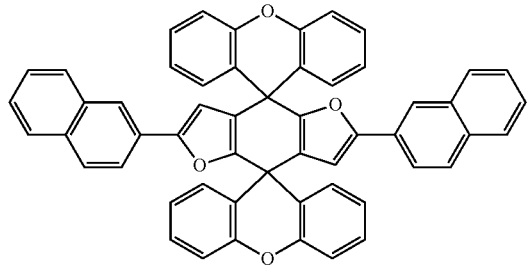
188
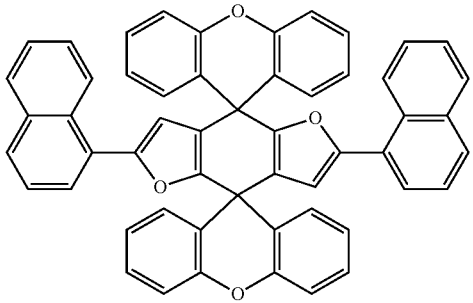

-continued
189
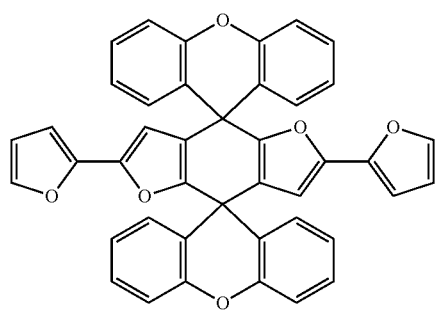
190
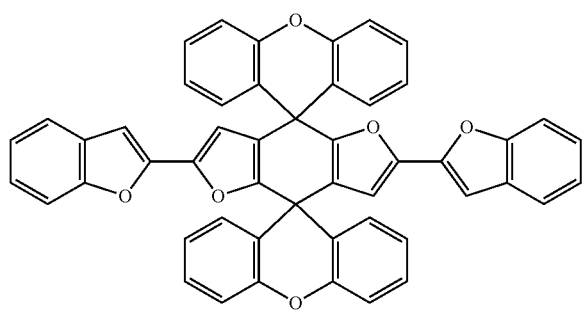
191
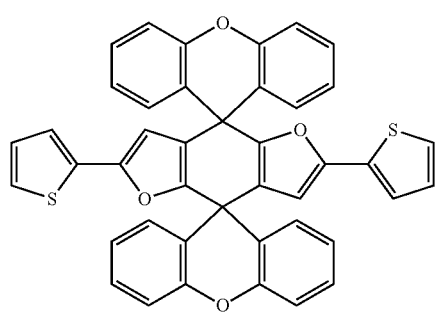
192
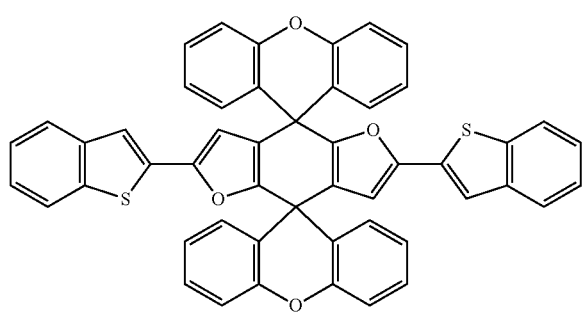
193
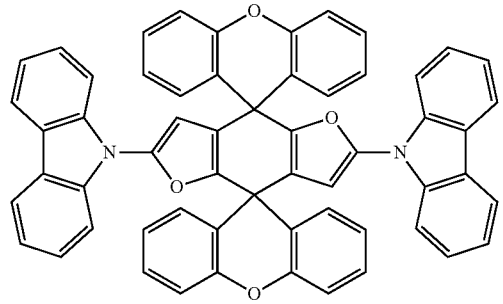
194
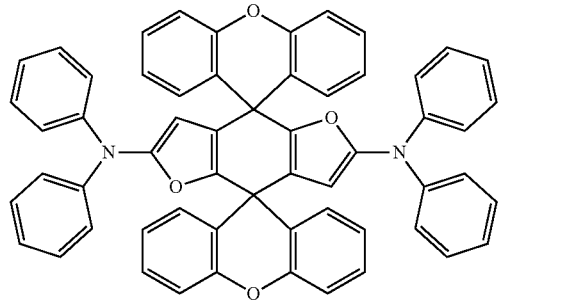
195
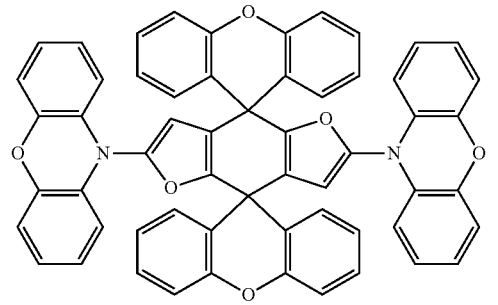
196
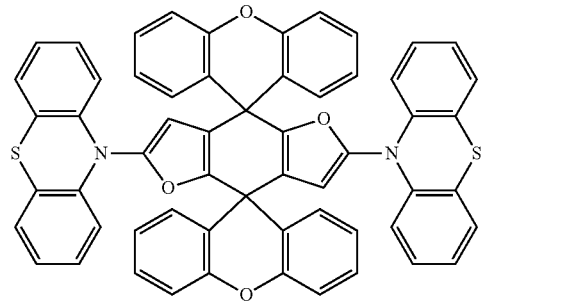
197
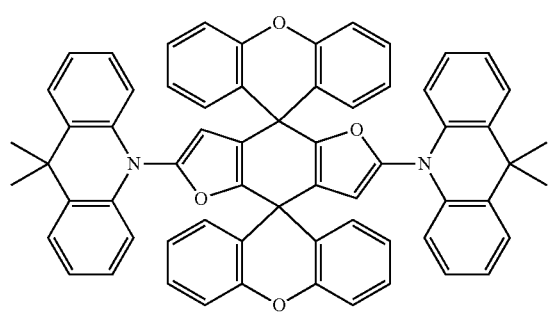
198
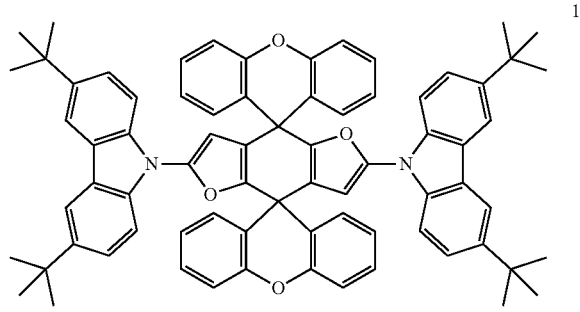

-continued
199
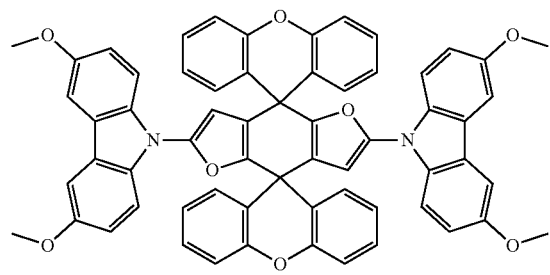
200
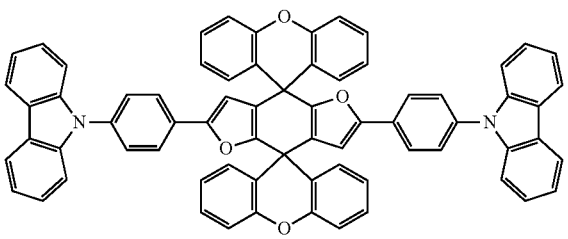
201
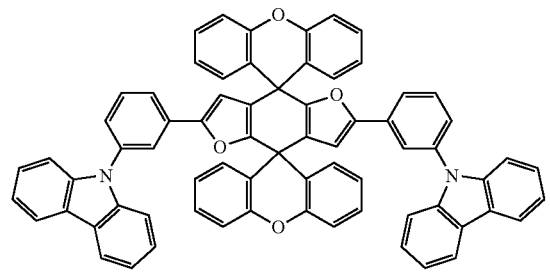
202
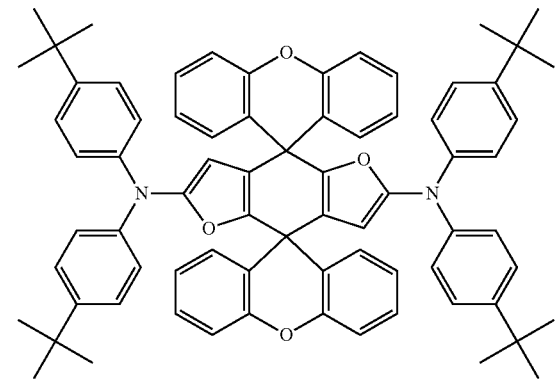
203
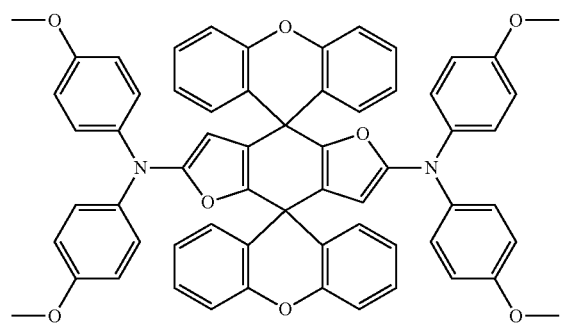
204
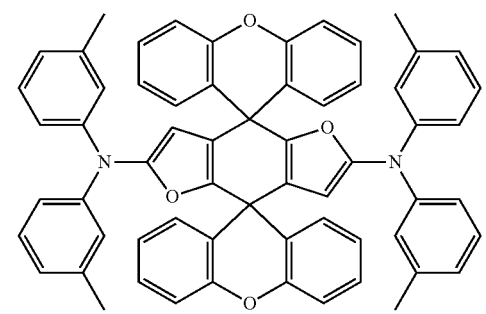
205
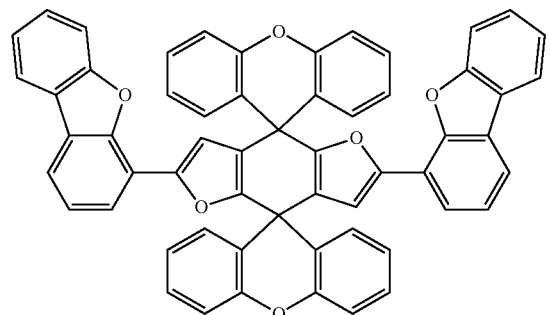
206
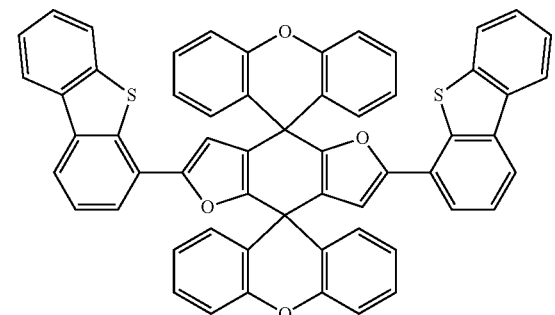
207
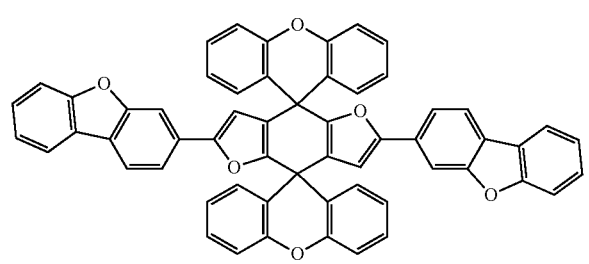
208
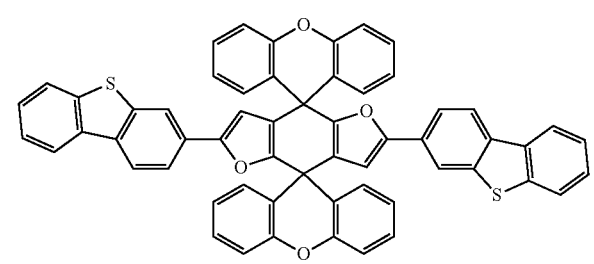

-continued
| 209 | 210 |
|---|---|
| 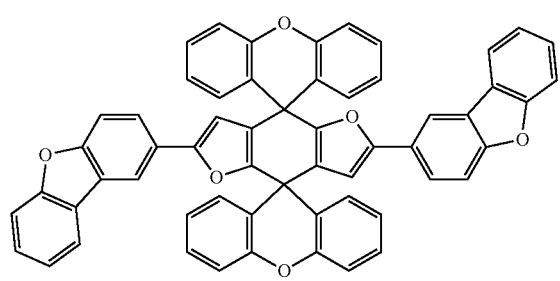 | 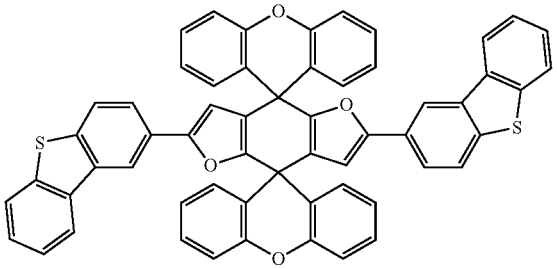 |
| 211 | 212 |
| 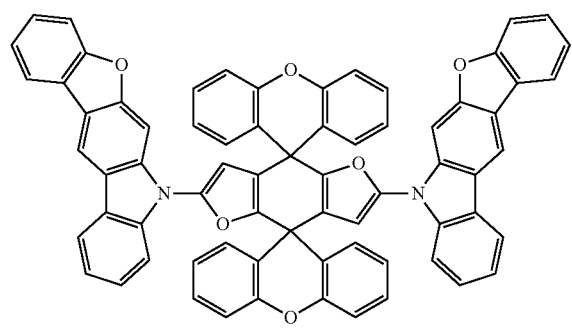 | 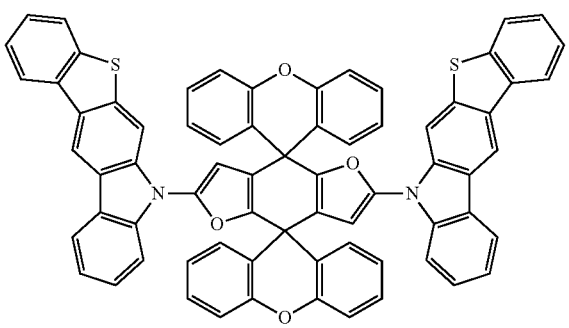 |
| 213 | 214 |
| 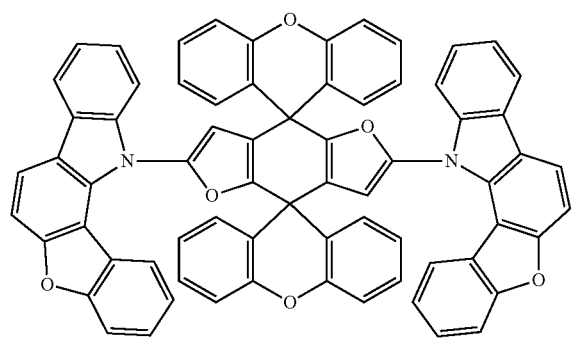 | 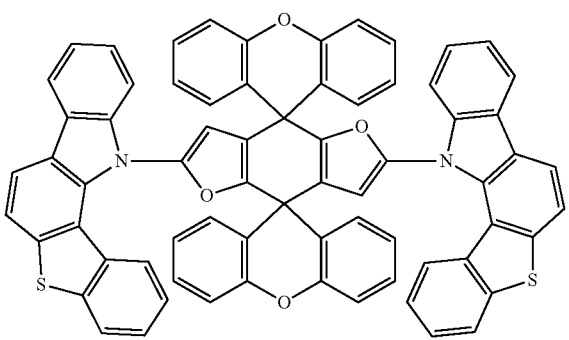 |
| 215 | 216 |
| 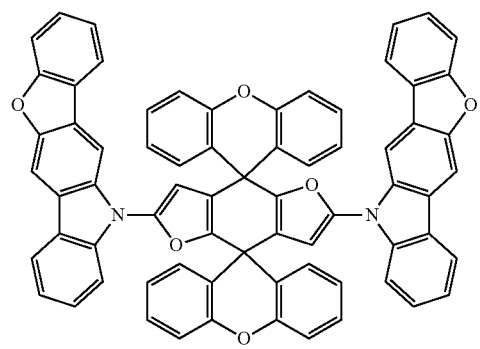 | 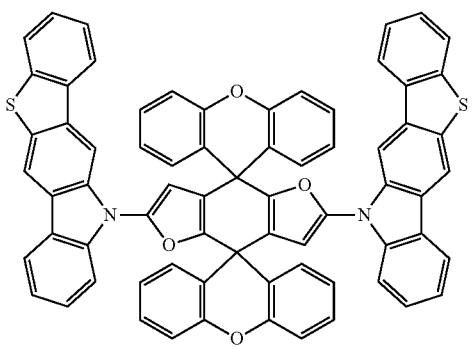 |

-continued
217
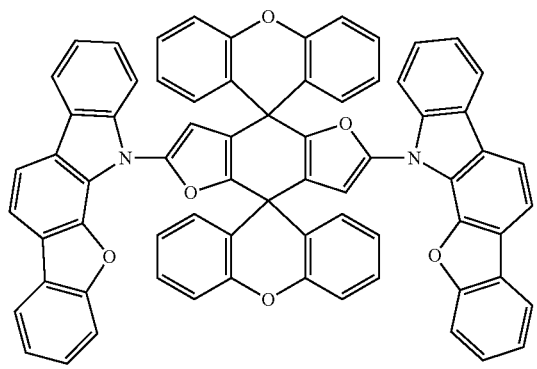
218
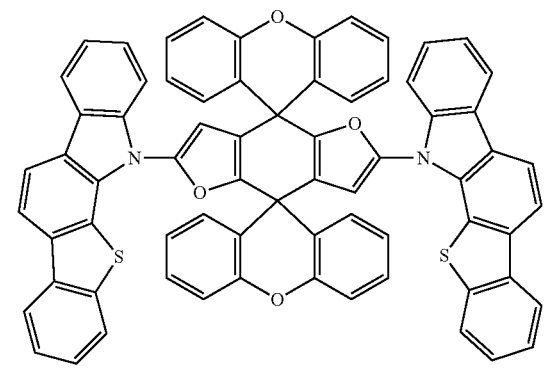
219
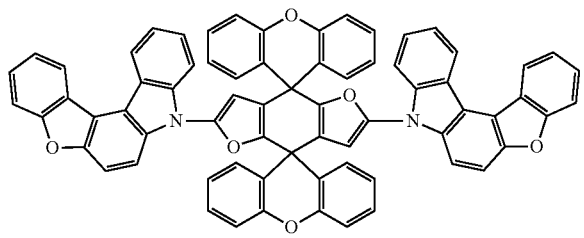
220
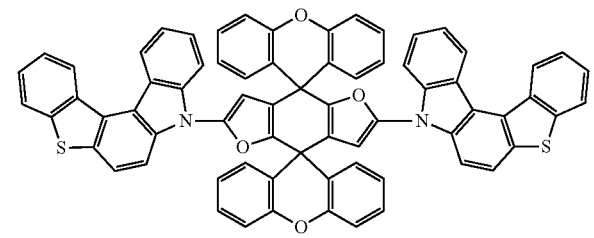
221
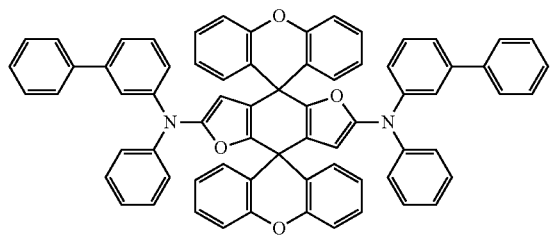
222
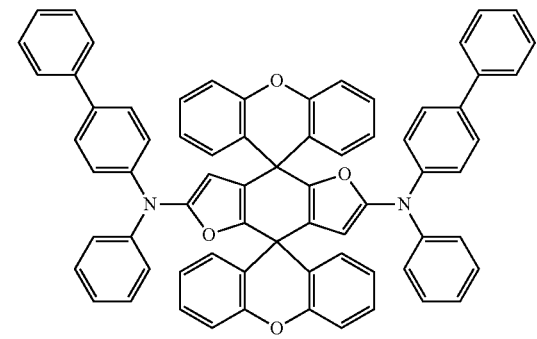
223
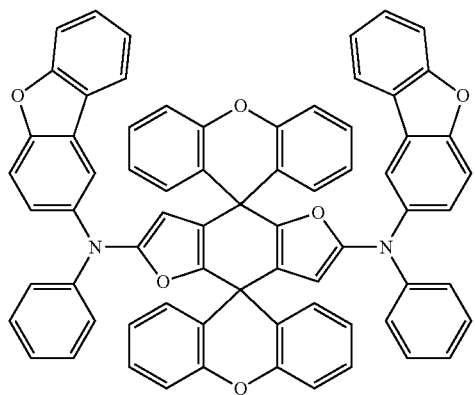
224
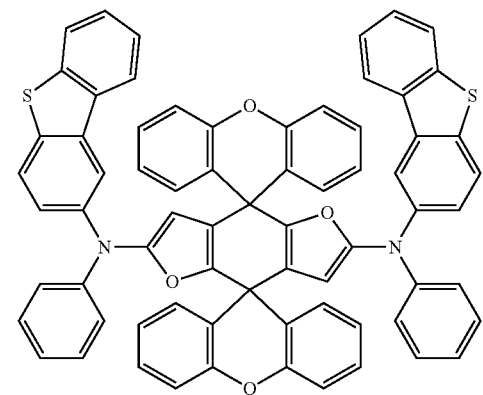

-continued
225
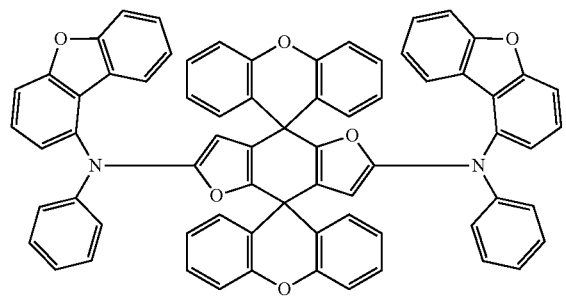
226
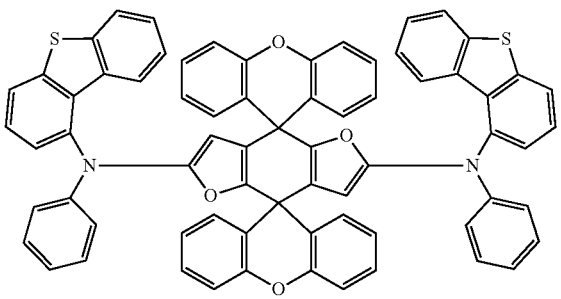
227
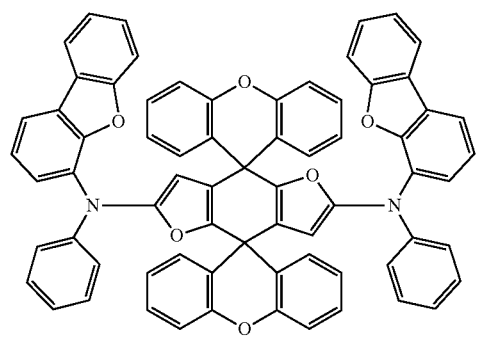
228
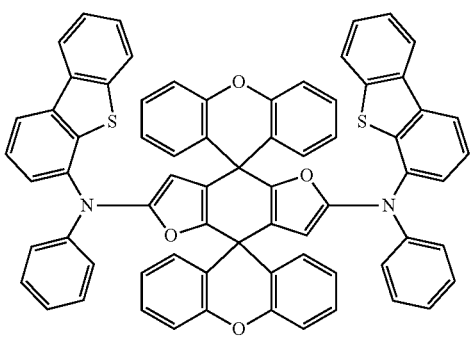
229
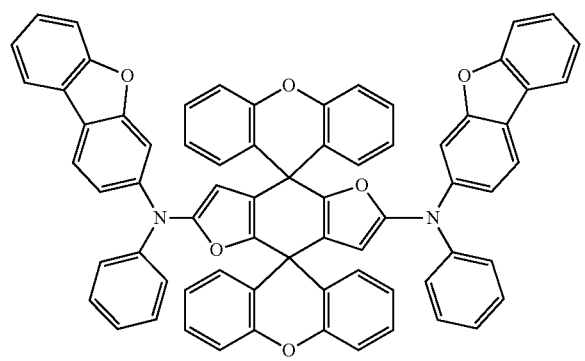
230
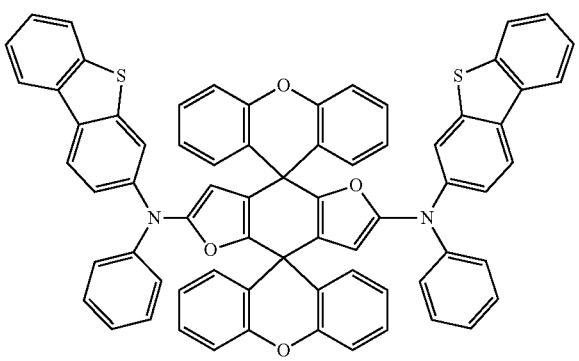
231
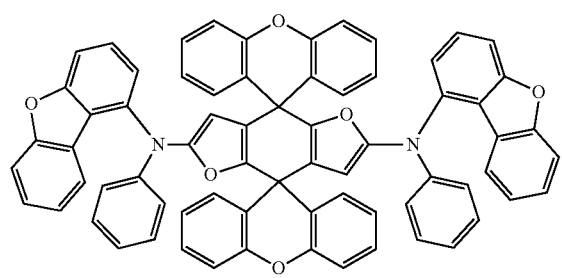
232
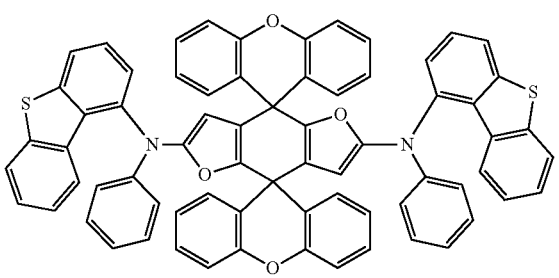
233
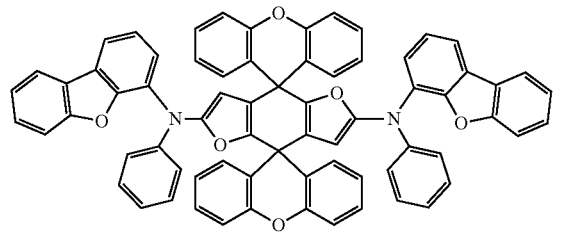
234
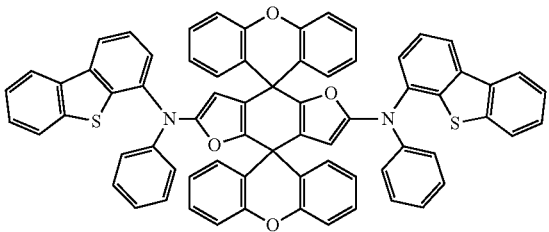

235
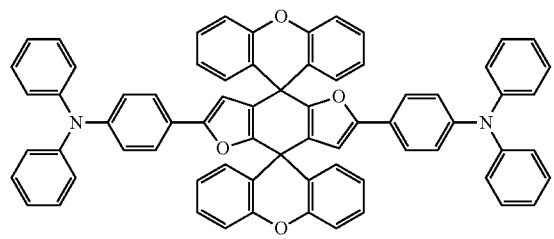
236
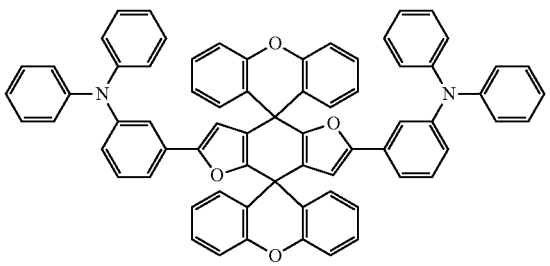
237
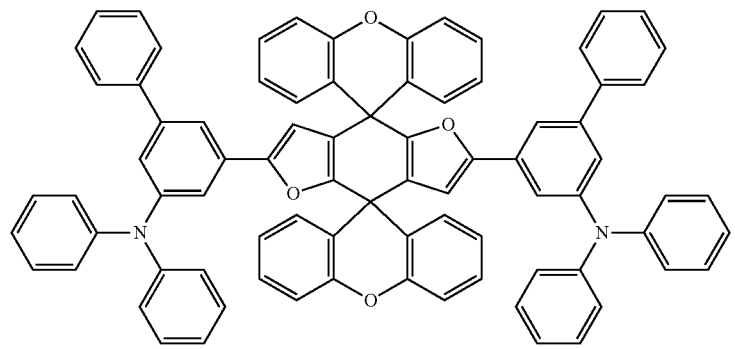
238
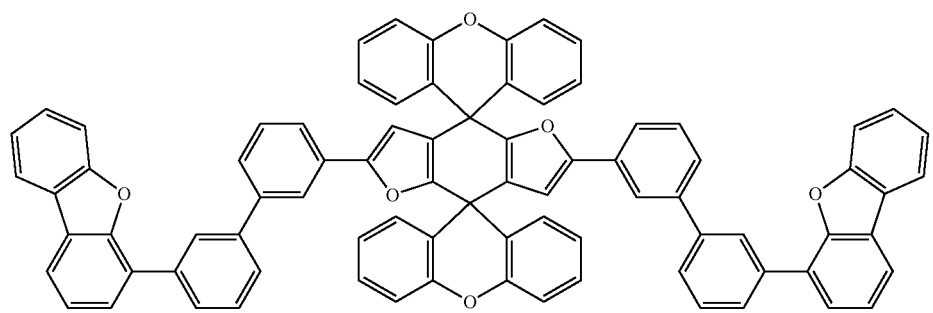
239
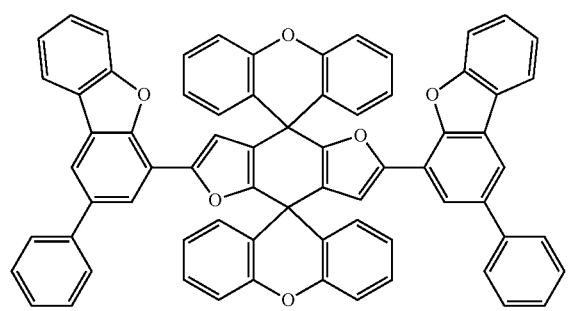
240
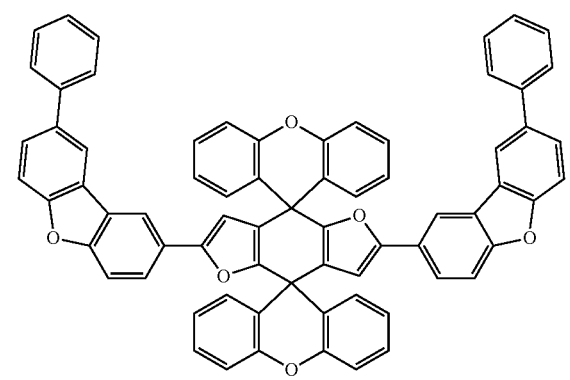
241
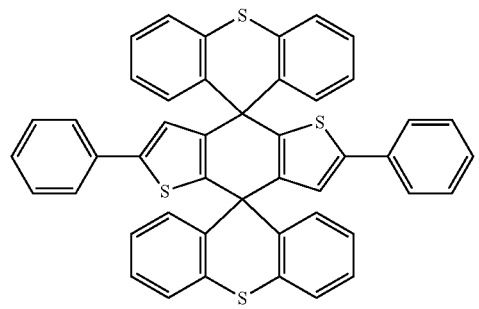
242
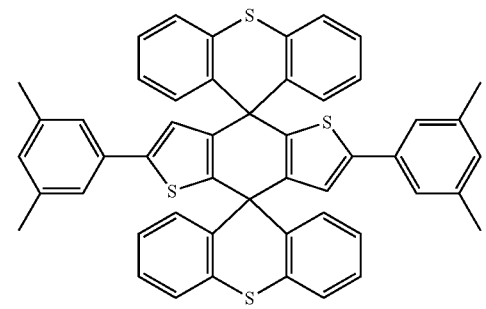

-continued
| 243 | 244 |
|---|---|
| 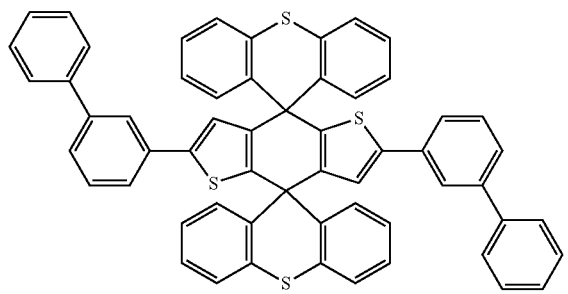 | 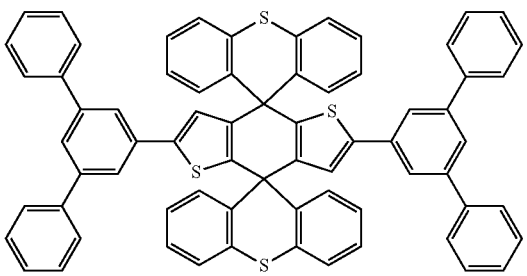 |
| 245 | 246 |
| 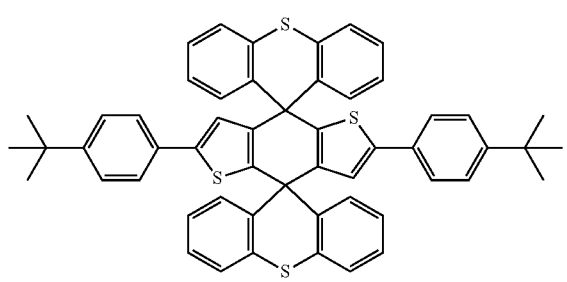 | 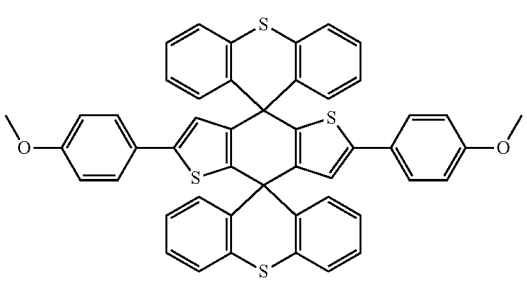 |
| 247 | 248 |
| 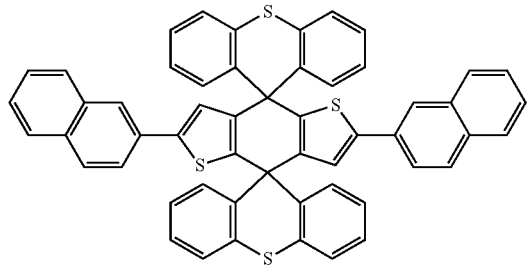 | 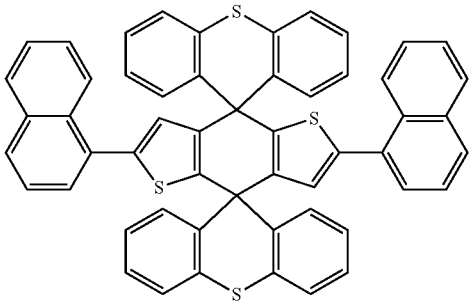 |
| 249 | 250 |
| 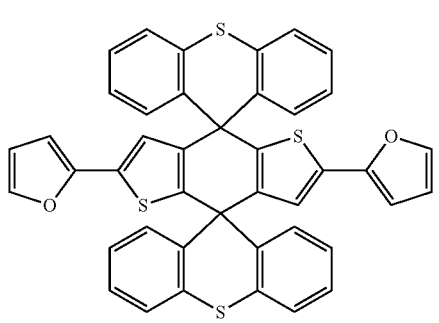 | 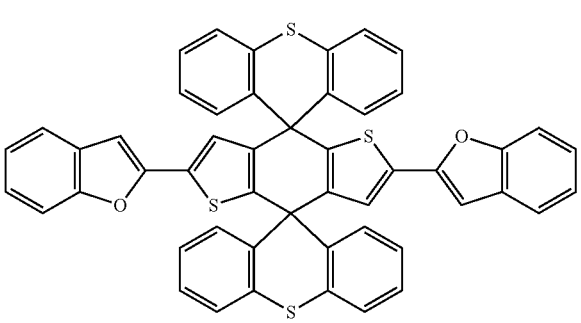 |
| 251 | 252 |
| 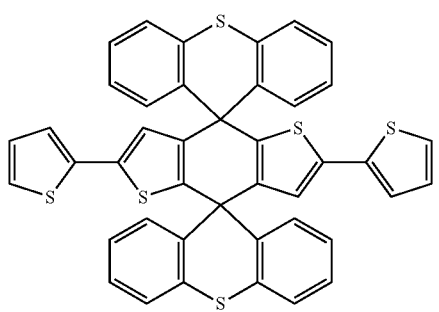 | 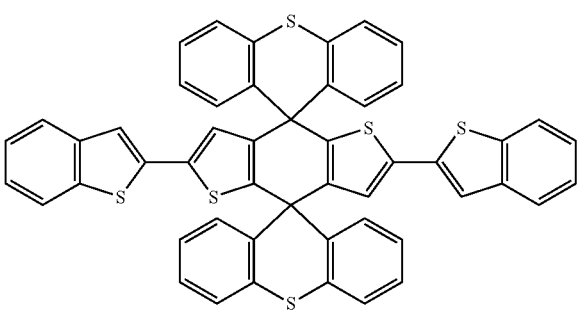 |

-continued
253 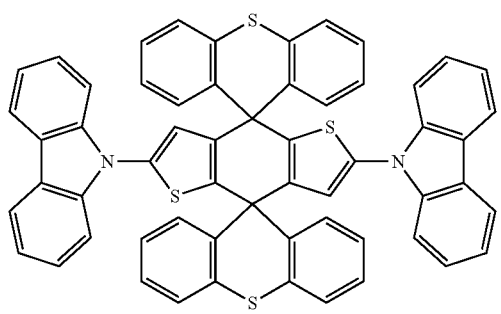
254 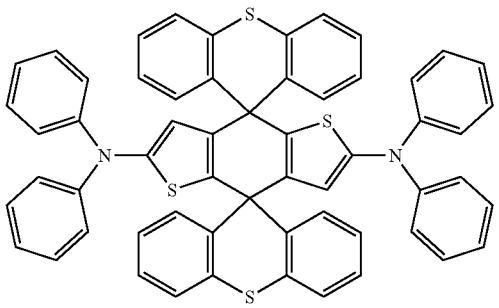
255 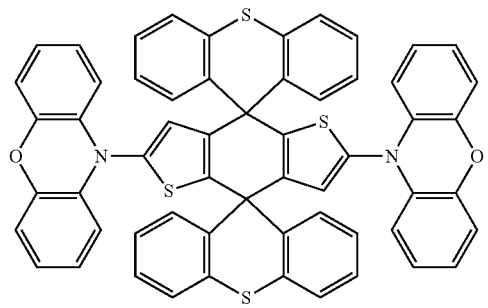
256 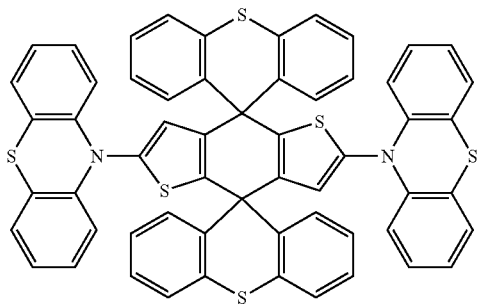
257 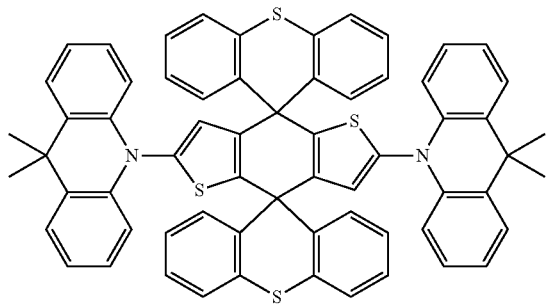
258 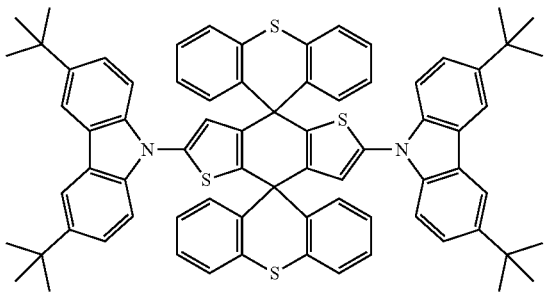
259 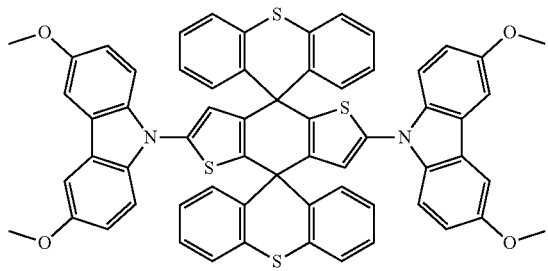
260 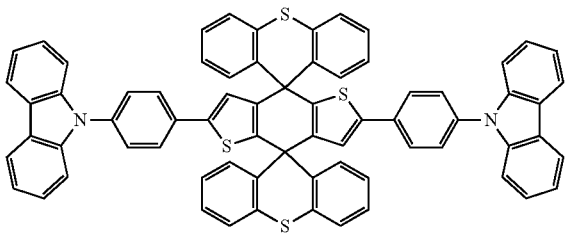
261 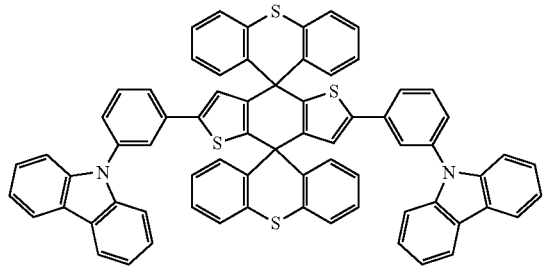
262 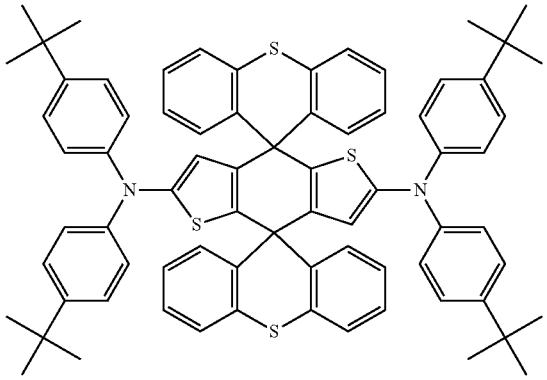

-continued
263
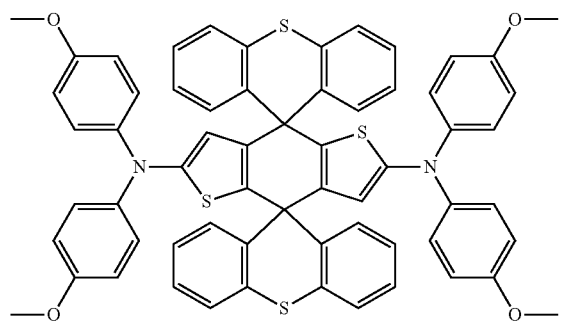
264
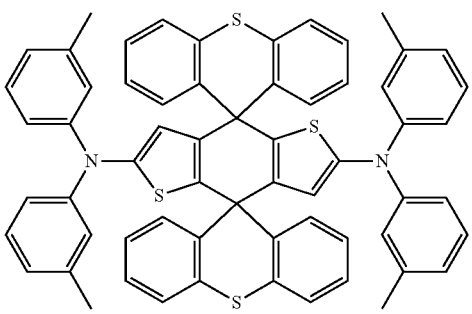
265
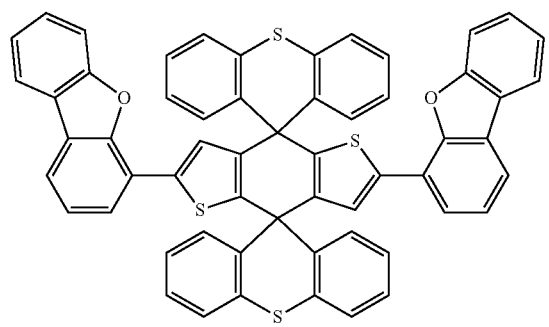
266
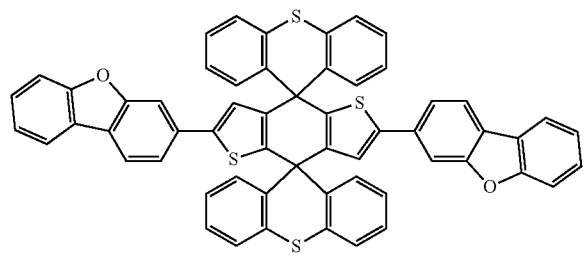
267
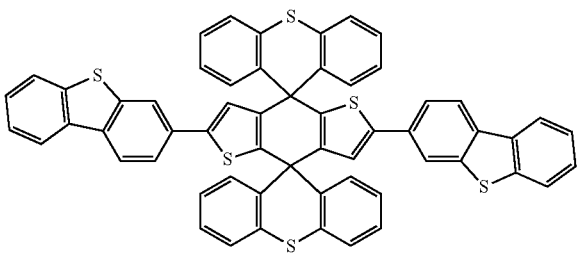
268
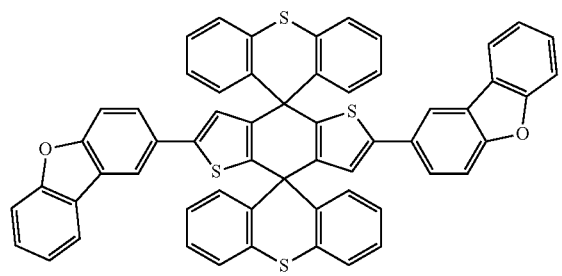
269
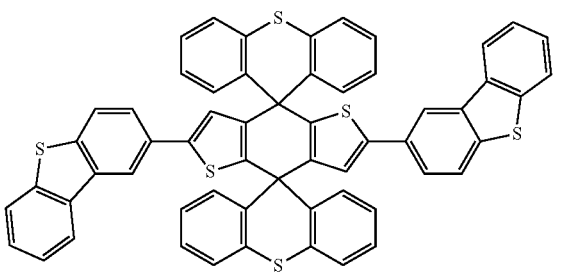
270
271
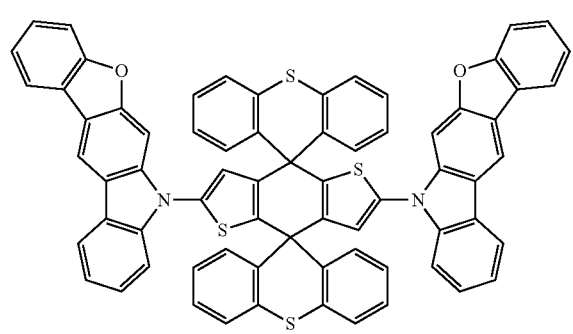
272
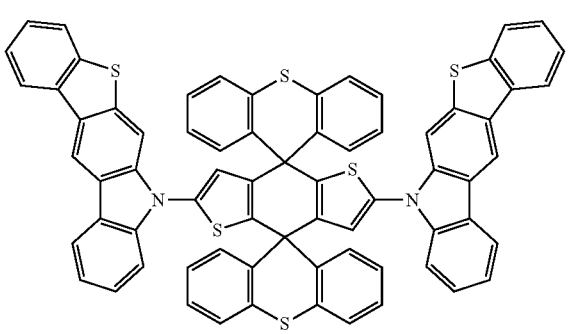

273
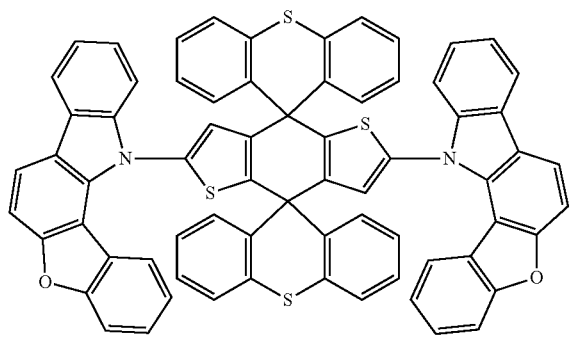
274
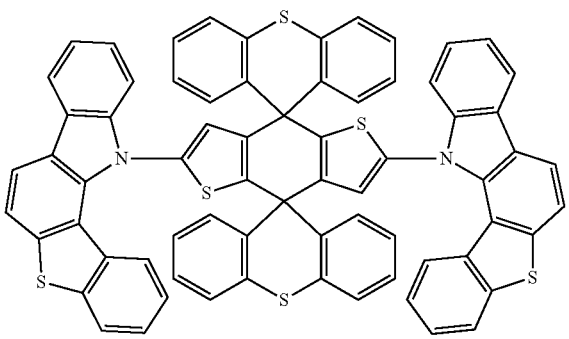
275
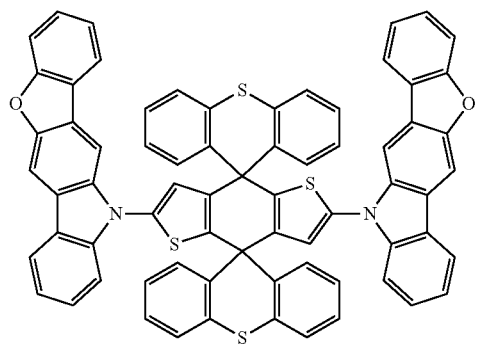
276
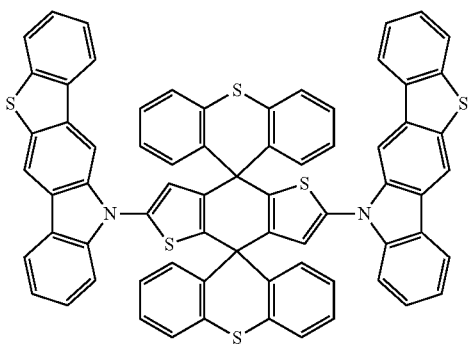
277
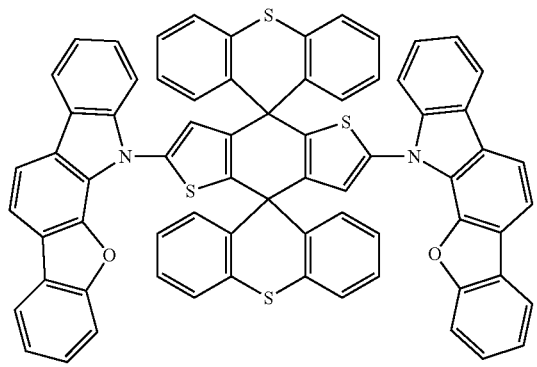
278
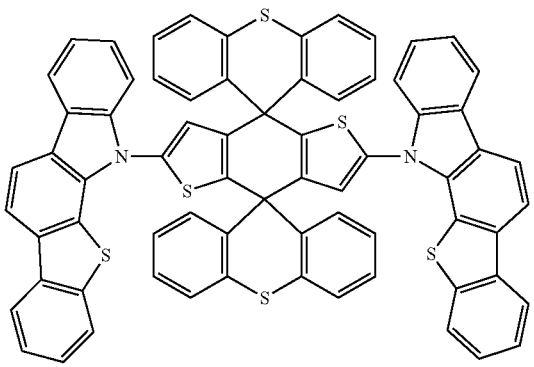
279
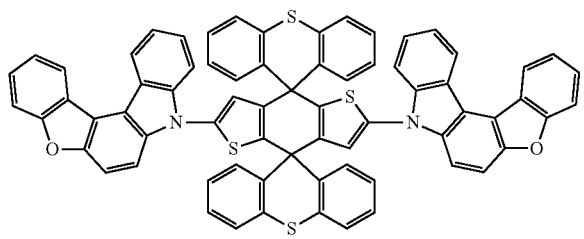
280
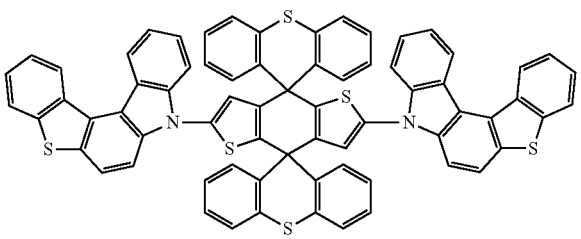

93
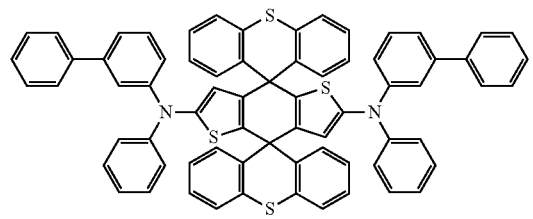
281
94
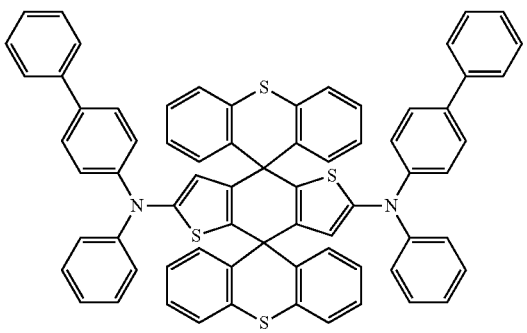
282
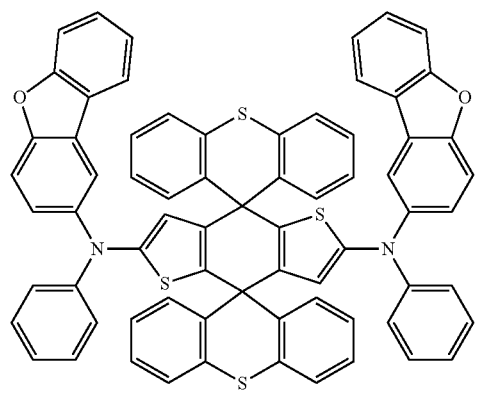
283
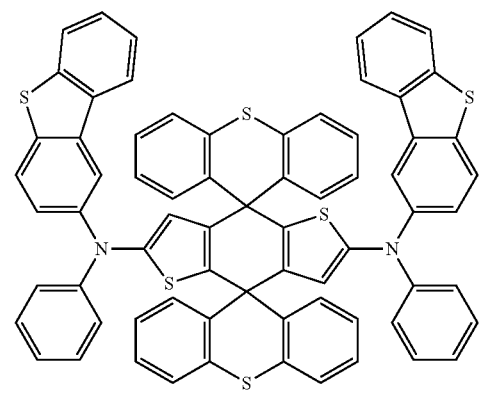
284
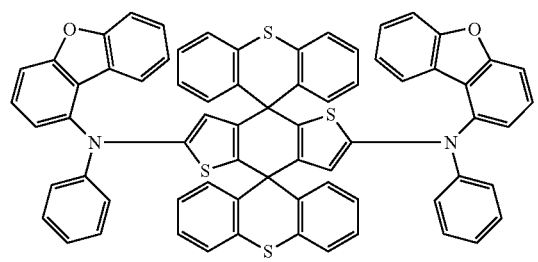
285
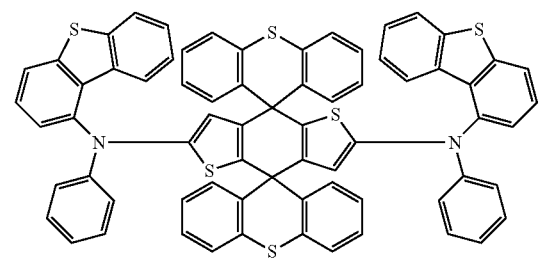
286
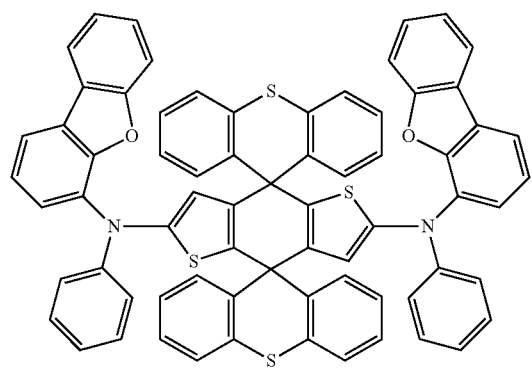
287
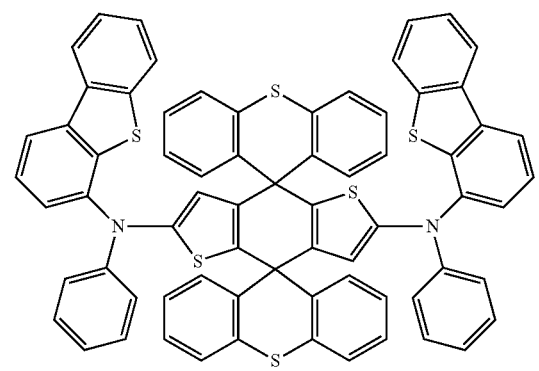
288

-continued
289
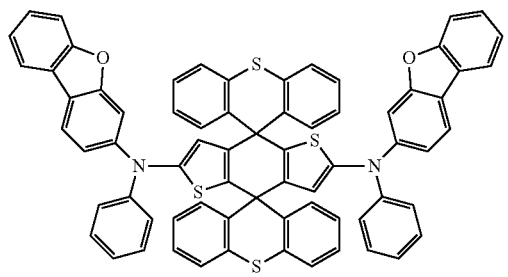
290
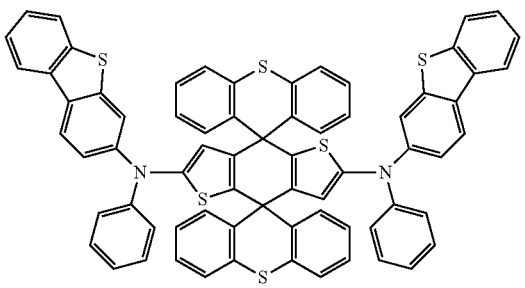
291
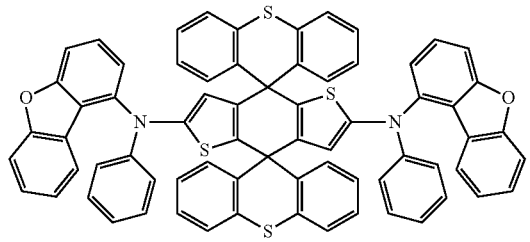
292
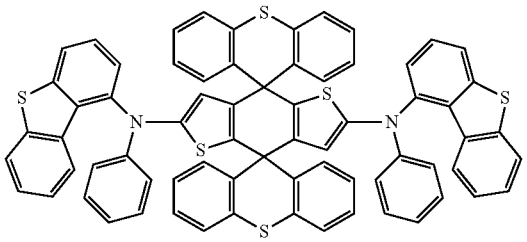
293
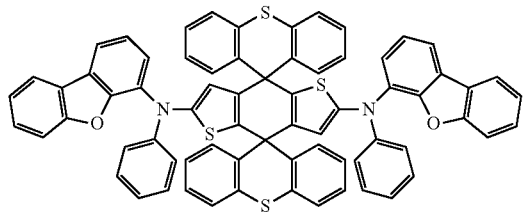
294
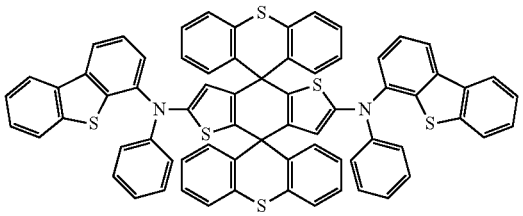
295
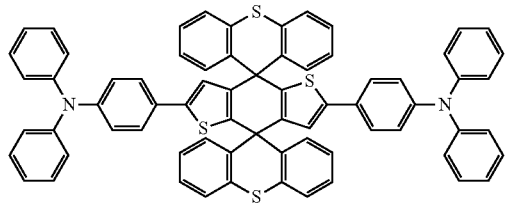
296
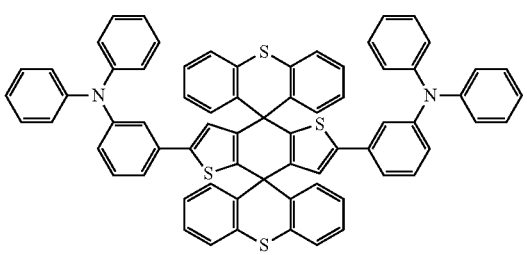
297
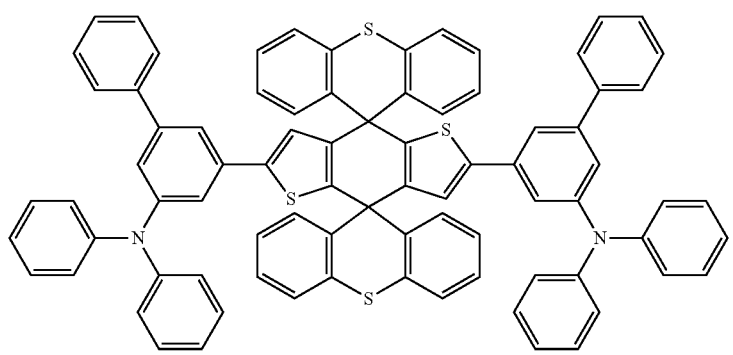

-continued
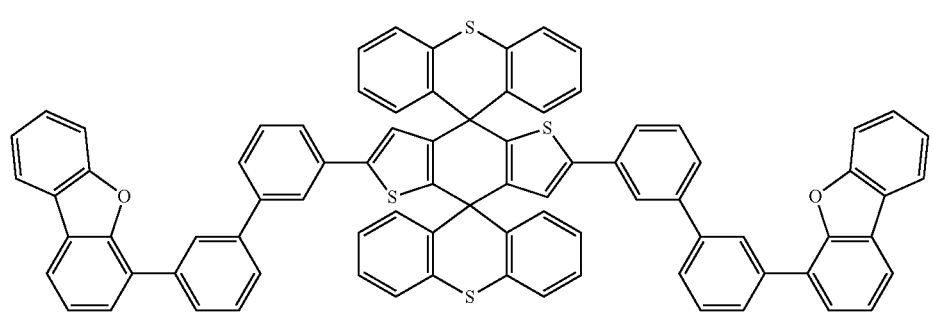
298
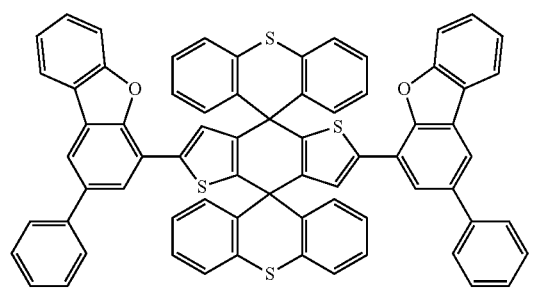
299
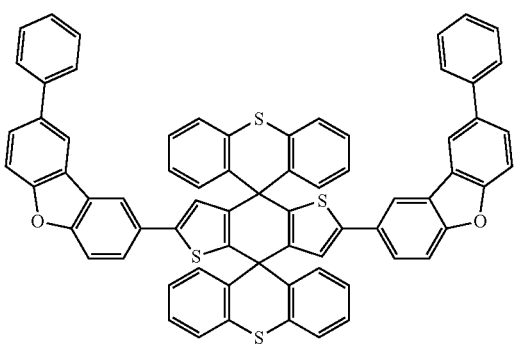
300
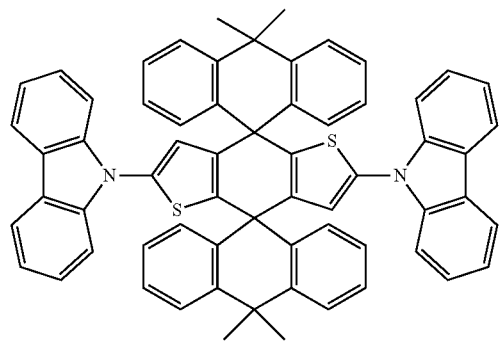
301
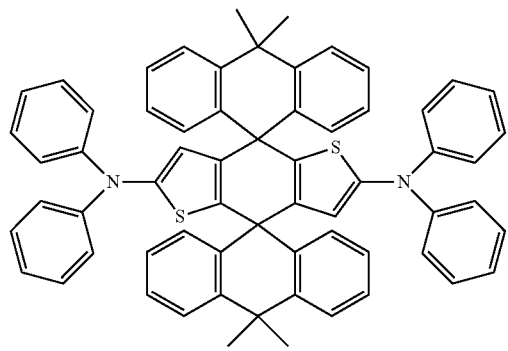
302
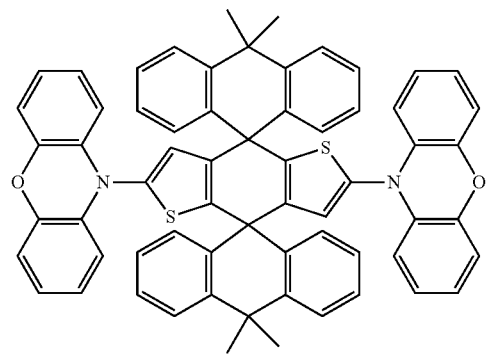
303
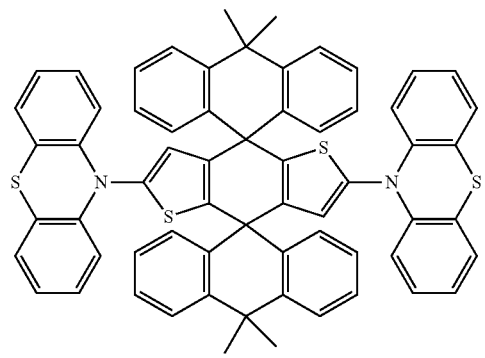
304

305
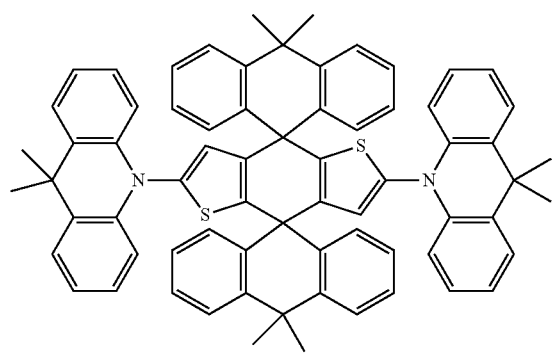
306
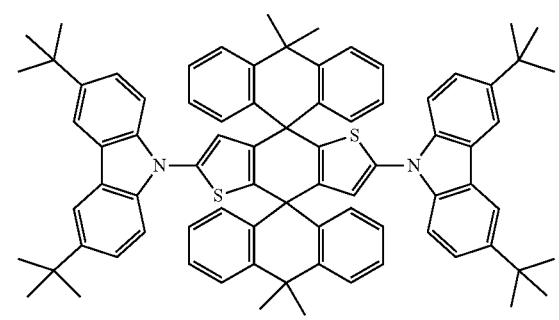
307
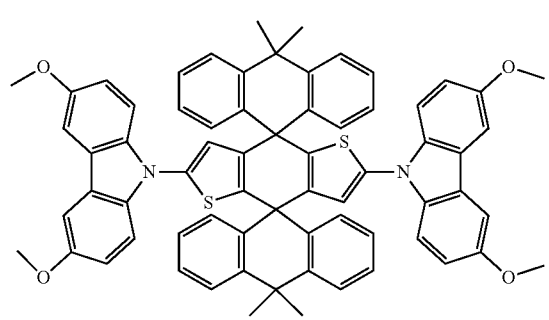
308
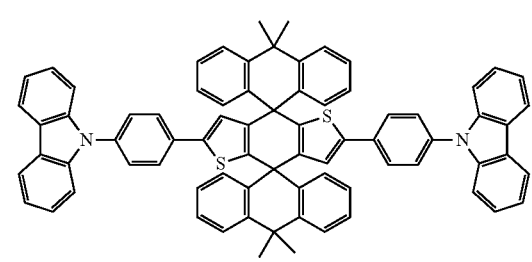
309
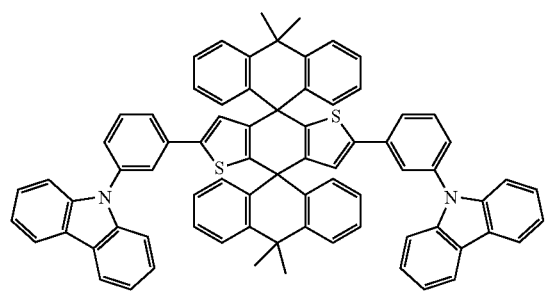
310
311
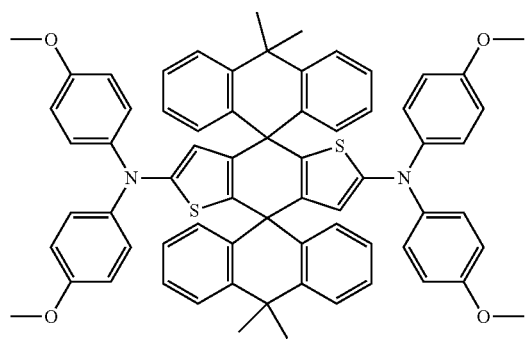
312
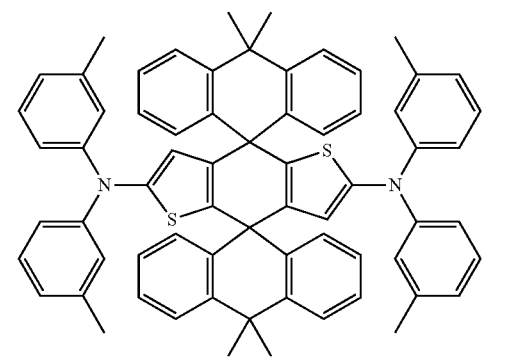

-continued
313
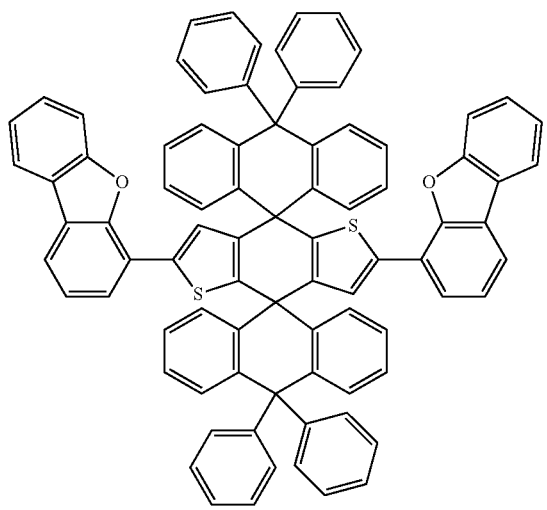
314
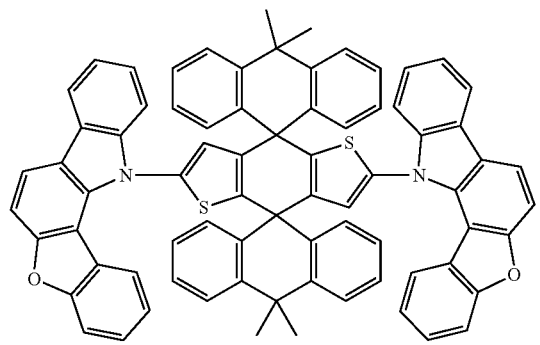
315
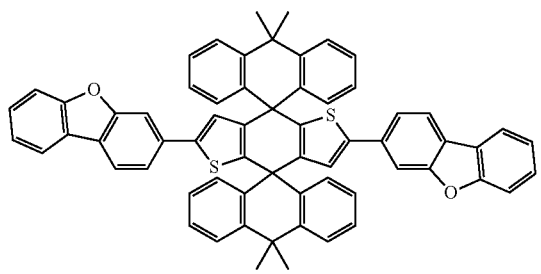
316
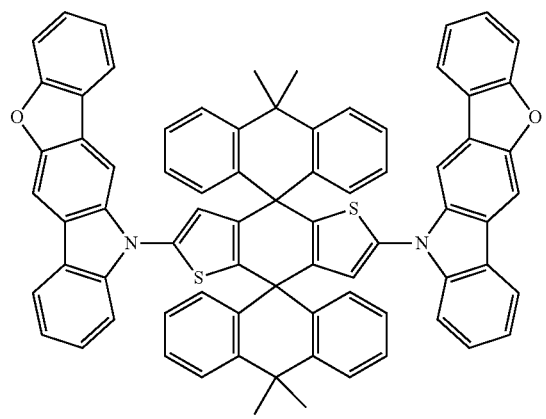
317
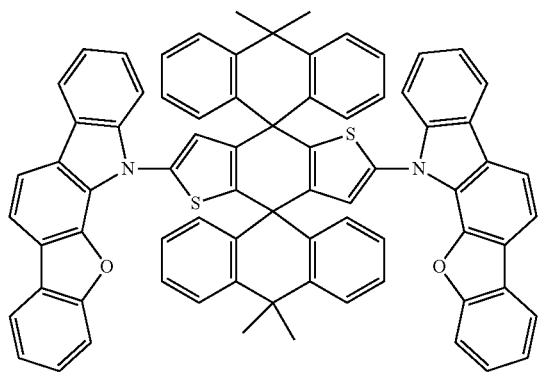
318
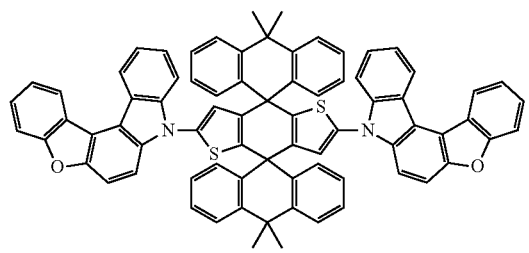
319
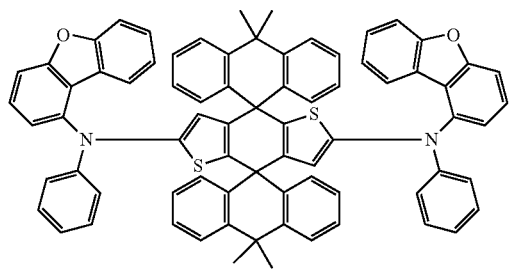
320
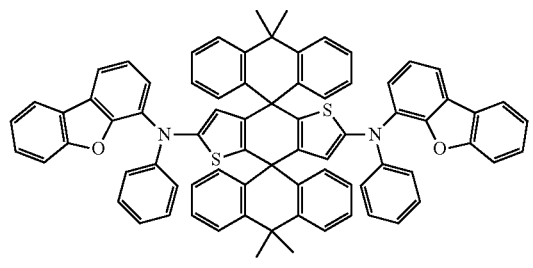

321 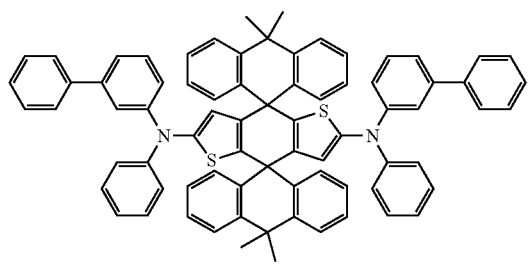
322 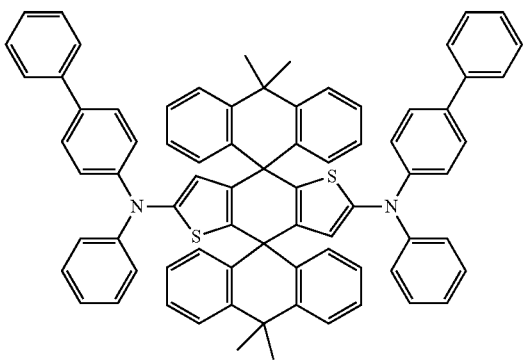
323 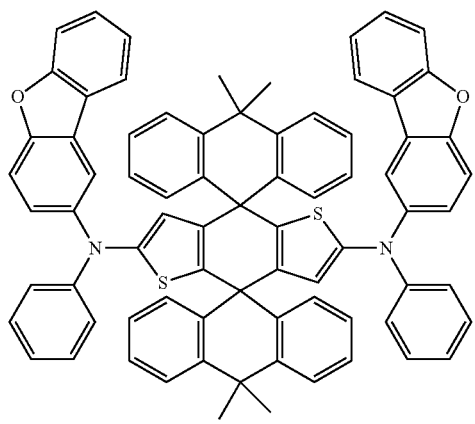
324 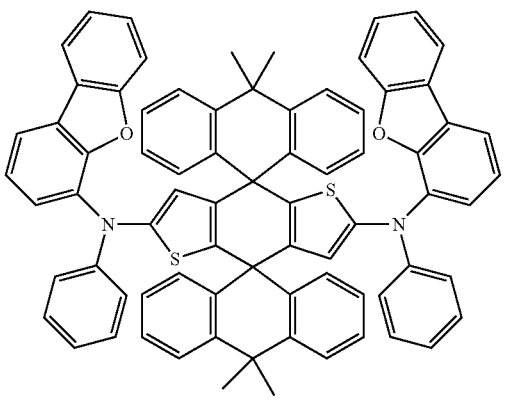
325 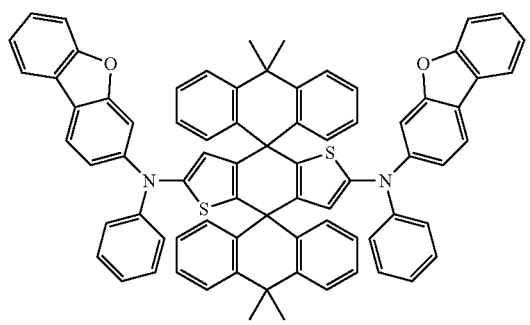
326 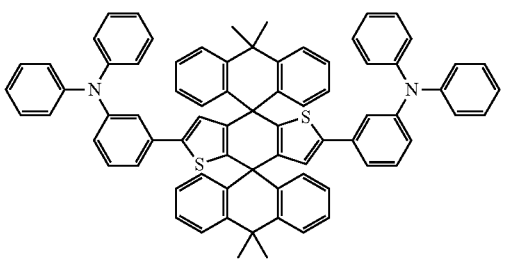
327 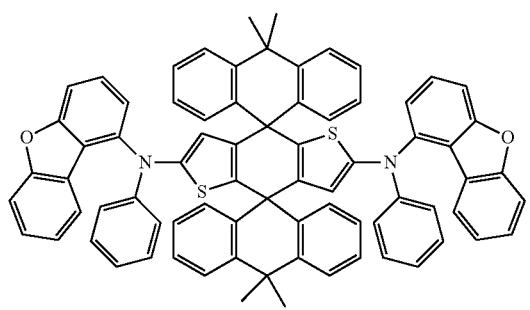
328 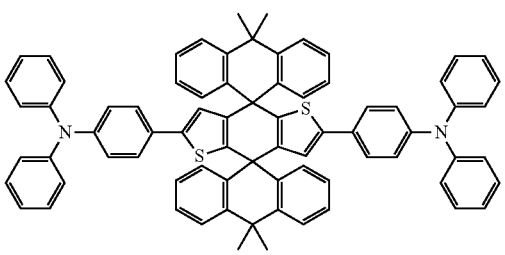

-continued
329
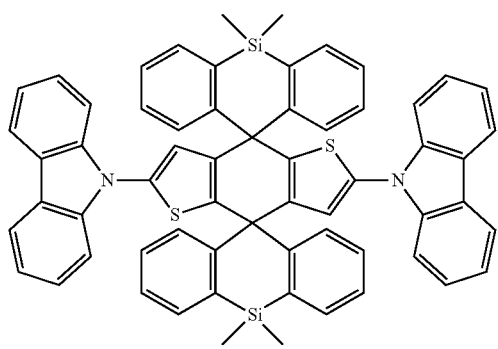
330
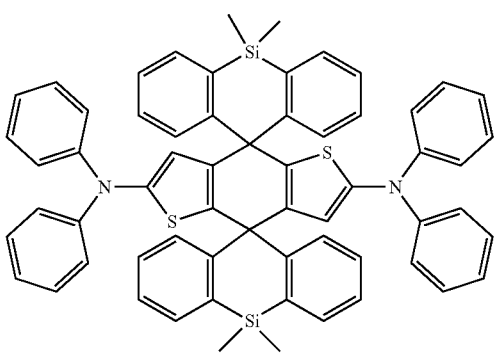
331
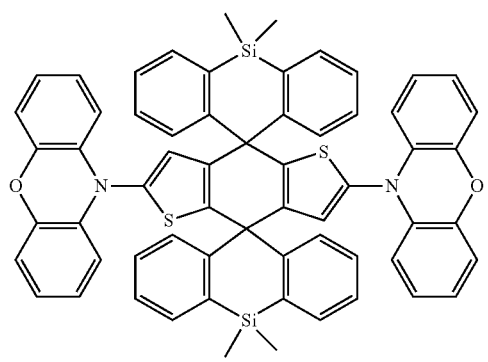
332
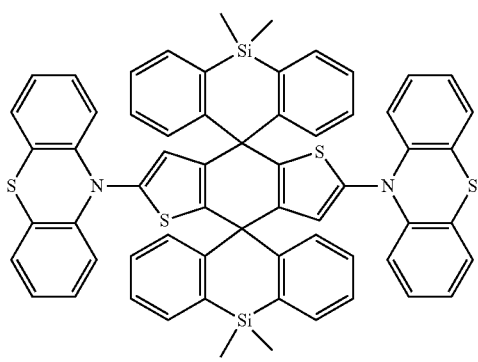
333
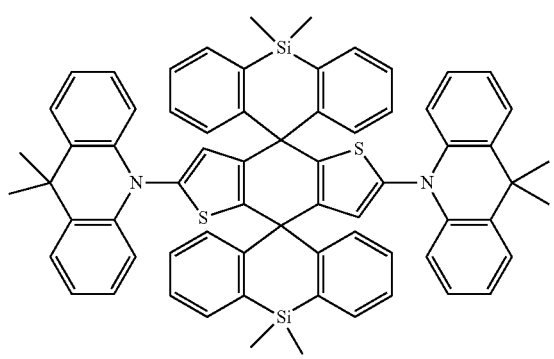
334
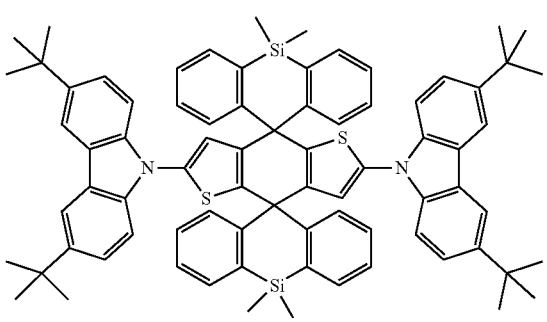
335
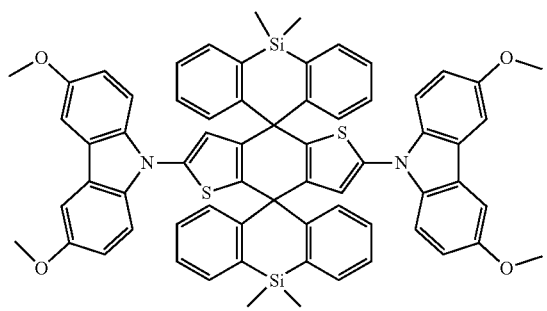
336
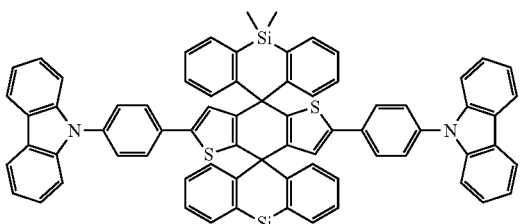

-continued
337
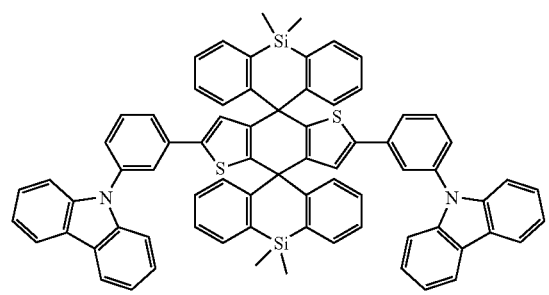
338
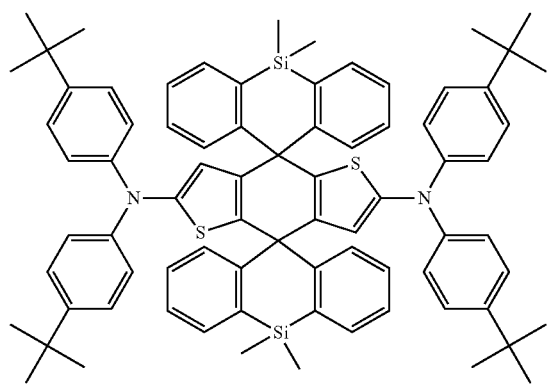
339
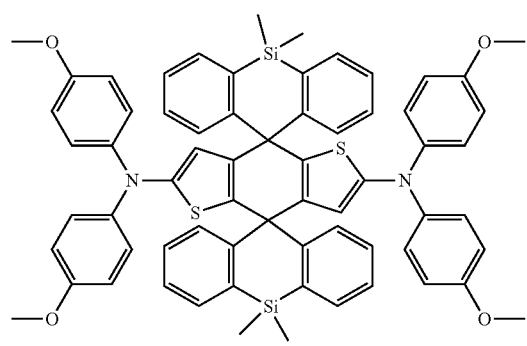
340
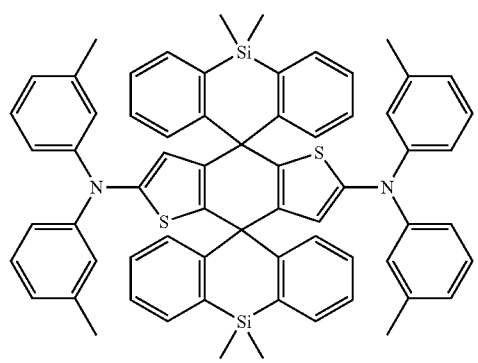
341
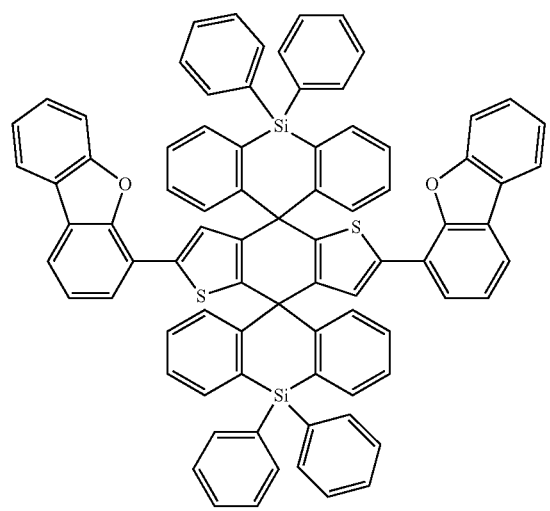
342
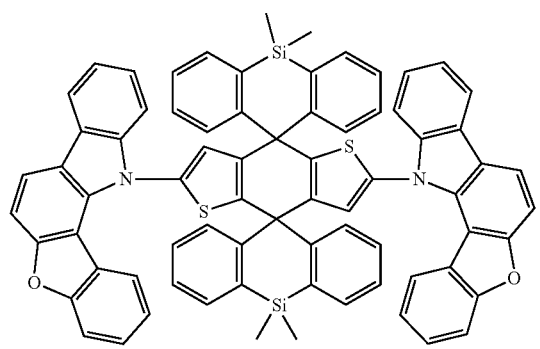

-continued
343
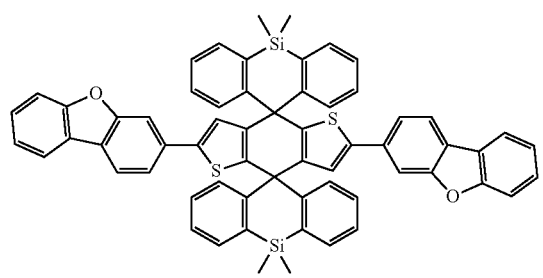
344
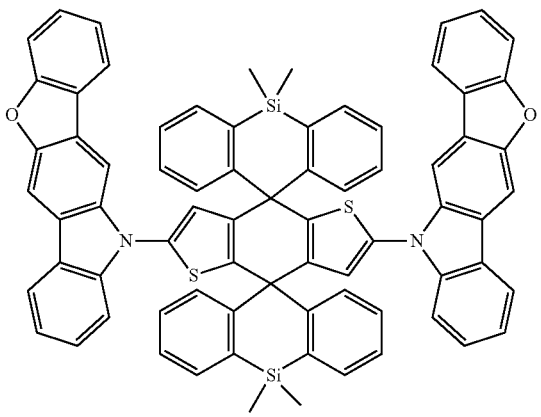
345
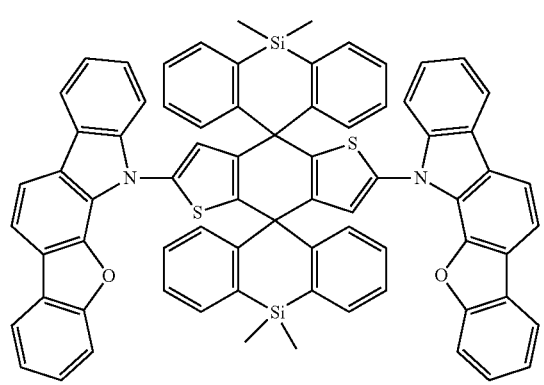
346
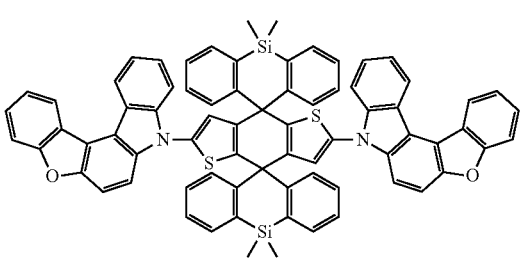
347
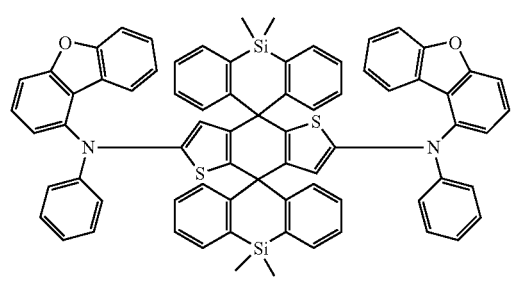
348
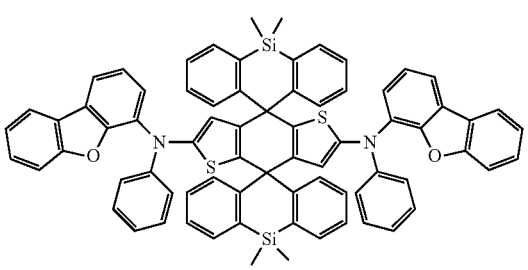
349
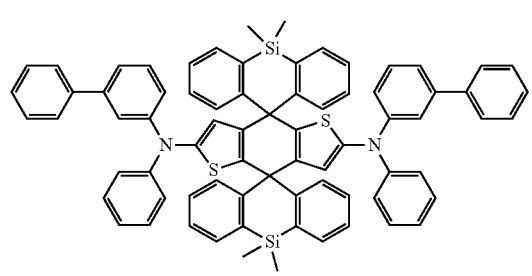
350
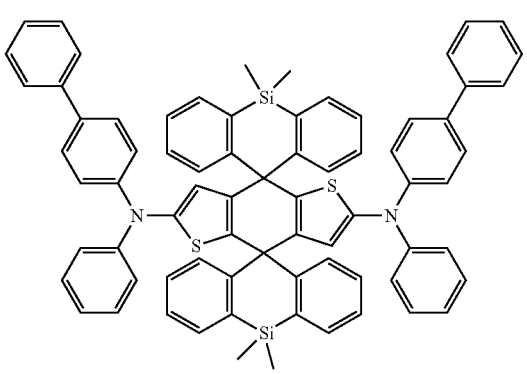

351
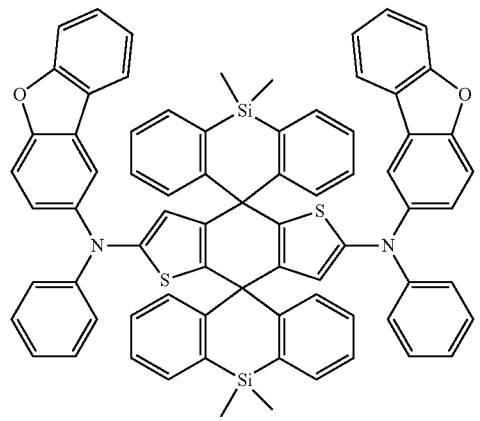
352
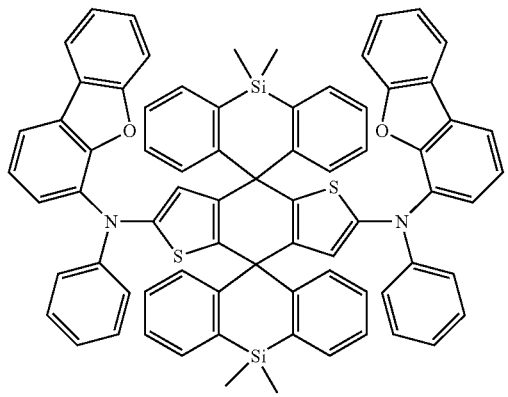
353
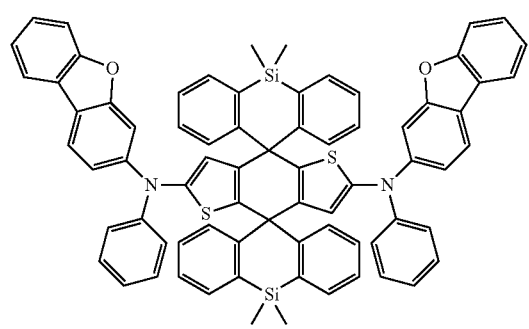
354
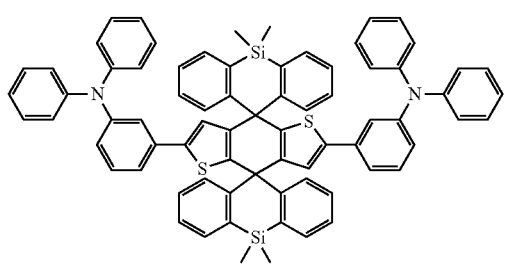
355
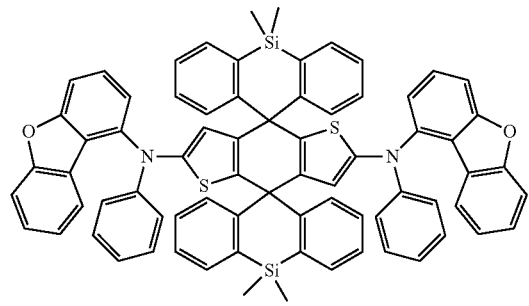
356
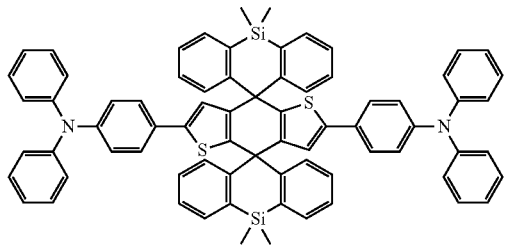
357
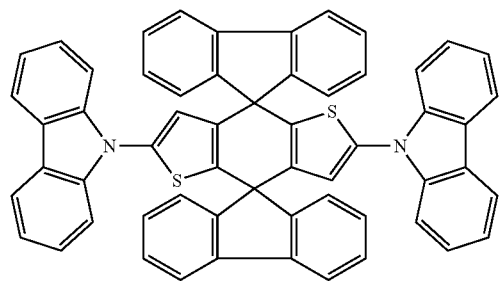
358
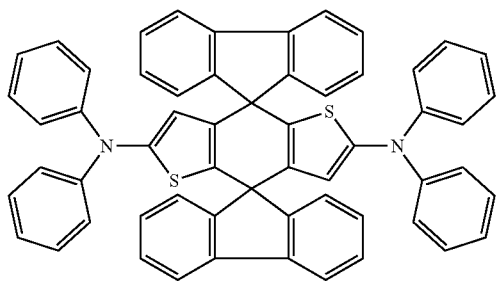
359
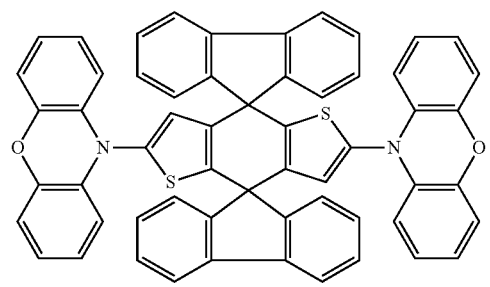
360
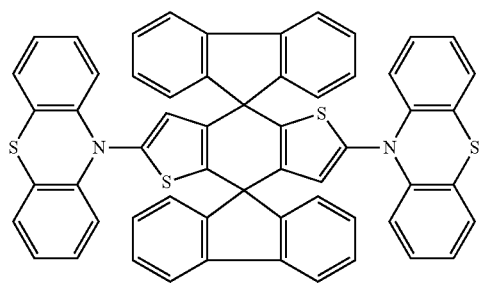

-continued
361 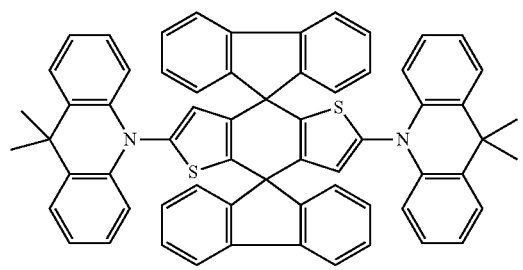
362 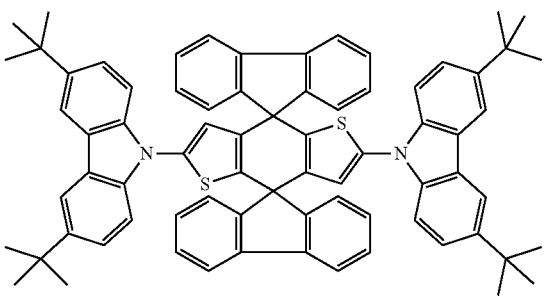
363 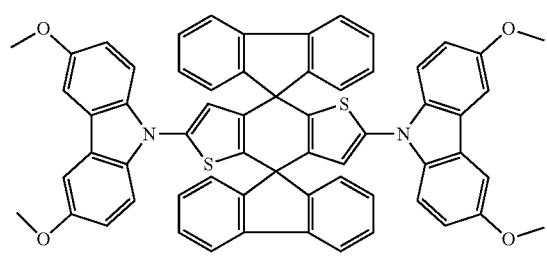
364 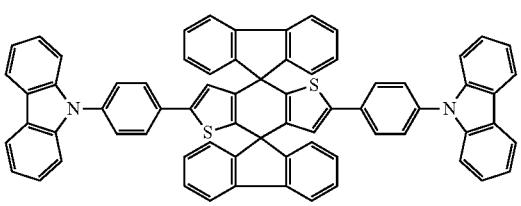
365 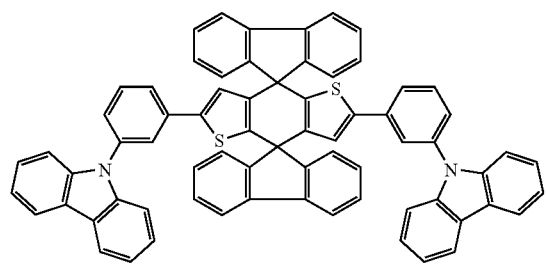
366 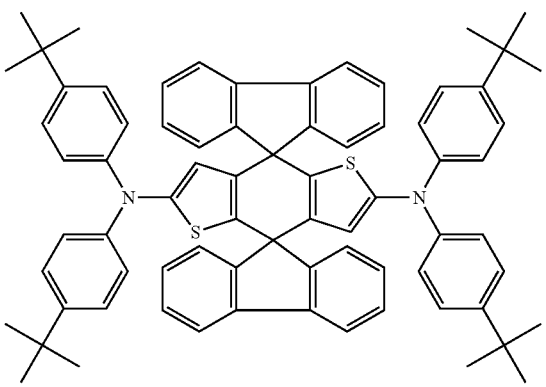
367 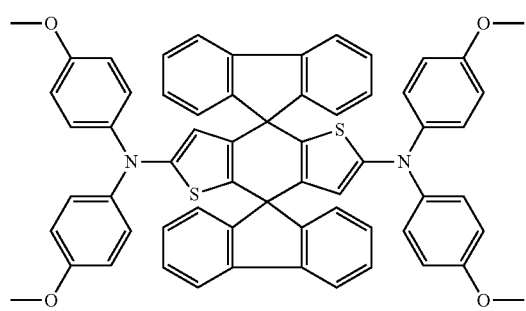
368 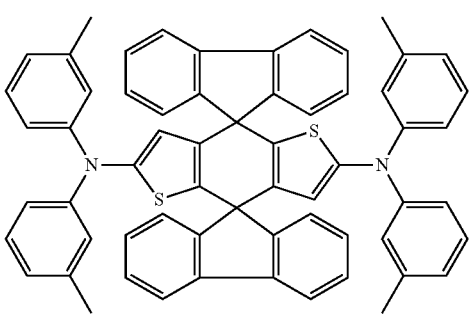
369 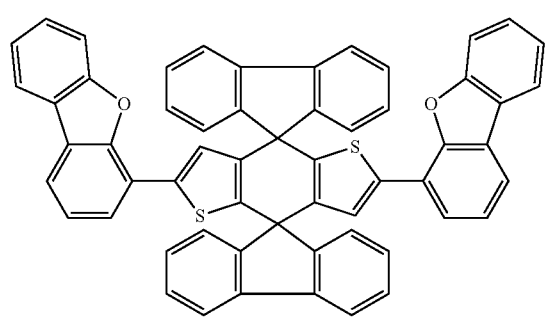
370 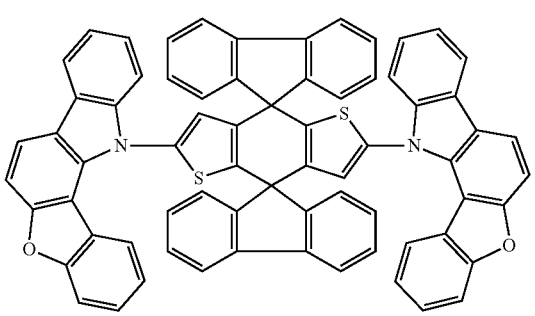

-continued
371
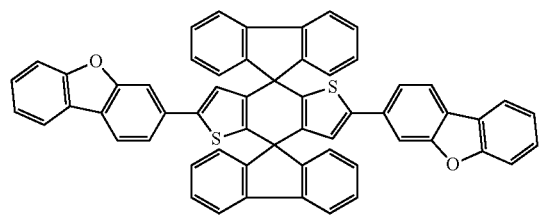
372
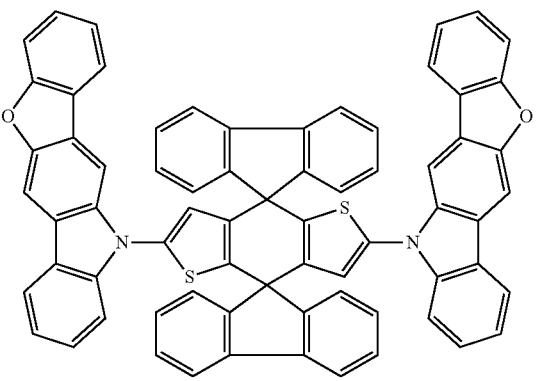
373
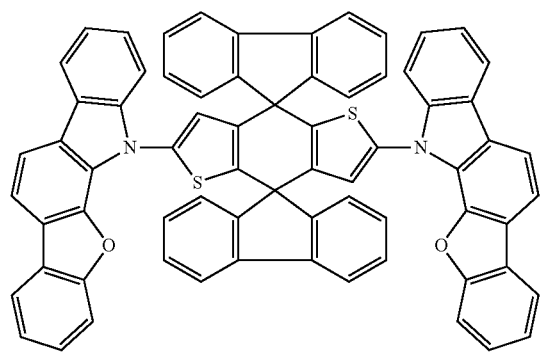
374
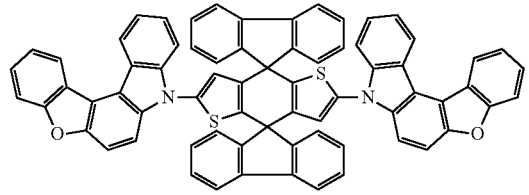
375
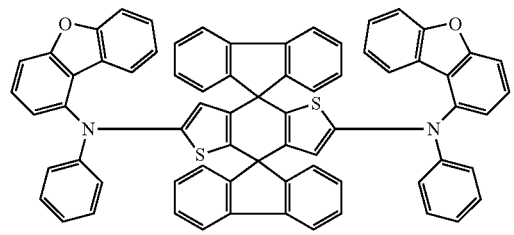
376
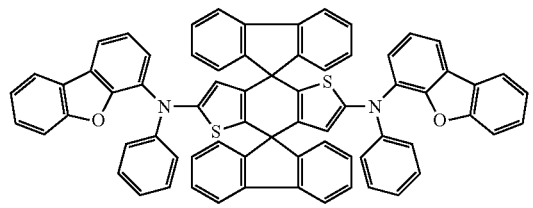
377
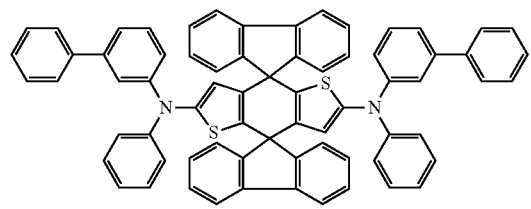
378
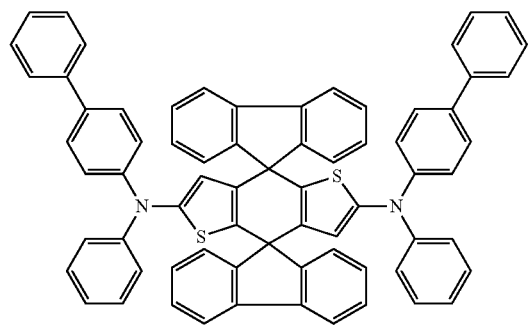

-continued
379
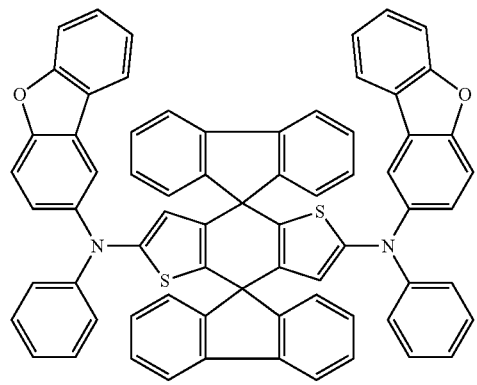
380
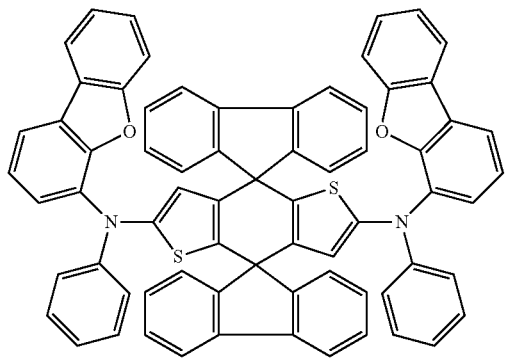
381
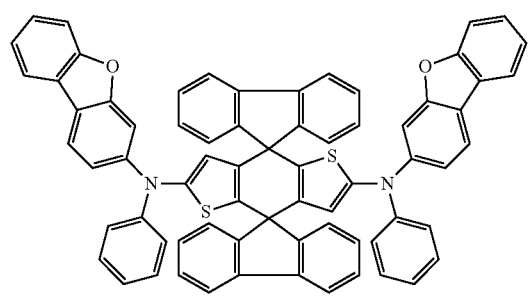
382
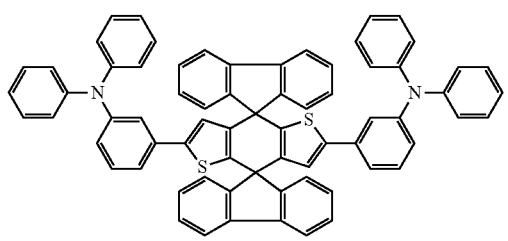
383
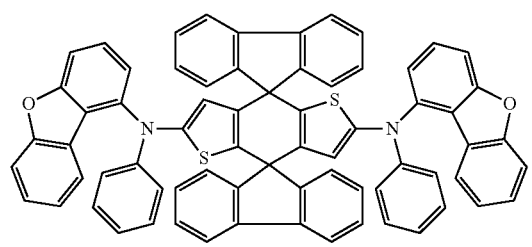
384
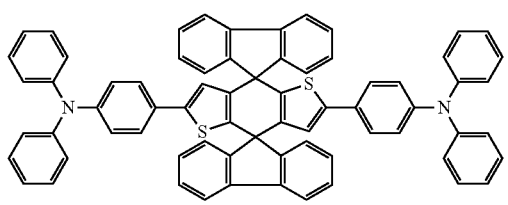
385
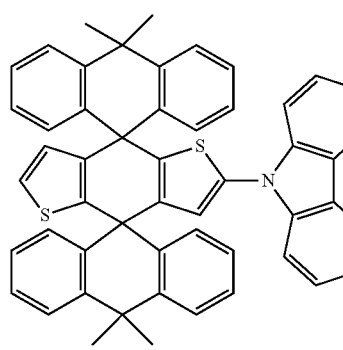
386
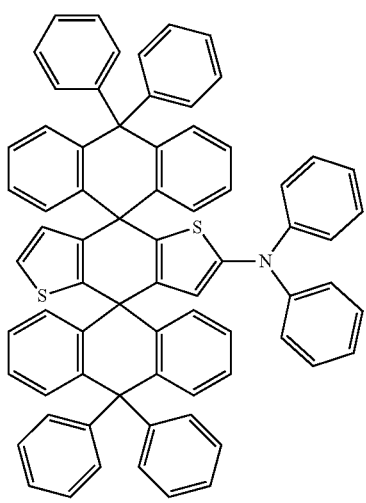

-continued
387
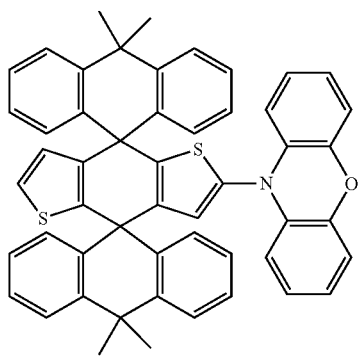
388
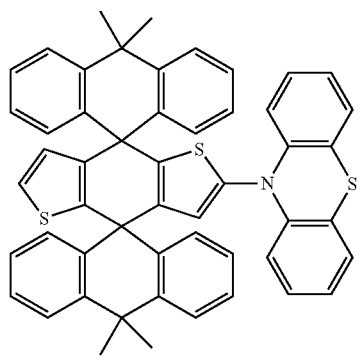
389
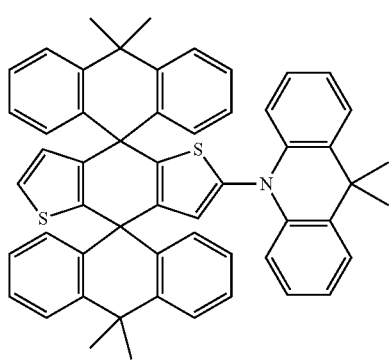
390
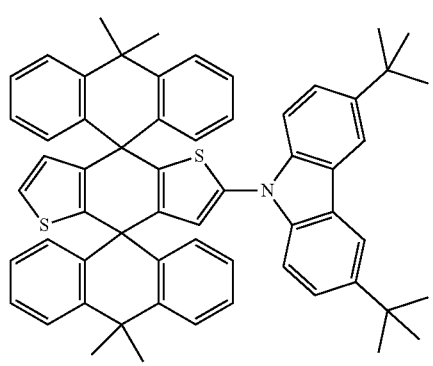
391
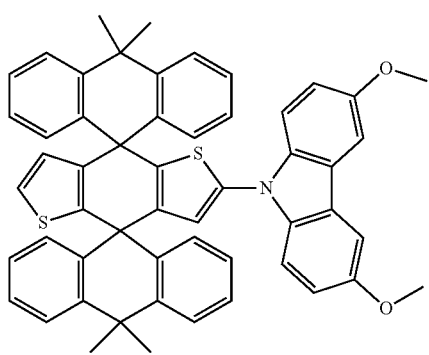
392
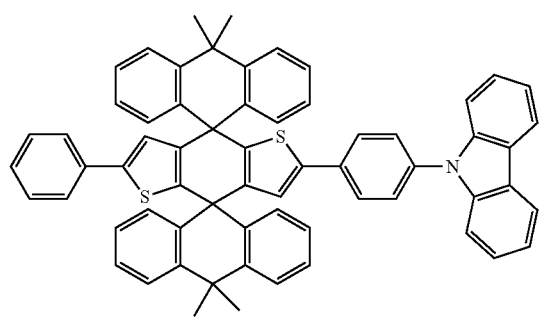
393
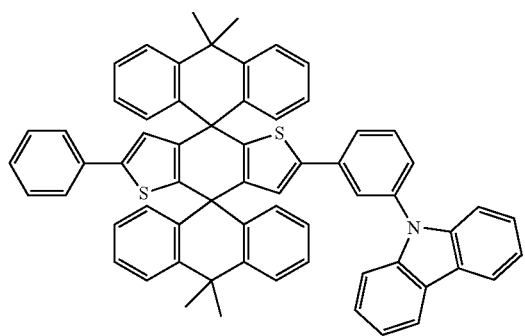
394
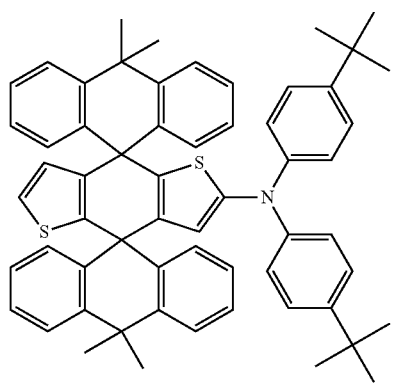

-continued
395
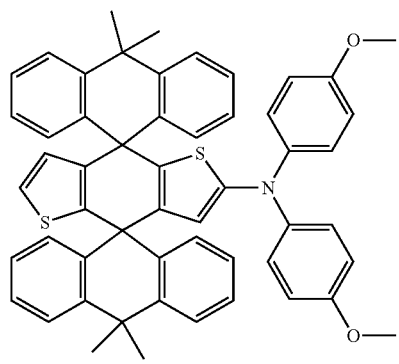
396
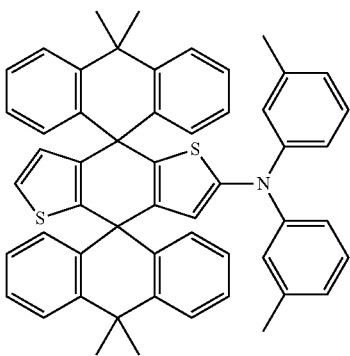
397
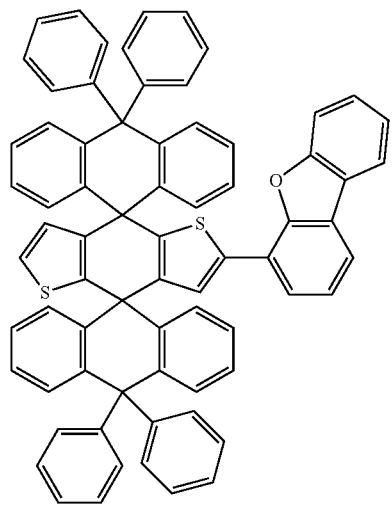
398
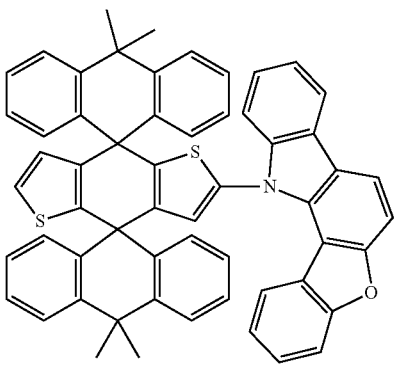
399
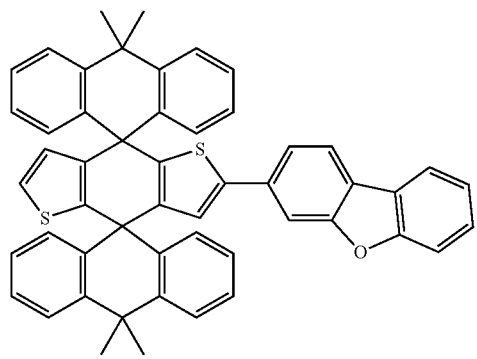
400
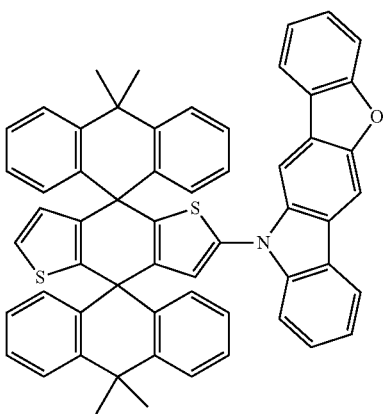
401
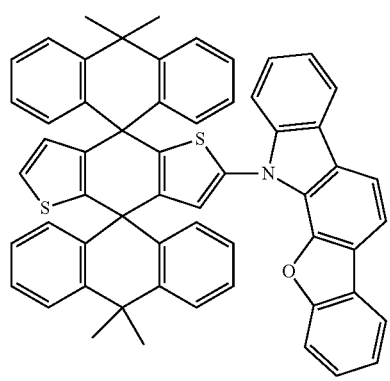
402
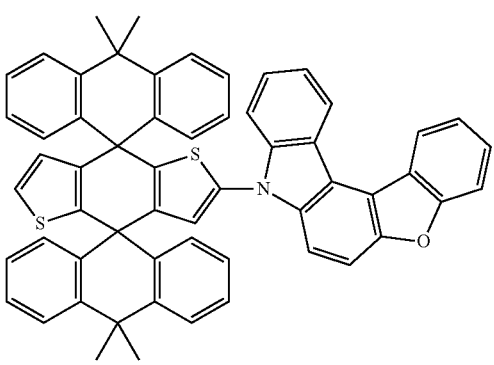

-continued
403
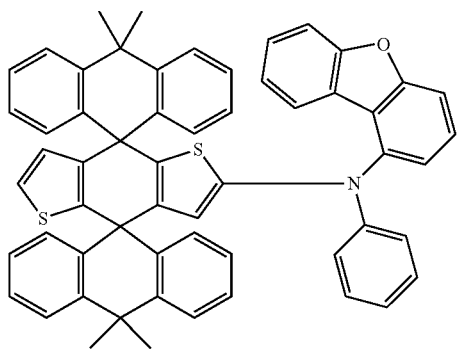
404
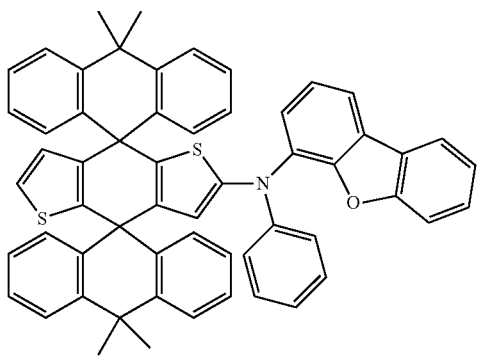
405
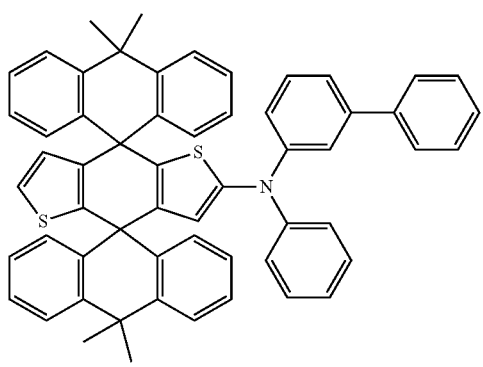
406
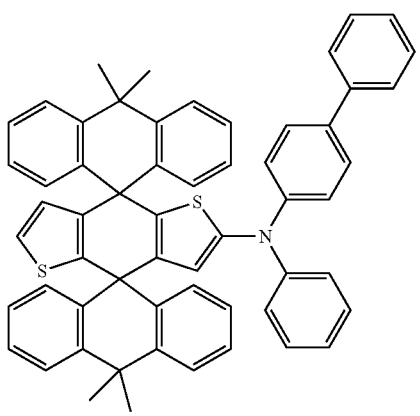
407
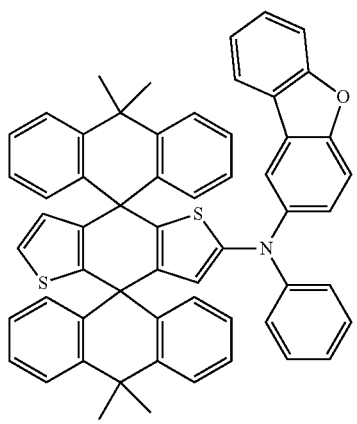
408
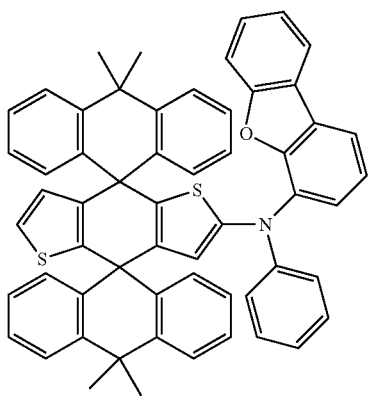
409
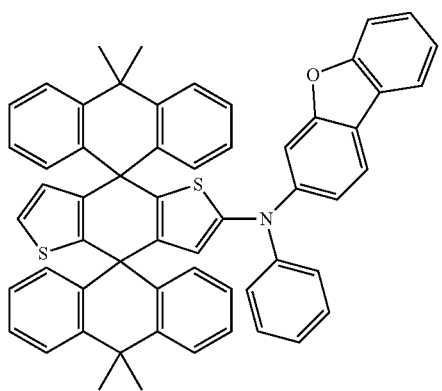
410
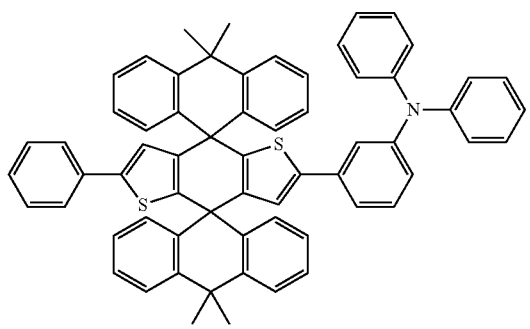

-continued
411 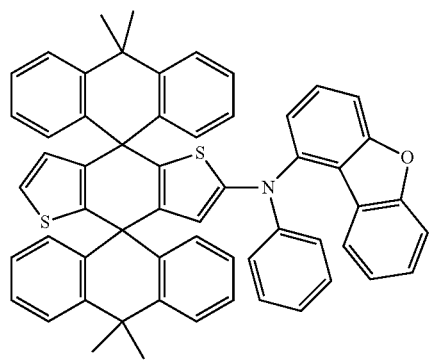
412 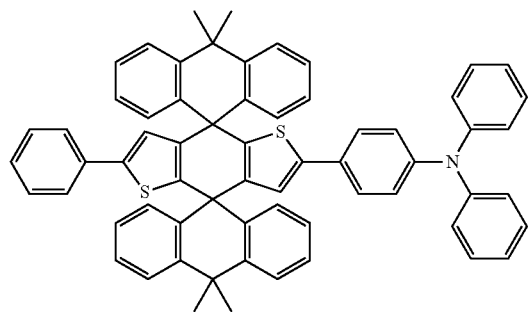
413 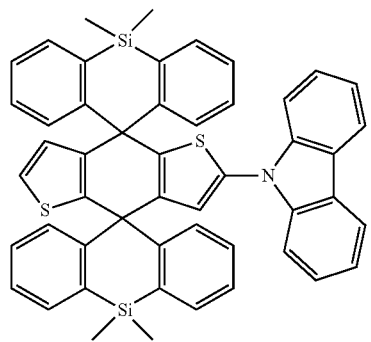
414 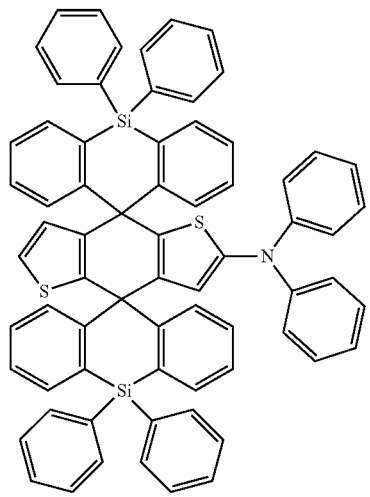
415 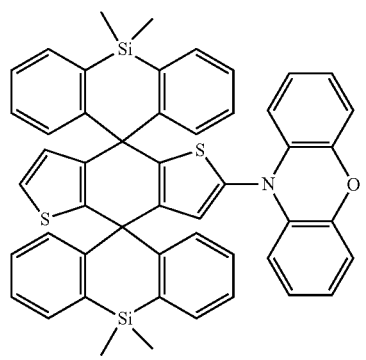
416 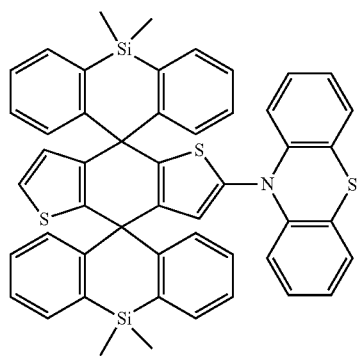
417 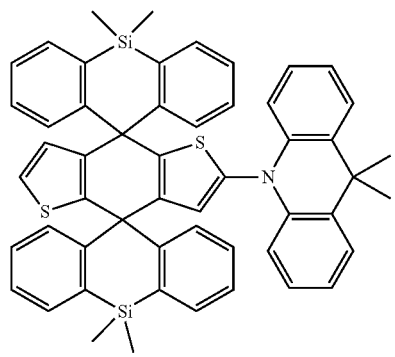
418 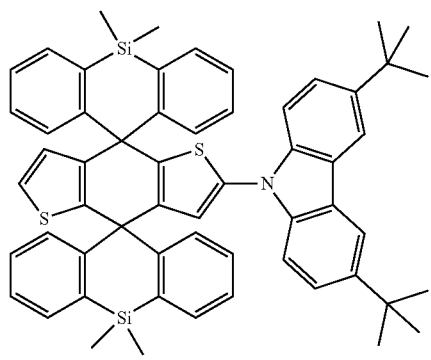

-continued
419
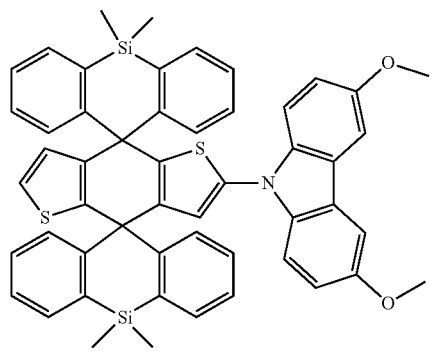
420
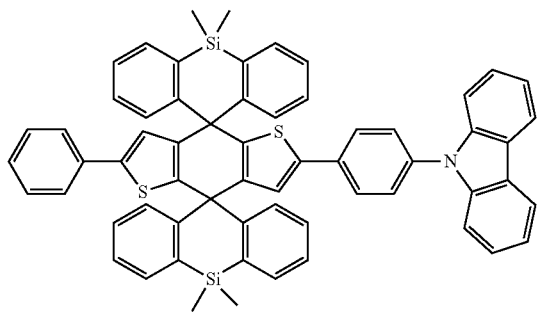
421
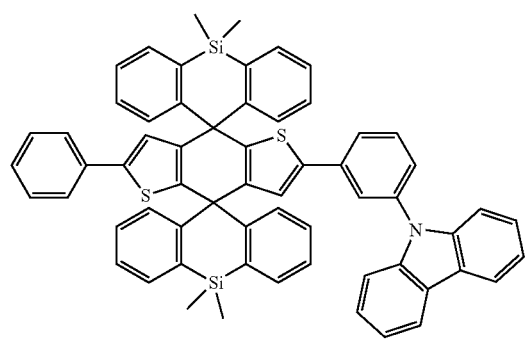
422
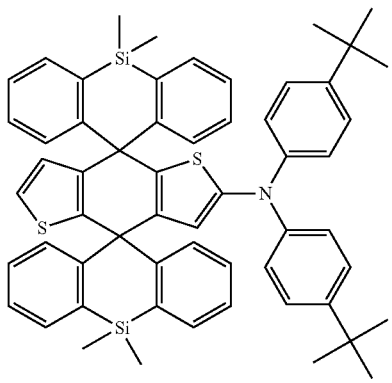
423
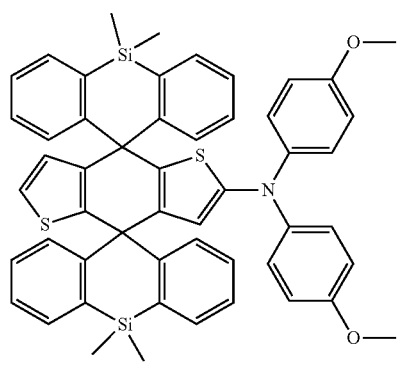
424
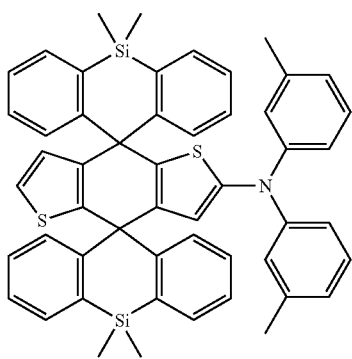
425
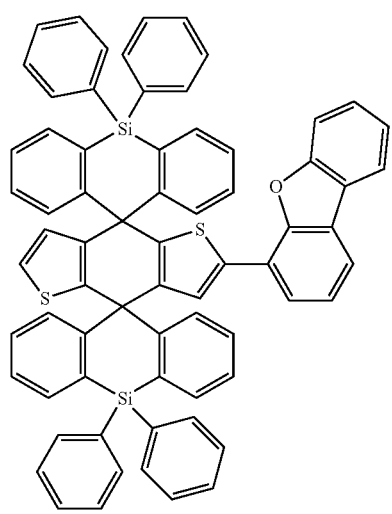
426
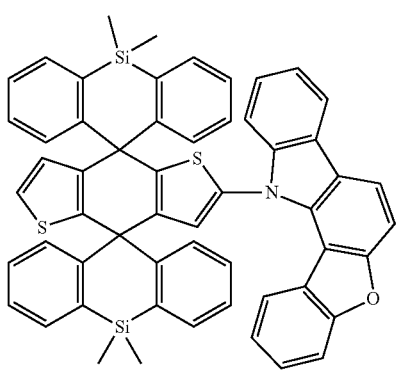

-continued
427
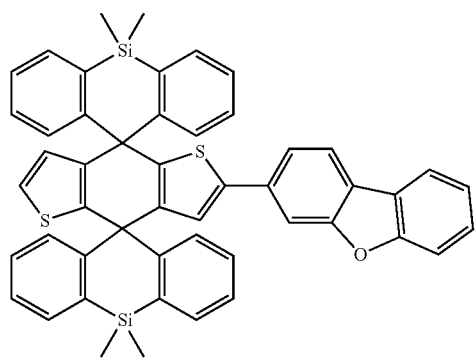
428
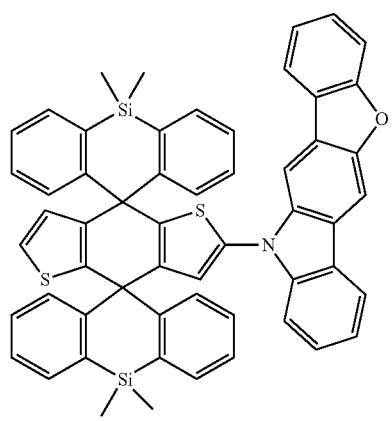
429
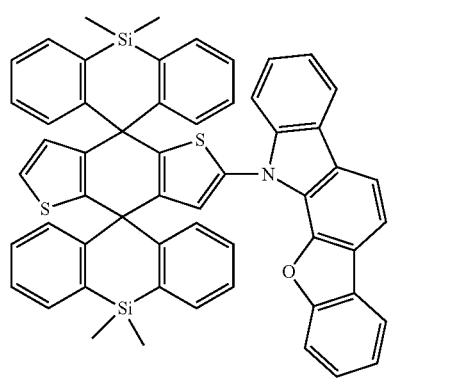
430
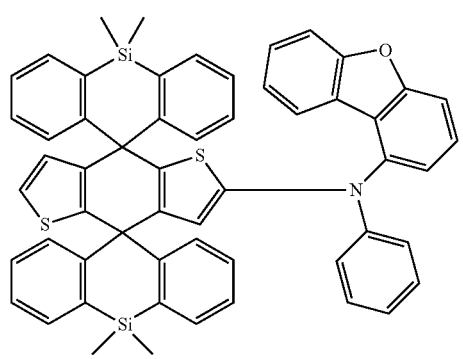
431
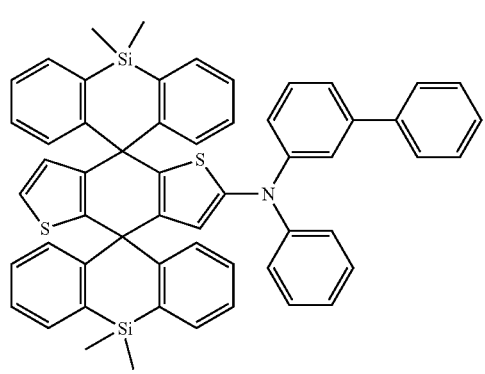
432
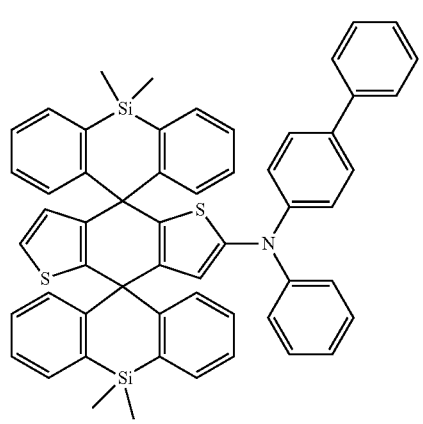
433
434

-continued
| 435 | 436 |
|---|---|
| 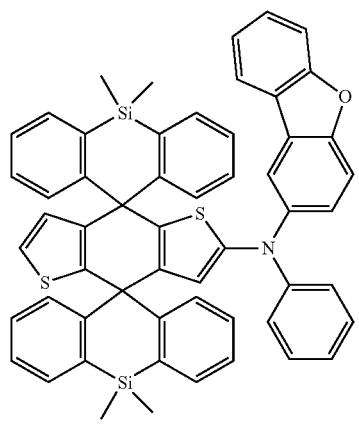 | 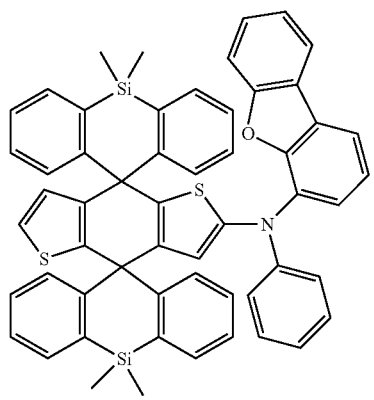 |
| 437 | 438 |
| 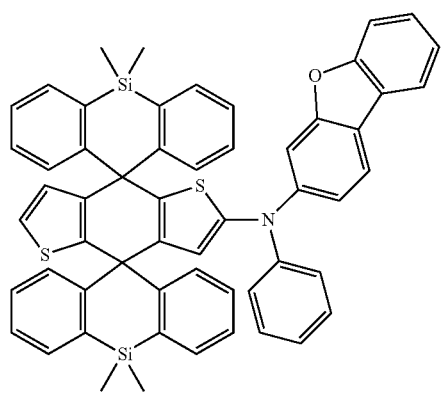 | 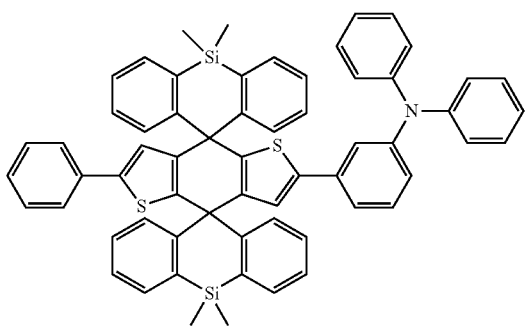 |
| 439 | 440 |
| 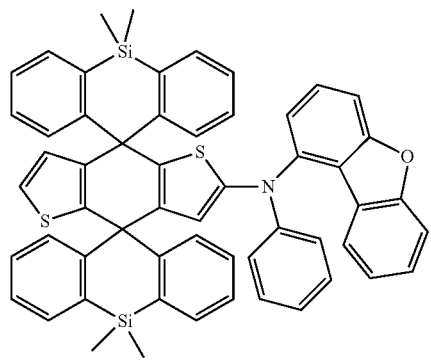 | 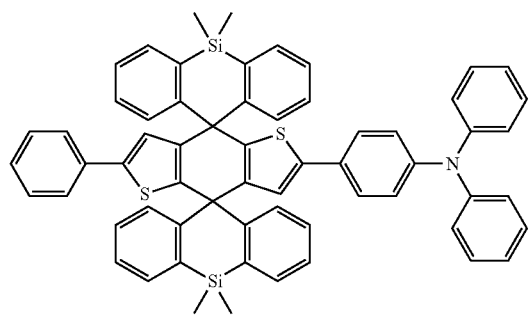 |
| 441 | 442 |
| 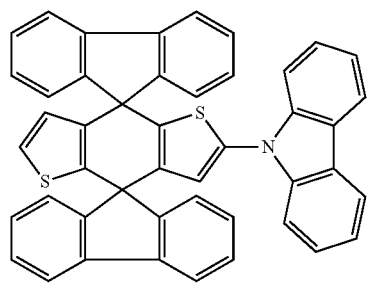 | 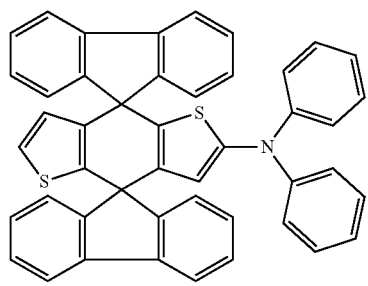 |

-continued
| 443 | 444 |
|---|---|
| 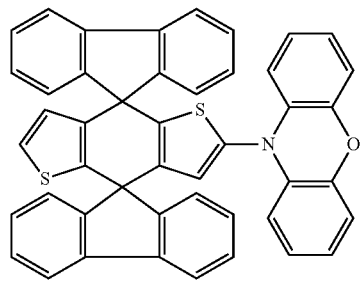 | 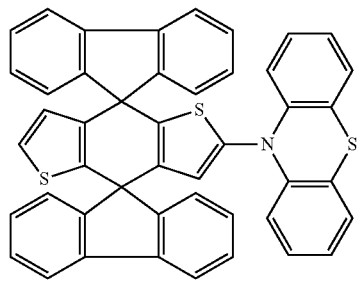 |
| 445 | 446 |
| 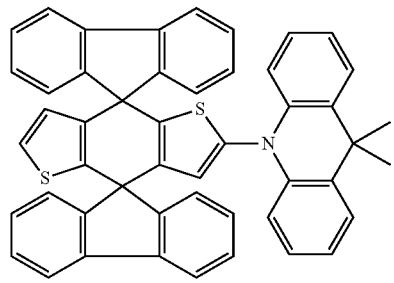 | 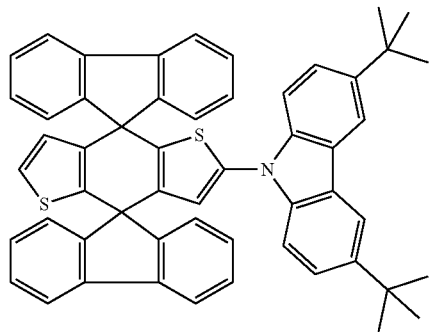 |
| 447 | 448 |
| 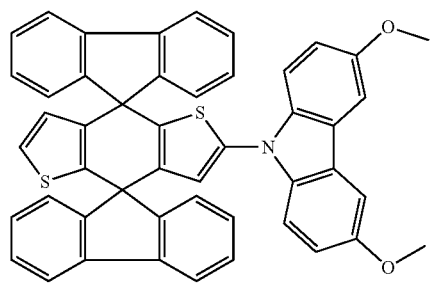 | 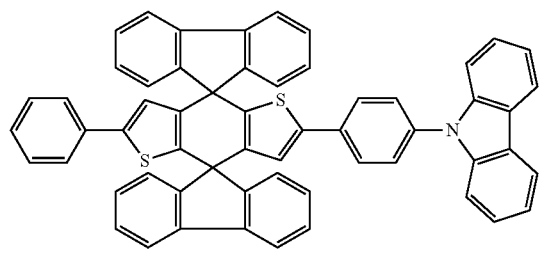 |
| 449 | 450 |
| 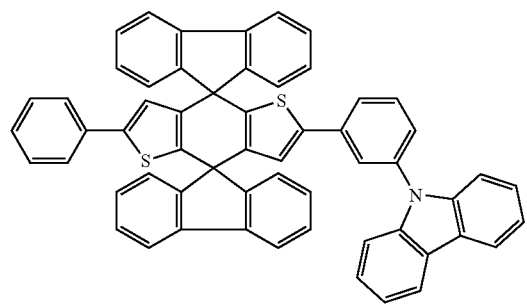 | 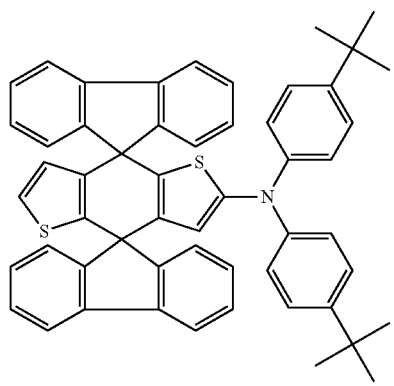 |
| 451 | 452 |
| 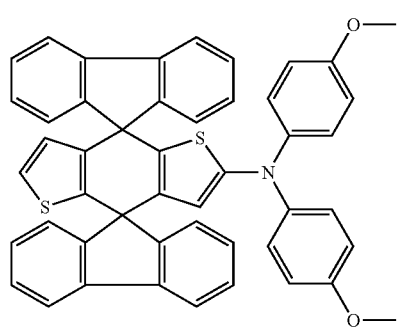 | 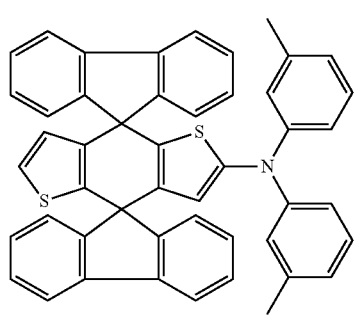 |

453
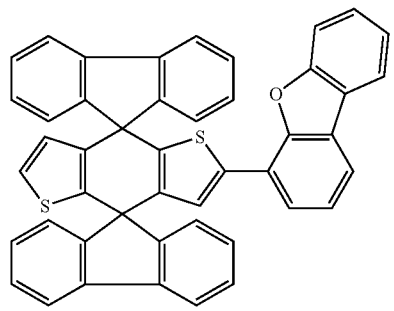
454
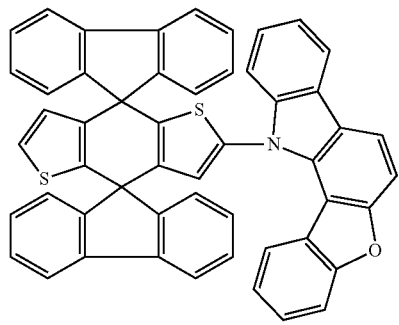
455
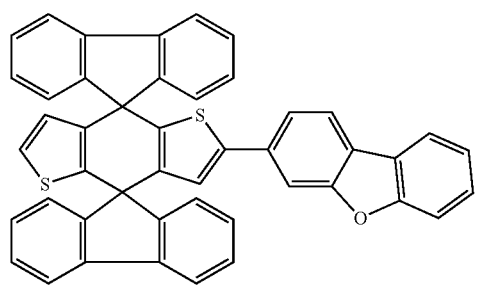
456
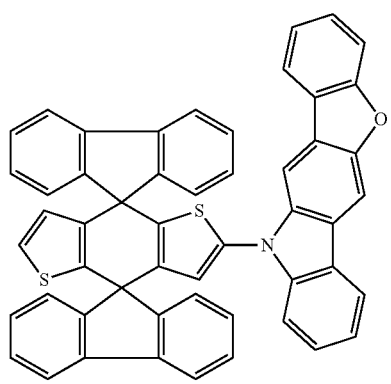
457
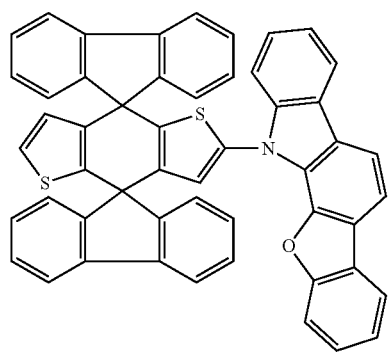
458
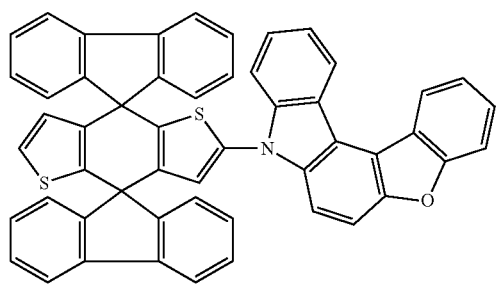
459
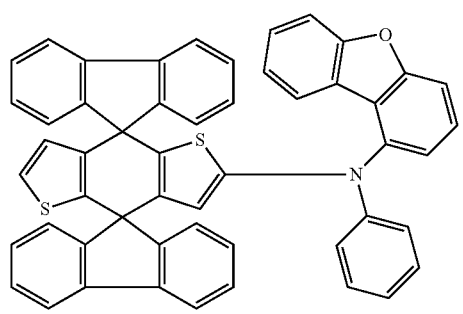
460
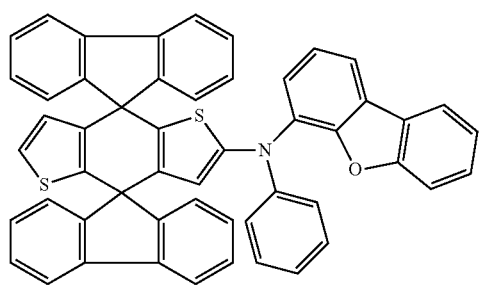

-continued
461
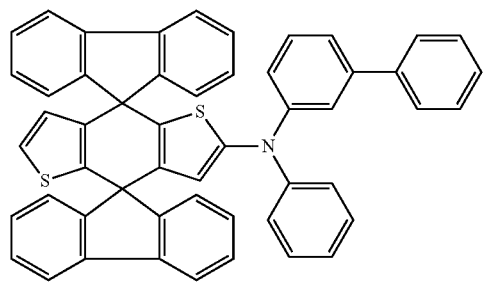
462
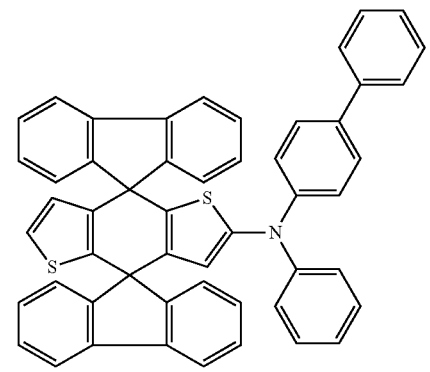
463
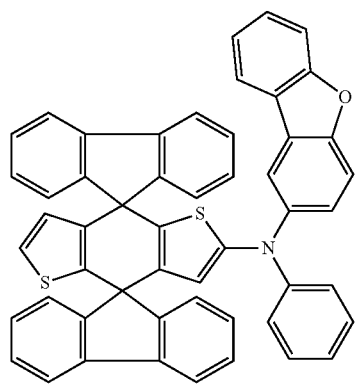
464
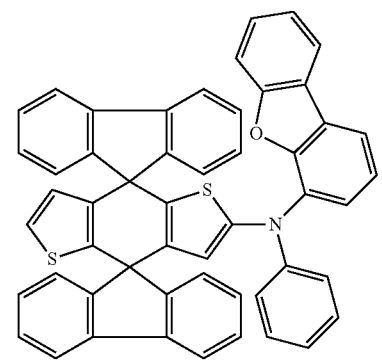
465
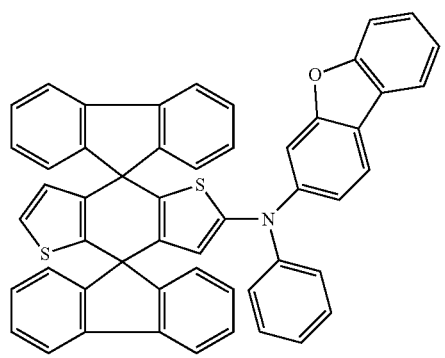
466
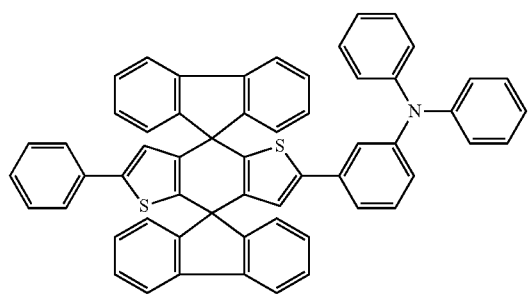
467
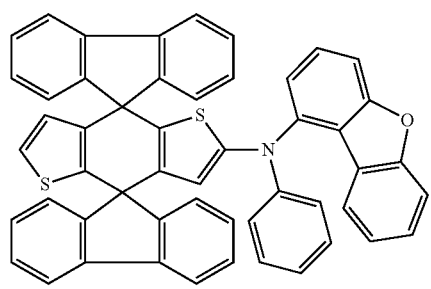
468
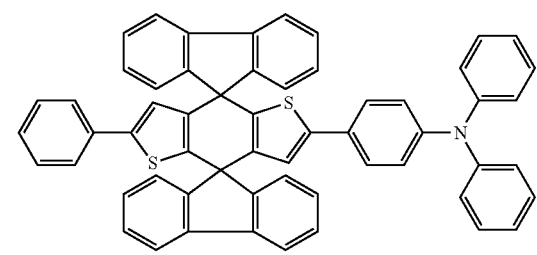

-continued
469
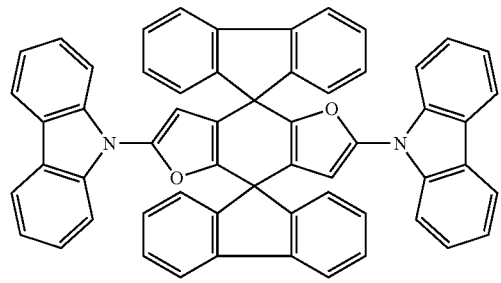
470
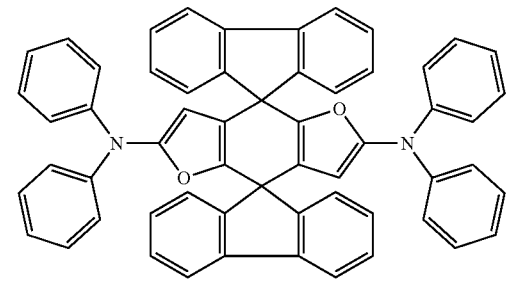
471
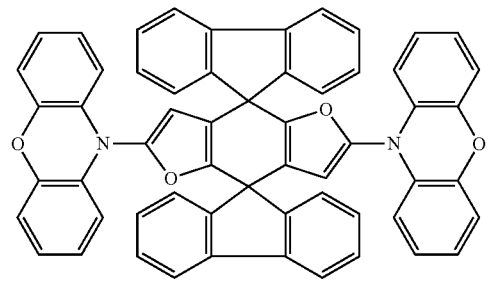
472
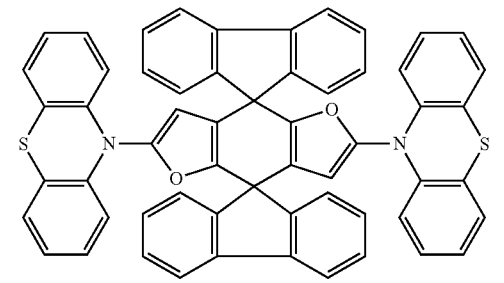
473
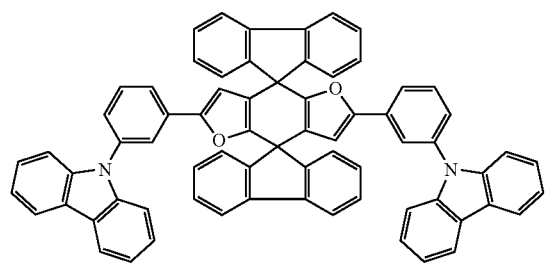
474
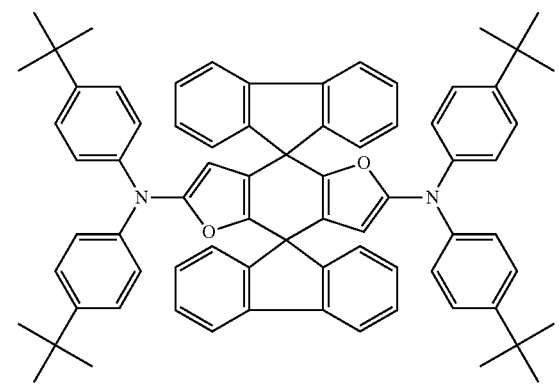
475
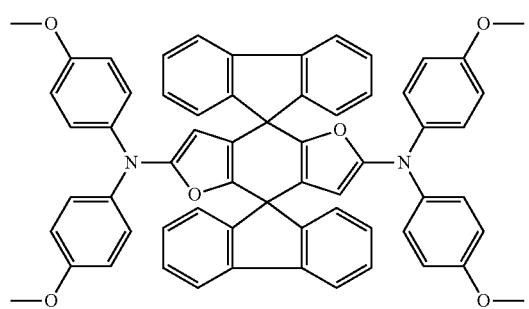
476
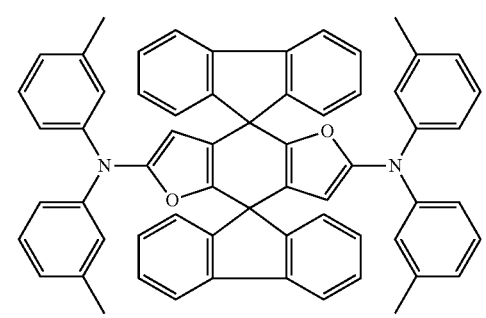
477
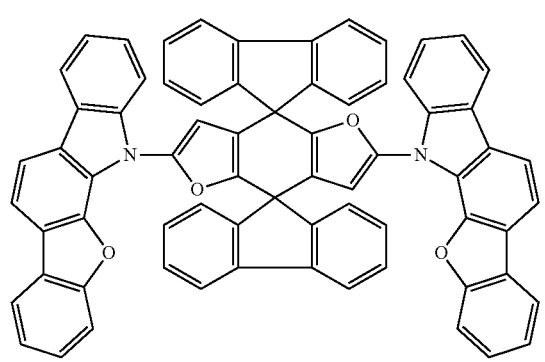
478
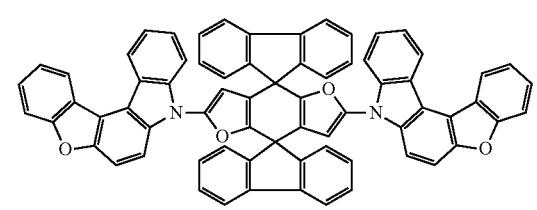

-continued

479 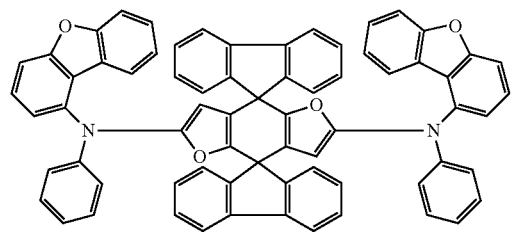

480 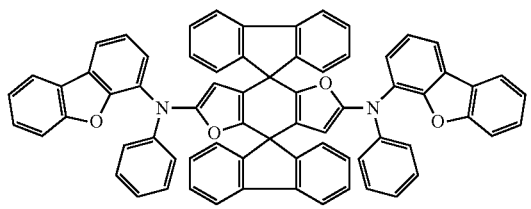

481 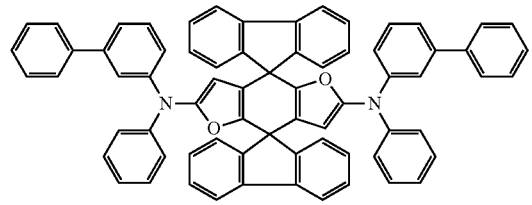

482 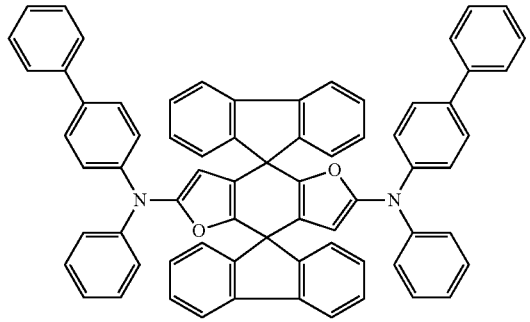

483 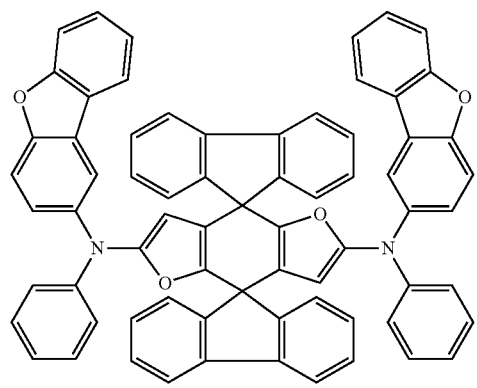

484 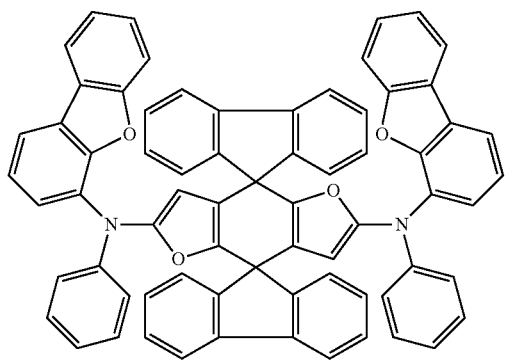

485 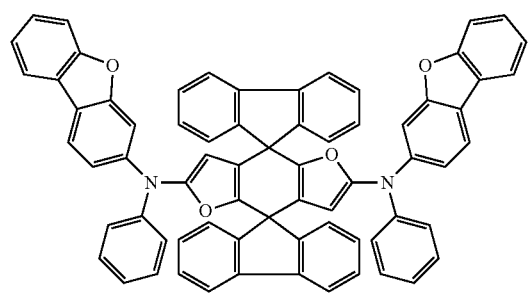

486 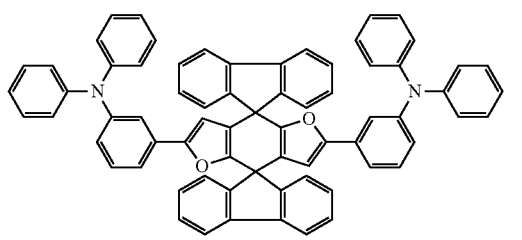

487 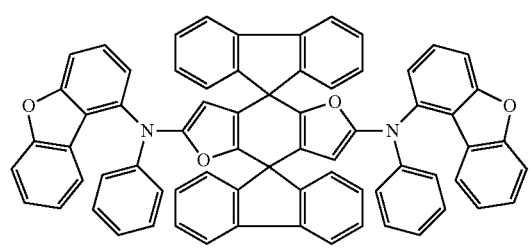

488 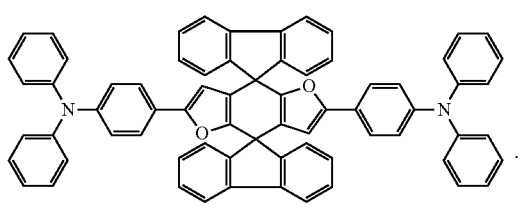

In a second aspect, the present disclosure provides an organic light-emitting element, including an anode, a cathode and an organic thin film layer disposed between the anode and the cathode; where the organic thin film layer includes a light-emitting layer, and further includes any one or a combination of at least two of a hole transport layer, an electron blocking layer and an auxiliary light-emitting layer.

At least one of the hole transport layer, the electron blocking layer and the auxiliary light-emitting layer contains at least one of the compounds described in the first aspect.

In an embodiment of the present disclosure, the organic thin film layer further includes any one or a combination of at least two of a hole injection layer, a hole blocking layer, an electron transport layer and an electron injection layer.

In a third aspect, the present disclosure provides a display panel including the organic light-emitting element described in the second aspect.

In a fourth aspect, the present disclosure provides a display device including the display panel described in the third aspect.

The examples of the present disclosure exemplarily provide the following compounds and preparation methods thereof, and adopt these compounds to exemplarily prepare organic light-emitting elements. The examples described herein are used for a better understanding of the present disclosure and should not be construed as specific limitations to the present disclosure.

Preparation Example 1

This preparation example provides a compound 134

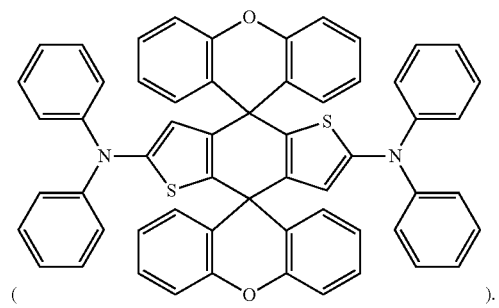 [SMILES: c1ccc(N(c2ccccc2)c2cc3c(s2)C2(c4ccccc4Oc4ccccc42)c2cc(N(c4ccccc4)c4ccccc4)sc2C32c3ccccc3Oc3ccccc32)cc1]

( ).

A specific preparation method is described below.

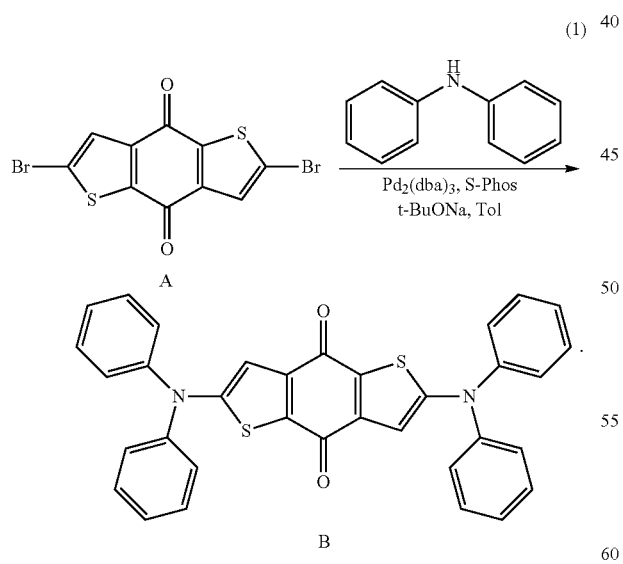

In a nitrogen atmosphere, raw materials: compound A (5 mmol), diphenylamine (11 mmol), t-BuONa (12.5 mmol), tris(dibenzalacetone)dipalladium (Pd$_2$(dba)$_3$) (0.25 mmol) and 2-dicyclohexylphosphine-2',6'-dimethoxybiphenyl (S-Phos) (0.75 mmol) were sequentially added to 200 mL of anhydrous toluene (Tol), deoxygenated for 10 min, raised to 110° C. and reacted for 24 h. After the reaction was finished, the reaction solution was cooled and suction filtered, the filtrate was collected, added with water and extracted with dichloromethane to separate liquid layers, and the organic phases were collected, dried with anhydrous sodium sulfate, and suction filtered. The filtrate was collected, the solvent was removed through rotary evaporation, and the reaction product was purified through column chromatography to obtain an intermediate B (with a yield of 78%).

LC-MS: m/z: calculated value: $C_{34}H_{22}N_2O_2S_2$: 554.68, a measured value: 554.31.

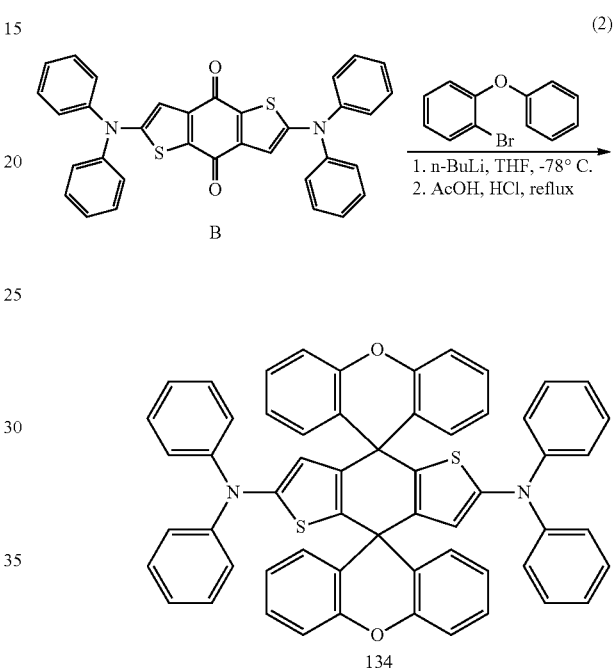

In a nitrogen atmosphere, a reactant 2-bromodiphenyl ether

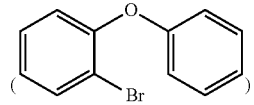 [SMILES: Brc1ccccc1Oc1ccccc1]

(2.2 mmol) was added to 100 mL of anhydrous THF and stirred at −78° C. for 10 min. After the reaction solution was cooled, 1.6M n-BuLi (2.5 mmol) was added dropwise. After the dropwise addition, the reaction was continued at −78° ° C. for 2 h. The intermediate B (1 mmol) was dissolved in a solution of anhydrous THF (50 mL), and then added dropwise to a low-temperature reaction solution with an injector. After the dropwise addition, the reaction was continued at a low temperature for 1 h and then raised to room temperature for a reaction of 5 h. After the reaction was finished, a small amount of water was added to quench the reaction, water and dichloromethane were added for extraction, and the organic phases were collected, dried with anhydrous sodium sulfate and suction filtered. The filtrate was collected, and the solvent was removed through rotary evaporation to obtain the crude product.

(3) Under a nitrogen condition, the above crude product was added to 80 mL of acetic acid, stirred and heated, reacted at 120° ° C. for 2 h, added with 5 mL of hydrochloric acid, and heated at this temperature for 12 h. After the reaction was finished, the reaction solution was cooled and extracted, the organic phases were collected, and the solvent was removed through rotary evaporation. The reaction product was purified through column chromatography to obtain the compound 134 (with a yield of 65%).

LC-MS: m/z: a calculated value: $C_{58}H_{38}N_2O_2S_2$: 859.06, a measure value: 858.79.

Elemental analysis result of the compound: a calculated value: $C_{58}H_{38}N_2O_2S_2$ (%): C 81.09, H 4.46, N 3.26; a test value: C 81.08, H 4.47, N 3.28.

Preparation Example 2

This preparation example provides a compound 14

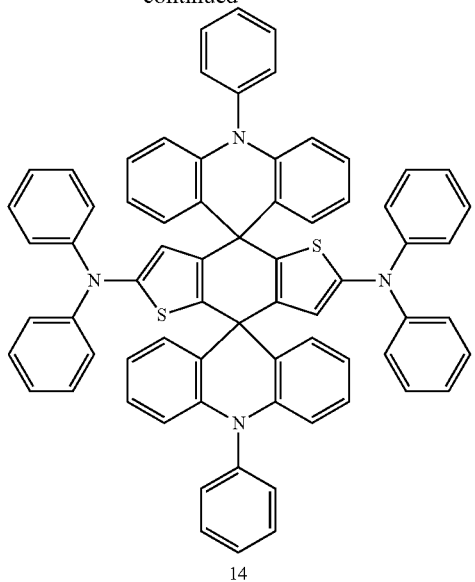

14

The preparation method of the organic compound 14 only differed from that of Example 1 in that 2-bromodiphenyl ether

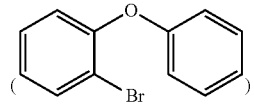 [SMILES: Brc1ccccc1Oc1ccccc1]

in step (2) in Example 1 was replaced with an equal molar amount of 2-bromotriphenylamine

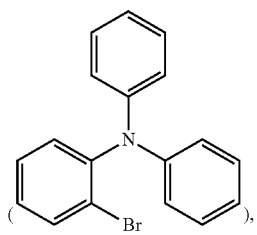 [SMILES: Brc1ccccc1N(c1ccccc1)c1ccccc1]

and other raw materials, reaction steps and reaction conditions were the same as those in Example 1, and the target product 2 was finally obtained (with a yield of 62%).

LC-MS: m/z: a calculated value: $C_{70}H_{48}N_4S_2$: 1009.29, a measure value: 1008.81.

Elemental analysis result of the compound: a calculated value: $C_{70}H_{48}N_4S_2$ (%): C 83.30, H 4.79, N 5.55; a test value: C 83.29, H 4.78, N 5.57.

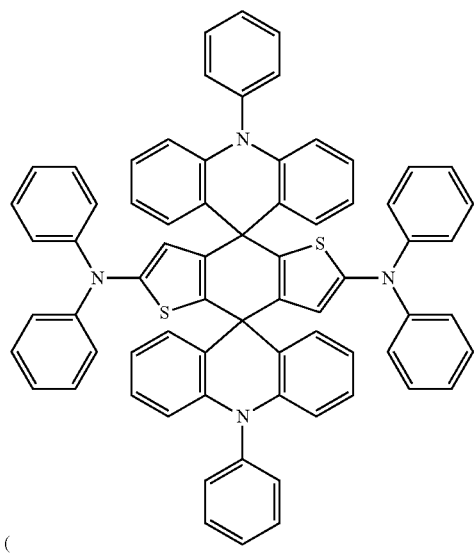

A specific preparation method is described below.

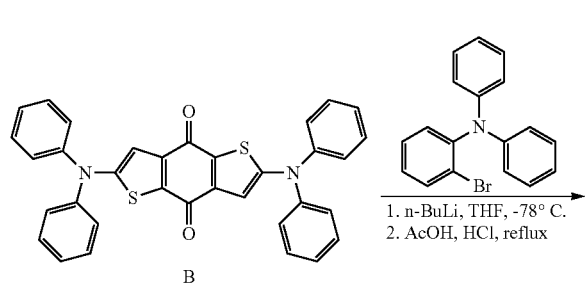

Preparation Example 3

This preparation example provides a compound 302

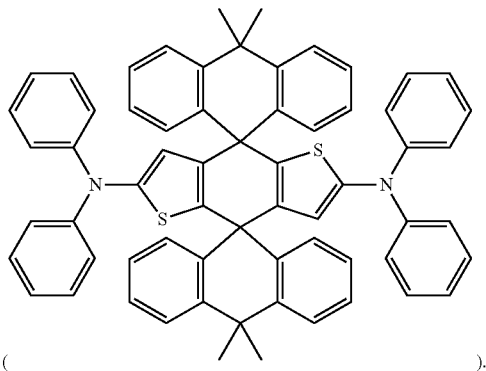 [SMILES: CC1(C)c2ccccc2C2(c3ccccc31)c1cc(N(c3ccccc3)c3ccccc3)sc1C1(c3ccccc3C(C)(C)c3ccccc31)c1cc(N(c3ccccc3)c3ccccc3)sc12]

( ).

A specific preparation method is described below.

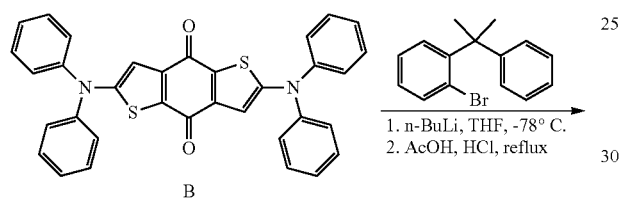

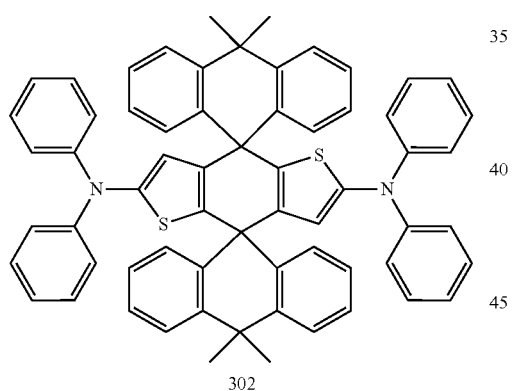

302

The preparation method of the organic compound 302 only differed from that of Preparation Example 1 in that 2-bromodiphenyl ether

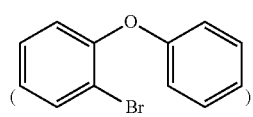 [SMILES: Brc1ccccc1Oc1ccccc1]

in step (2) in Preparation Example 1 was replaced with an equal molar amount of 1-bromo-2-(1-methyl-1-phenyl-ethyl)-benzene

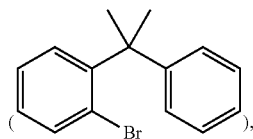

and other raw materials, reaction steps and reaction conditions were the same as those in Preparation Example 1, and the target product 3 was finally obtained (with a yield of 60%).

LC-MS: m/z: a calculated value: $C_{64}H_{50}N_2S_2$: 911.23, a measured value: 910.89.

Elemental analysis result of the compound: a calculated value: $C_{64}H_{50}N_2S_2$ (%): C 84.36, H 5.53, N 3.07; a test value: C 84.37, H 5.55, N 3.06.

Preparation Example 4

This preparation example provides a compound 167

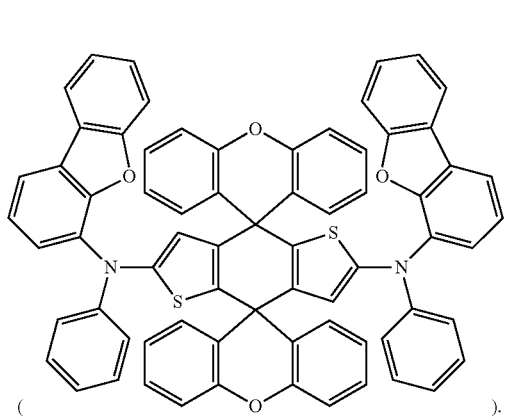 [SMILES: c1ccc(N(c2cc3c(s2)C2(c4ccccc4Oc4ccccc42)c2cc(N(c4ccccc4)c4cccc5c4oc4ccccc45)sc2C32c3ccccc3Oc3ccccc32)c2cccc3c2oc2ccccc23)cc1]

( ).

A specific preparation method is described below.

(1)

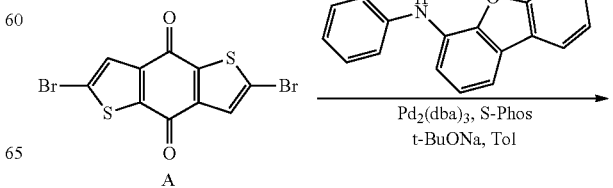

-continued

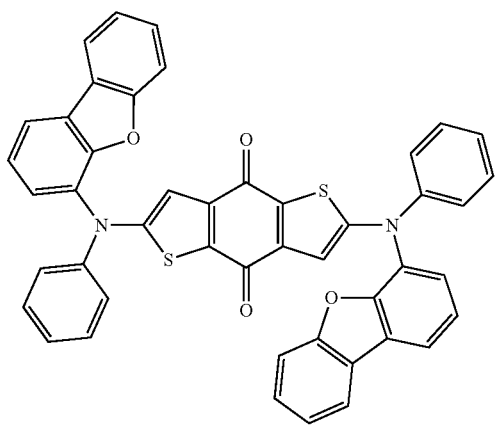

C

An intermediate C was synthesized: a preparation method of the intermediate C only differed from that of the intermediate B in that diphenylamine

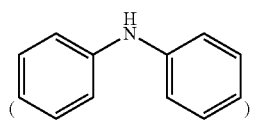 [SMILES: c1ccc(Nc2ccccc2)cc1]

in step (1) in Preparation Example 1 was replaced with an equal molar amount of dibenzofuran-4-yl-aniline

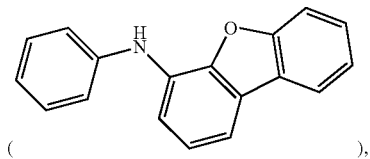 [SMILES: c1ccc(Nc2cccc3c2oc2ccccc23)cc1]

and other raw materials, reaction steps and reaction conditions were the same as those in step (1) of Preparation Example 1, and the compound C was finally obtained (with a yield of 75%).

LC-MS: m/z: a calculated value: $C_{46}H_{26}N_2O_4S_2$: 734.84, a measured value: 734.39.

(2)

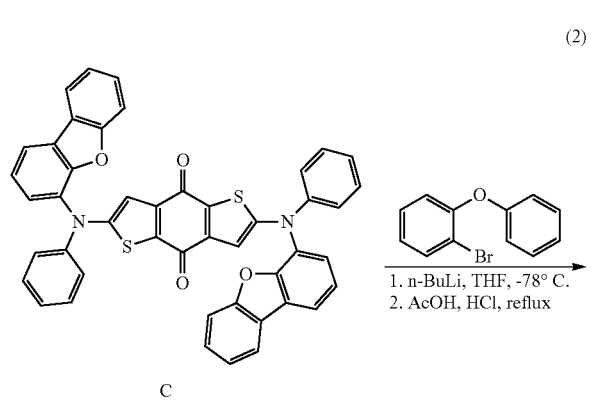

-continued

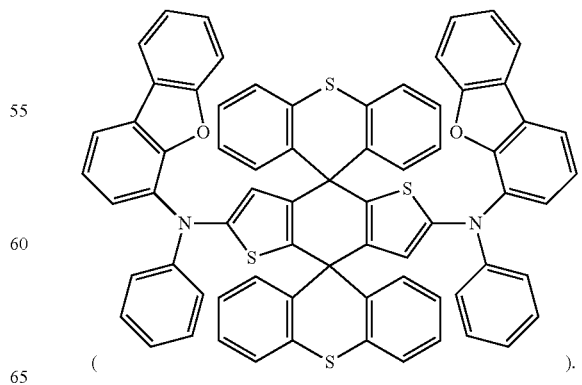

167

In a nitrogen atmosphere, a reactant 2-bromodiphenyl ether (2.2 mmol) was added to 100 mL of anhydrous THF and stirred at −78° C. for 10 min. After the reaction solution was cooled, 1.6M n-BuLi (2.5 mmol) was added dropwise. After the dropwise addition, the reaction was continued at −78° C. for 2 h. The intermediate C (1 mmol) was dissolved in a solution of anhydrous THF (50 mL), and then added dropwise to a low-temperature reaction solution with an injector. After the dropwise addition, the reaction was continued at a low temperature for 1 h and then raised to room temperature for a reaction of 5 h. After the reaction was finished, a small amount of water was added to quench the reaction, water and dichloromethane were added for extraction, and the organic phases were collected, dried with anhydrous sodium sulfate and suction filtered. The filtrate was collected, and the solvent was removed through rotary evaporation to obtain the crude product.

(3) Under a nitrogen condition, the above crude product was added to 80 mL of acetic acid, stirred and heated, reacted at 120° C. for 2 h, added with 5 mL of hydrochloric acid, and heated at this temperature for 12 h. After the reaction was finished, the reaction solution was cooled and extracted, the organic phases were collected, and the solvent was removed through rotary evaporation. The reaction product was purified through column chromatography to obtain the compound 167 (with a yield of 65%).

LC-MS: m/z: a calculated value: $C_{70}H_{42}N_2O_4S_2$: 1039.22, a measured value: 1038.87.

Elemental analysis result of the compound: a calculated value: $C_{70}H_{42}N_2O_4S_2$ (%): C 80.90, H 4.07, N 2.70; a test value: C 80.89, H 4.06, N 2.71.

Preparation Example 5

This preparation example provides a compound 287

A specific preparation method is described below.

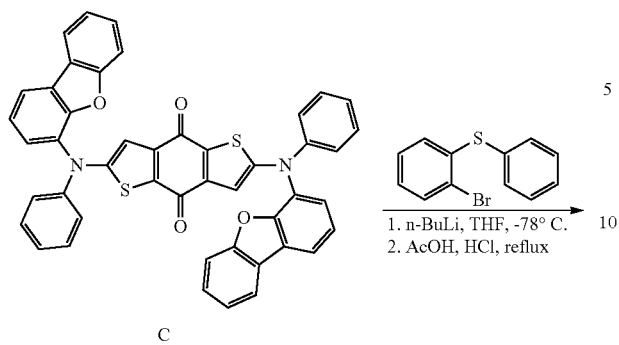

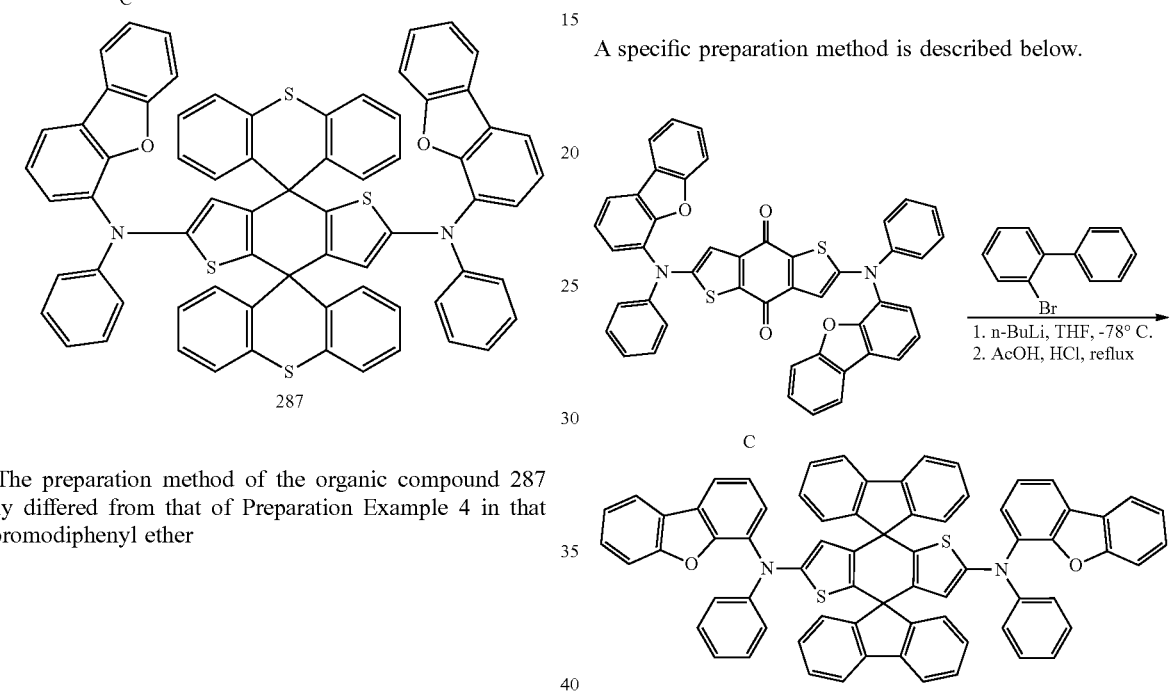

287

The preparation method of the organic compound 287 only differed from that of Preparation Example 4 in that 2-bromodiphenyl ether

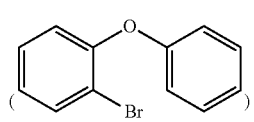 [SMILES: Brc1ccccc1Oc1ccccc1]

in step (2) in Preparation Example 4 was replaced with an equal molar amount of 1-bromo-2-phenylsulfanylbenzene

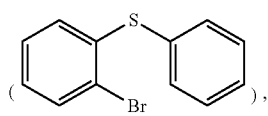 [SMILES: Brc1ccccc1Sc1ccccc1]

and other raw materials, reaction steps and reaction conditions were the same as those in Preparation Example 4, and the target product 5 was finally obtained (with a yield of 63%).

LC-MS: m/z: a calculated value: $C_{70}H_{42}N_2O_2S_4$: 1071.35, a measured value: 1070.93.

Elemental analysis result of the compound: a calculated value: $C_{70}H_{42}N_2O_2S_4$ (%): C 78.48, H 3.95, N 2.61; a test value: C 78.47, H 3.94, N 2.62.

Preparation Example 6

This preparation example provides a compound 380

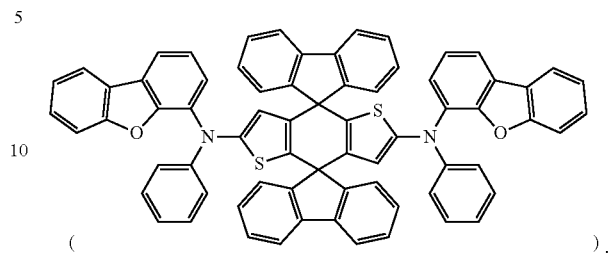

A specific preparation method is described below.

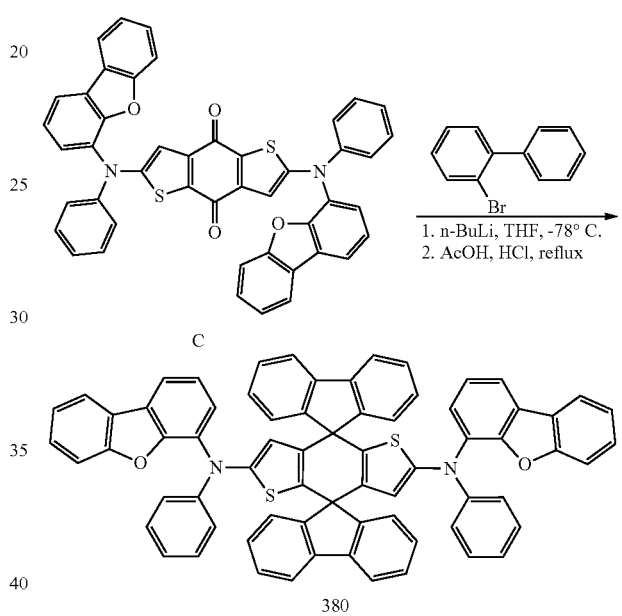

380

The preparation method of the organic compound 380 only differed from that of Preparation Example 4 in that 2-bromodiphenyl ether

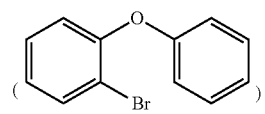 [SMILES: Brc1ccccc1Oc1ccccc1]

in step (2) in Preparation Example 4 was replaced with an equal molar amount of 2-bromodiphenyl

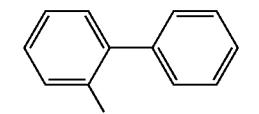

and other raw materials, reaction steps and reaction conditions were the same as those in Preparation Example 4, and the target product 6 was finally obtained (with a yield of 68%).

LC-MS: m/z: a calculated value: $C_{70}H_{42}N_2O_2S_2$: 1007.22, a measured value: 1006.90.

Elemental analysis result of the compound: a calculated value: $C_{70}H_{42}N_2O_2S_2$ (%): C 83.47, H 4.20, N 2.78; a test value: C 83.49, H 4.21, N 2.77.

Preparation Example 7

This preparation example provides a compound 194

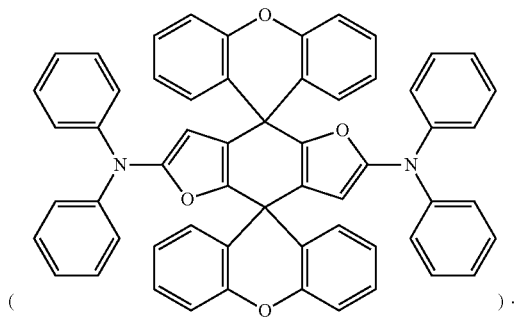 [SMILES: c1ccc(N(c2ccccc2)c2cc3c(o2)C2(c4ccccc4Oc4ccccc42)c2cc(N(c4ccccc4)c4ccccc4)oc2C32c3ccccc3Oc3ccccc32)cc1]

A specific preparation method is described below.

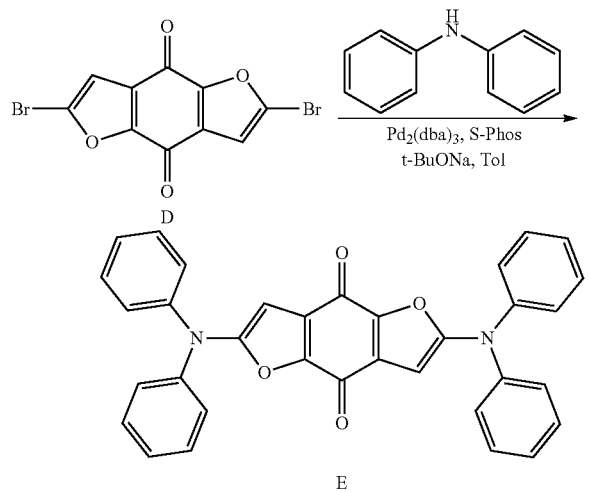

In a nitrogen atmosphere, raw materials: compound D (5 mmol), diphenylamine (11 mmol), t-BuONa (12.5 mmol), $Pd_2(dba)_3$ (0.25 mmol) and S-Phos (0.75 mmol) were sequentially added to 200 mL of Tol, deoxygenated for 10 min, raised to 110° C. and reacted for 24 h. After the reaction was finished, the reaction solution was cooled and suction filtered, the filtrate was collected, added with water and extracted with dichloromethane to separate liquid layers, and the organic phases were collected, dried with anhydrous sodium sulfate, and suction filtered. The filtrate was collected, the solvent was removed through rotary evaporation, and the reaction product was purified through column chromatography to obtain an intermediate E (with a yield of 79%).

LC-MS: m/z: a calculated value: $C_{34}H_{22}N_2O_4$: 522.55, a measured value: 522.10.

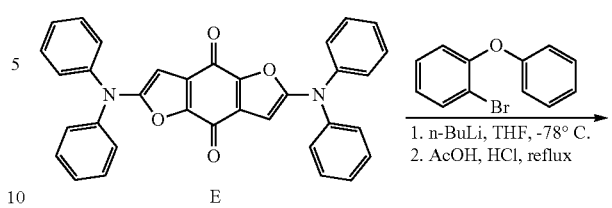

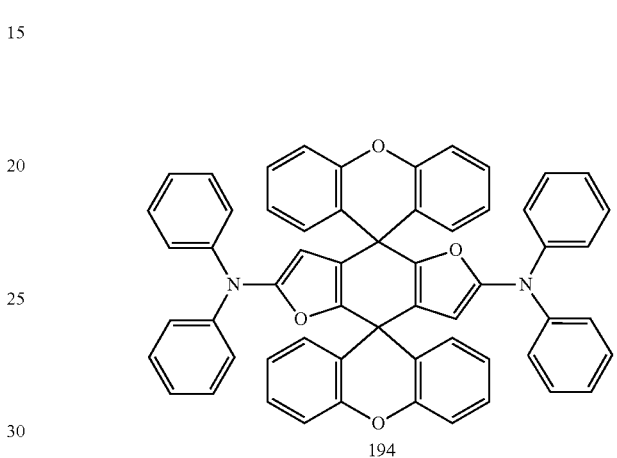

In a nitrogen atmosphere, a reactant 2-bromodiphenyl ether (2.2 mmol) was added to 100 mL of anhydrous THF and stirred at −78° C. for 10 min. After the reaction solution was cooled, 1.6M n-BuLi (2.5 mmol) was added dropwise. After the dropwise addition, the reaction was continued at −78° C. for 2 h. The intermediate E (1 mmol) was dissolved in a solution of anhydrous THF (50 mL), and then added dropwise to a low-temperature reaction solution with an injector. After the dropwise addition, the reaction was continued at a low temperature for 1 h and then raised to room temperature for a reaction of 5 h. After the reaction was finished, a small amount of water was added to quench the reaction, water and dichloromethane were added for extraction, and the organic phases were collected, dried with anhydrous sodium sulfate and suction filtered. The filtrate was collected, and the solvent was removed through rotary evaporation to obtain the crude product.

(3) Under a nitrogen condition, the above crude product was added to 80 mL of acetic acid, stirred and heated, reacted at 120° C. for 2 h, added with 5 mL of hydrochloric acid, and heated at this temperature for 12 h. After the reaction was finished, the reaction solution was cooled and extracted, the organic phases were collected, and the solvent was removed through rotary evaporation. The reaction product was purified through column chromatography to obtain the compound 194 (with a yield of 67%).

LC-MS: m/z: a calculated value: $C_{58}H_{38}N_2O_4$: 826.93, a measured value: 826.56.

Elemental analysis result of the compound: a calculated value: $C_{58}H_{38}N_2O_4$ (%): C 84.24, H 4.63, N 3.39; a test value: C 84.23, H 4.65, N 3.38.

Preparation Example 8

This preparation example provides a compound 470

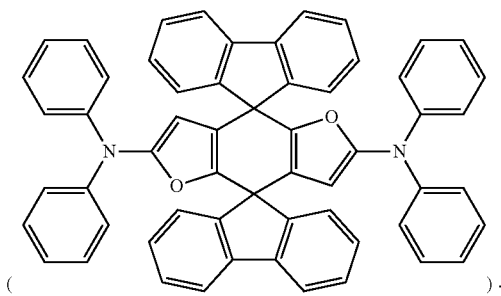 [SMILES: c1ccc(N(c2ccccc2)c2cc3c(o2)C2(c4ccccc4-c4ccccc42)c2cc(N(c4ccccc4)c4ccccc4)oc2C32c3ccccc3-c3ccccc32)cc1]

( ).

A specific preparation method is described below.

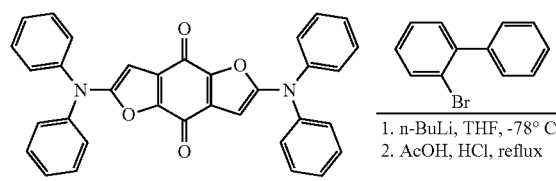

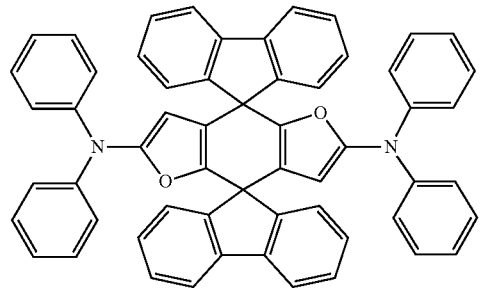

470

The preparation method of the organic compound 470 only differed from that of Preparation Example 7 in that 2-bromodiphenyl ether

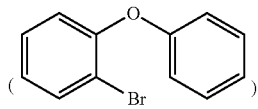 [SMILES: Brc1ccccc1Oc1ccccc1]

in step (2) in Preparation Example 7 was replaced with an equal molar amount of 2-bromodiphenyl

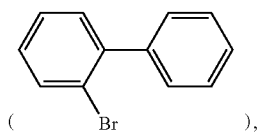

and other raw materials, reaction steps and reaction conditions were the same as those in Example 7, and the target product 8 was finally obtained (with a yield of 70%).

LC-MS: m/z: a calculated value: $C_{58}H_{38}N_2O_2$: 794.93, a measured value: 794.65.

Elemental analysis result of the compound: a calculated value: $C_{58}H_{38}N_2O_2$ (%): C 87.63, H 4.82, N 3.52; a test value: C 87.65, H 4.81, N 3.51.

Preparation Example 9

This preparation example provides a compound 464

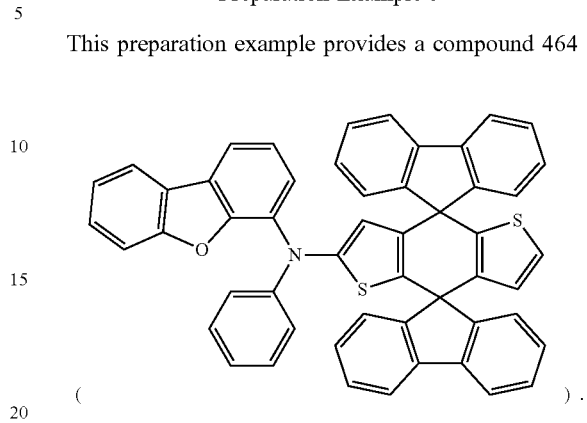

( ).

A specific preparation method is described below.

(1)

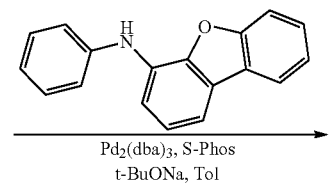

F

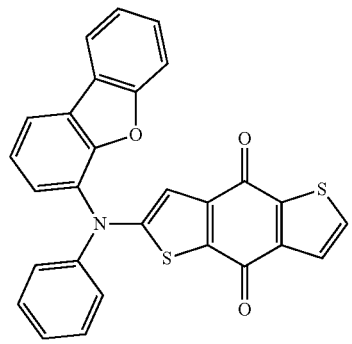

G

In a nitrogen atmosphere, raw materials: a compound F (5 mmol), dibenzofuran-4-yl-aniline (5.5 mmol), t-BuONa (12.5 mmol), tris(dibenzalacetone)dipalladium ($Pd_2(dba)_3$) (0.25 mmol) and 2-dicyclohexylphosphine-2',6'-dimethoxybiphenyl (S-Phos) (0.75 mmol) were sequentially added to 200 mL of anhydrous toluene (Tol), deoxygenated for 10 min, raised to 110° C. and reacted for 24 h. After the reaction was finished, the reaction solution was cooled and suction filtered, the filtrate was collected, added with water and extracted with dichloromethane to separate liquid layers, and the organic phases were collected, dried with anhydrous sodium sulfate, and suction filtered. The filtrate was collected, the solvent was removed through rotary evaporation, and the reaction product was purified through column chromatography to obtain an intermediate G (with a yield of 83%).

LC-MS: m/z: a calculated value: $C_{28}H_{15}NO_3S_2$: 477.55, a measured value: 477.19.

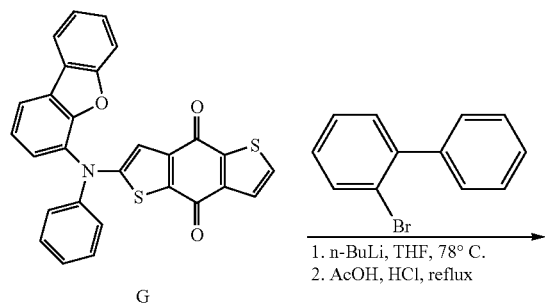

(2)

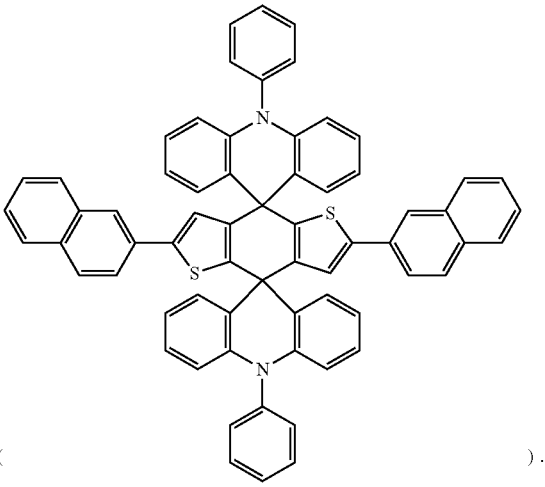 [SMILES: c1ccc(N2c3ccccc3C3(c4ccccc42)c2cc(-c4ccc5ccccc5c4)sc2C2(c4ccccc4N(c4ccccc4)c4ccccc42)c2cc(-c4ccc5ccccc5c4)sc23)cc1]

464

In a nitrogen atmosphere, a reactant 2-bromodiphenyl (2.2 mmol) was added to 100 mL of anhydrous THF and stirred at −78° C. for 10 min. After the reaction solution was cooled, 1.6M n-BuLi (2.5 mmol) was added dropwise. After the dropwise addition, the reaction was continued at −78 °C for 2 h. The intermediate G (1 mmol) was dissolved in a solution of anhydrous THF (50 mL), and then added dropwise to a low-temperature reaction solution with an injector. After the dropwise addition, the reaction was continued at a low temperature for 1 h and then raised to room temperature for a reaction of 5 h. After the reaction was finished, a small amount of water was added to quench the reaction, water and dichloromethane were added for extraction, and the organic phases were collected, dried with anhydrous sodium sulfate and suction filtered. The filtrate was collected, and the solvent was removed through rotary evaporation to obtain the crude product.

(3) Under a nitrogen condition, the above crude product was added to 80 mL of acetic acid, stirred and heated, reacted at 120° C. for 2 h, added with 5 mL of hydrochloric acid, and heated at this temperature for 12 h. After the reaction was finished, the reaction solution was cooled and extracted, the organic phases were collected, and the solvent was removed through rotary evaporation. The reaction product was purified through column chromatography to obtain the compound 464 (with a yield of 70%).

LC-MS: m/z: a calculated value: $C_{52}H_{31}NOS_2$: 749.94, a measured value: 749.69.

Elemental analysis result of the compound: a calculated value: $C_{52}H_{31}NOS_2$ (%): C 83.28, H 4.17, N 1.87; a test value: C 83.29, H 4.18, N 1.86.

Preparation Example 10

This preparation example provides a compound 7

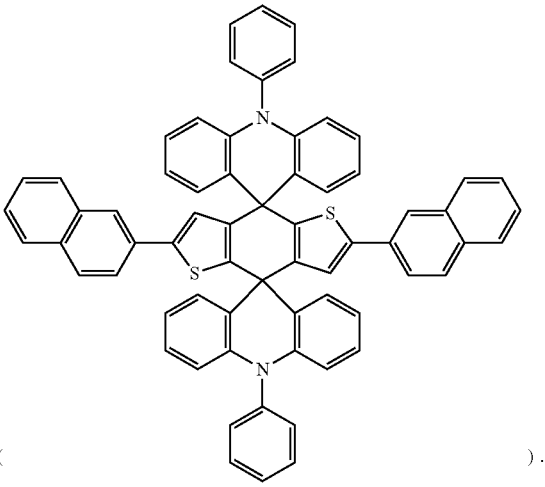 [SMILES: c1ccc(N2c3ccccc3C3(c4ccccc42)c2cc(-c4ccc5ccccc5c4)sc2C2(c4ccccc4N(c4ccccc4)c4ccccc42)c2cc(-c4ccc5ccccc5c4)sc23)cc1]

A specific preparation method is described below.

(1)

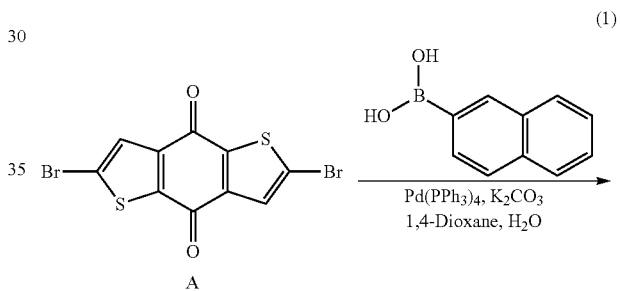

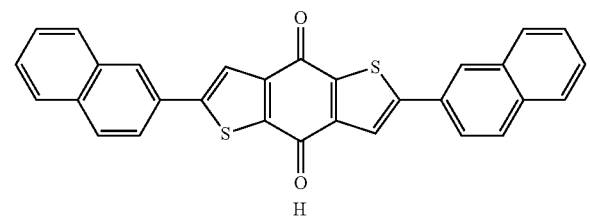

In a nitrogen atmosphere, 100 mL of 1,4-dioxane solvent was added to a 250 mL reaction flask, and a $K_2CO_3$ solution (2.5 mmol), an intermediate reactant A (1 mmol), 2-naphthaleneboric acid (2.2 mmol) and $Pd(PPh_3)_4$ (0.05 mmol) were sequentially added. The mixture was raised to 100° C. and reacted overnight. After the reaction was finished, the reaction was cooled to room temperature, dichloromethane/$H_2O$ were added for extraction, and the collected organic phases were dried with anhydrous $Na_2SO_4$ and suction filtered. The filtrate was collected, the solvent was removed through rotary evaporation, and the reaction product was purified through column chromatography to obtain an intermediate H (with a yield of 85%).

LC-MS: m/z: a calculated value: $C_{30}H_{16}O_2S_2$: 472.58, a measured value: 472.26.

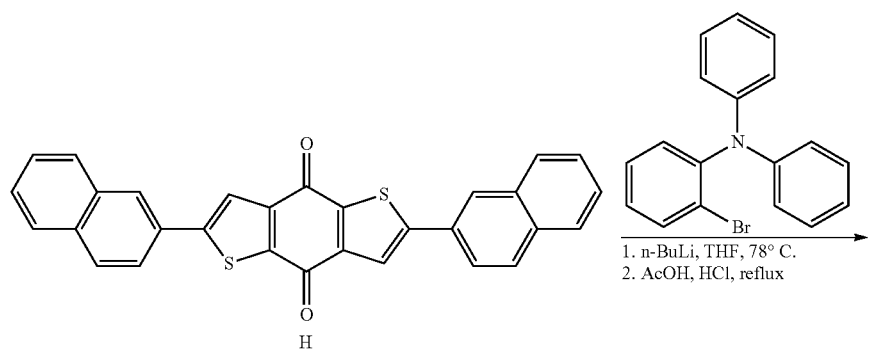

(2)

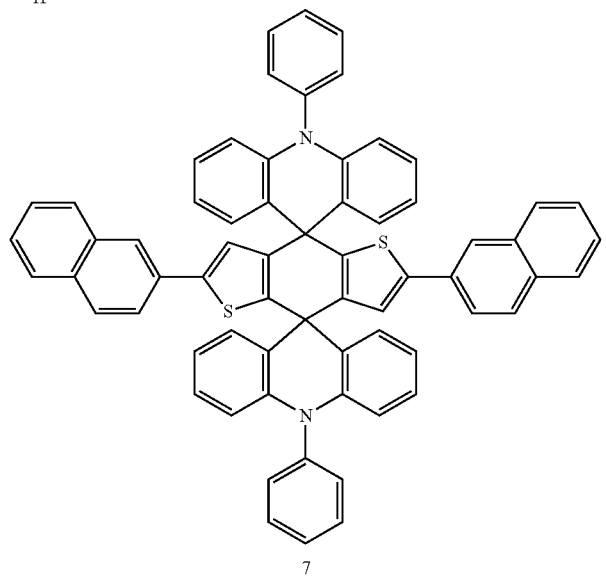

7

In a nitrogen atmosphere, a reactant 2-bromotriphenylamine (2.2 mmol) was added to 100 mL of anhydrous THF and stirred at −78° C. for 10 min. After the reaction solution was cooled, 1.6M n-BuLi (2.5 mmol) was added dropwise. After the dropwise addition, the reaction was continued at −78° C. for 2 h. The intermediate H (1 mmol) was dissolved in a solution of anhydrous THF (50 mL), and then added dropwise to a low-temperature reaction solution with an injector. After the dropwise addition, the reaction was continued at a low temperature for 1 h and then raised to room temperature for a reaction of 5 h. After the reaction was finished, a small amount of water was added to quench the reaction, water and dichloromethane were added for extraction, and the organic phases were collected, dried with anhydrous sodium sulfate and suction filtered. The filtrate was collected, and the solvent was removed through rotary evaporation to obtain the crude product.

(3) Under a nitrogen condition, the above crude product was added to 80 mL of acetic acid, stirred and heated, reacted at 120° ° C. for 2 h, added with 5 mL of hydrochloric acid, and heated at this temperature for 12 h. After the reaction was finished, the reaction solution was cooled and extracted, the organic phases were collected, and the solvent was removed through rotary evaporation. The reaction product was purified through column chromatography to obtain the compound 7 (with a yield of 68%).

LC-MS: m/z: a calculated value: $C_{66}H_{42}N_2S_2$: 927.18, a measured value: 926.81.

Elemental analysis result of the compound: a calculated value: $C_{66}H_{42}N_2S_2$ (%): C 85.50, H 4.57, N 3.02; a test value: C 85.52, H 4.58, N 3.01.

Preparation Example 11

This preparation example provides a compound 373

( 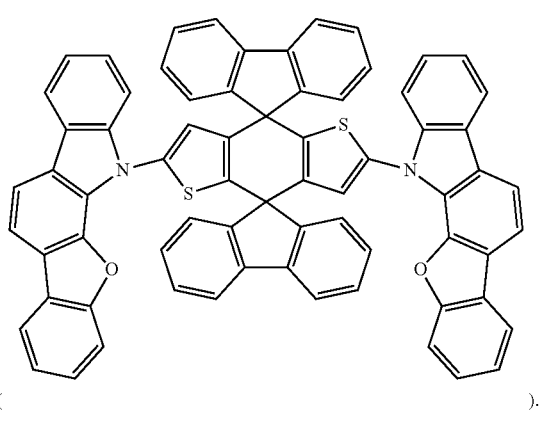 [SMILES: c1ccc2c(c1)-c1ccccc1C21c2cc(-n3c4ccccc4c4ccc5c6ccccc6oc5c43)sc2C2(c3ccccc3-c3ccccc32)c2cc(-n3c4ccccc4c4ccc5c6ccccc6oc5c43)sc21] ).

A specific preparation method is described below.

(1)

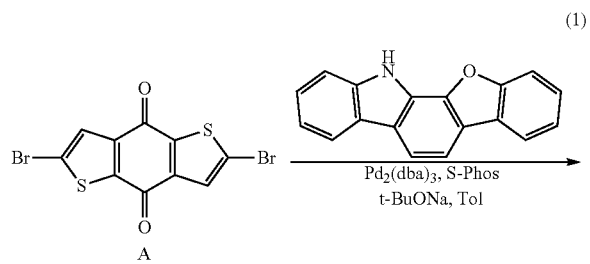

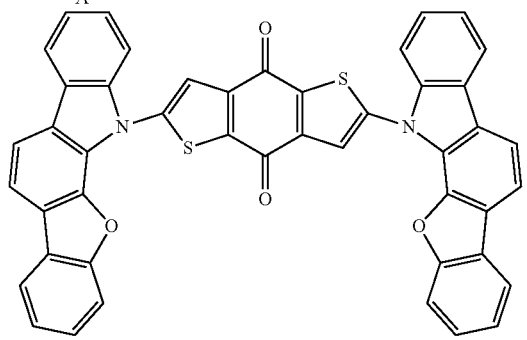

An intermediate I was synthesized: a preparation method of the intermediate I only differed from that of the intermediate B in that diphenylamine

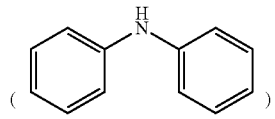 [SMILES: c1ccc(Nc2ccccc2)cc1]

in step (1) of Preparation Example 1 was replaced with an equal molar amount of 12H-11-oxa-12-azaindeno[2,1-a]fluorene ( ), and other raw materials, reaction steps and reaction conditions were the same as those in Preparation Example 1, and the intermediate product I was finally obtained (with a yield of 65%).

LC-MS: m/z: a calculated value: $C_{46}H_{22}N_2O_4S_2$: 730.81, a measured value: 730.46.

(2)

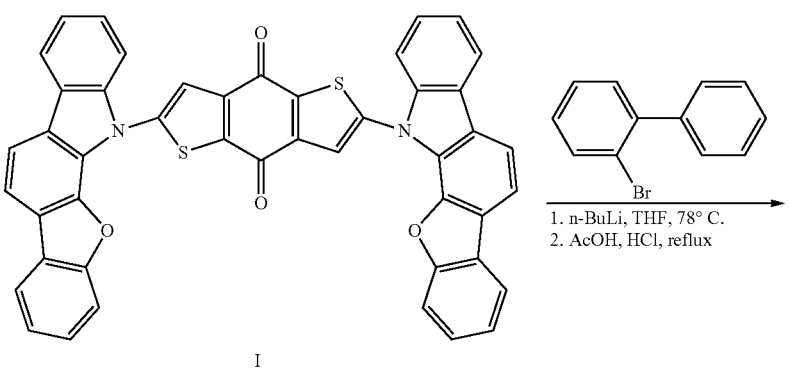

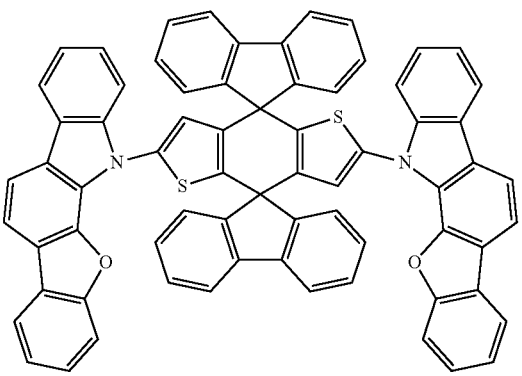

373

The compound 373 was synthesized: the preparation method of the organic compound 373 only differed from that in Preparation Example 6 in that the intermediate C in step (2) of Preparation Example 6 was replaced with an equal molar amount of intermediate I

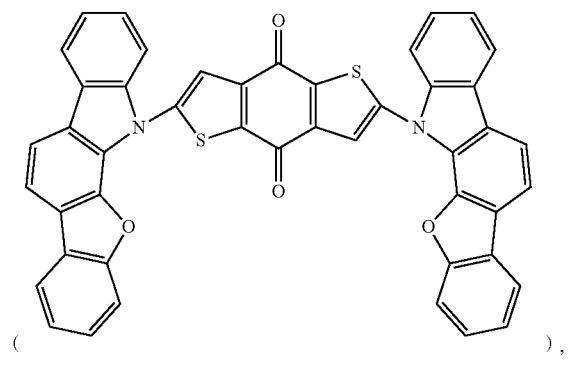 [SMILES: O=C1c2cc(-n3c4ccccc4c4ccc5c6ccccc6oc5c43)sc2C(=O)c2cc(-n3c4ccccc4c4ccc5c6ccccc6oc5c43)sc21]

and other raw materials, reaction steps and reaction conditions were the same as those in steps (2) and (3) in Preparation Example 6, and the compound 373 was finally obtained (with a yield of 65%).

LC-MS: m/z: a calculated value: $C_{70}H_{38}N_2O_2S_2$: 1003.19, a measured value: 1002.81.

Elemental analysis result of the compound: a calculated value: $C_{70}H_{38}N_2O_2S_2$ (%): C 83.81, H 3.82, N 2.79; a test value: C 83.80, H 3.81, N 2.81.

Preparation Example 12

This preparation example provides a compound 359

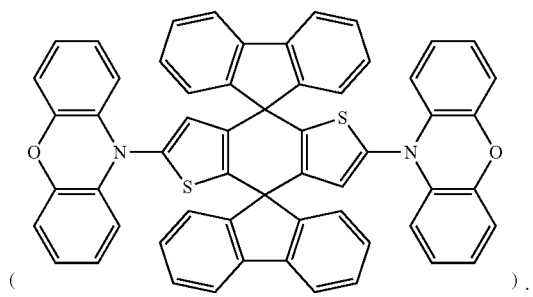 [SMILES: c1ccc2c(c1)Oc1ccccc1N2c1cc2c(s1)C1(c3ccccc3-c3ccccc31)c1cc(N3c4ccccc4Oc4ccccc43)sc1C21c2ccccc2-c2ccccc21]

A specific preparation method is described below.

(1)

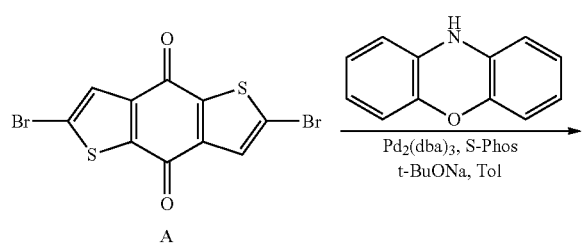

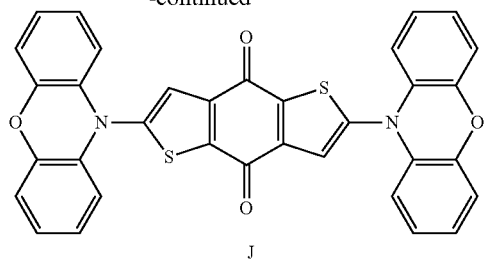

J

An intermediate J was synthesized: a preparation method of the intermediate J only differed from that of the intermediate B in that diphenylamine

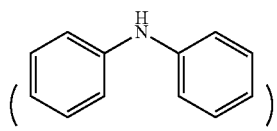

in step (1) in Preparation Example 1 was replaced with an equal molar amount of phenoxazine

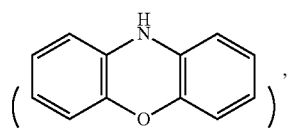

and other raw materials, reaction steps and reaction conditions were the same as those in step (1) in Example 1, and the intermediate product J was finally obtained (with a yield of 69%).

LC-MS: m/z: a calculated value: $C_{34}H_{18}N_2O_4S_2$: 582.65, a measured value: 582.19.

(2)

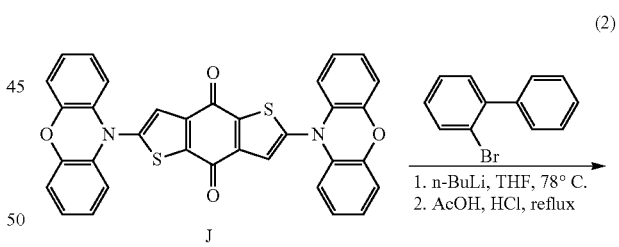

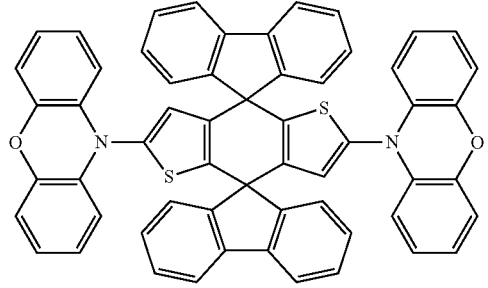

359

The compound 359 was synthesized: the preparation method of the organic compound 359 only differed from that of Preparation Example 6 in that the intermediate C in step (2) in Preparation Example 6 was replaced with an equal molar amount of intermediate J

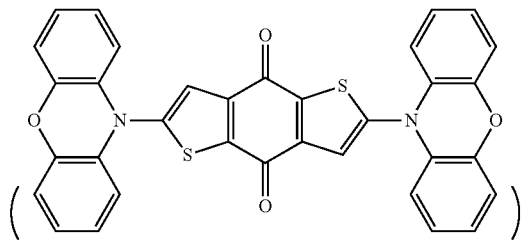

and other raw materials, reaction steps and reaction conditions were the same as those in steps (2) and (3) in Preparation Example 6, and the target product 12 was finally obtained (with a yield of 60%).

LC-MS: m/z: a calculated value: $C_{58}H_{34}N_2O_2S_2$: 855.03, a measured value: 854.63.

Elemental analysis result of the compound: a calculated value: $C_{58}H_{34}N_2O_2S_2$ (%): C 81.47, H 4.01, N 3.28; a test value: C 81.46, H 3.99, N 3.29.

Preparation Example 13

This preparation example provides a compound 330

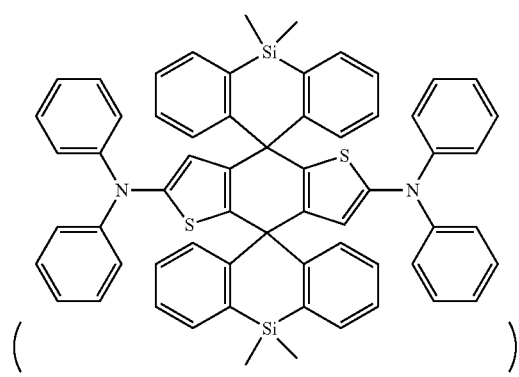

A specific preparation method is described below.

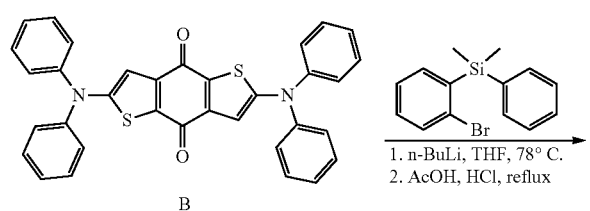

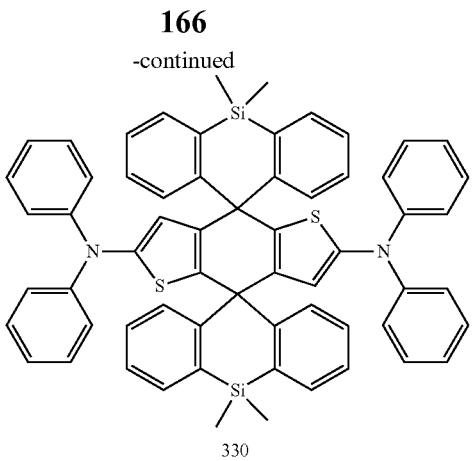

The preparation method of the organic compound 330 only differed from that in Preparation Example 1 in that 2-bromodiphenyl ether

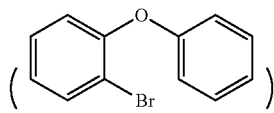

in step (2) in Preparation Example 1 was replaced with an equal molar amount of (2-bromo-phenyl)-dimethyl-phenyl-silane

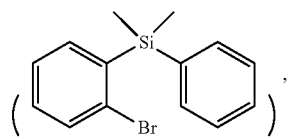

and other raw materials, reaction steps and reaction conditions were the same as those in Preparation Example 1, and the compound 330 was finally obtained (with a yield of 58%).

LC-MS: m/z: a calculated value: $C_{62}H_{50}N_2S_2Si_2$: 943.37, a measured value: 943.01.

Elemental analysis result of the compound: a calculated value: $C_{62}H_{50}N_2S_2Si_2$ (%): C 78.94, H 5.34, N 2.97; a test value: C 78.95, H 5.36, N 2.96.

Simulated calculations of energy levels of compounds

By use of a density functional theory (DFT), the distribution of molecular frontier orbitals, HOMO and LUMO, was optimized and calculated for the organic compounds provided 5 in the examples of the present disclosure and a compound spiro-TPD

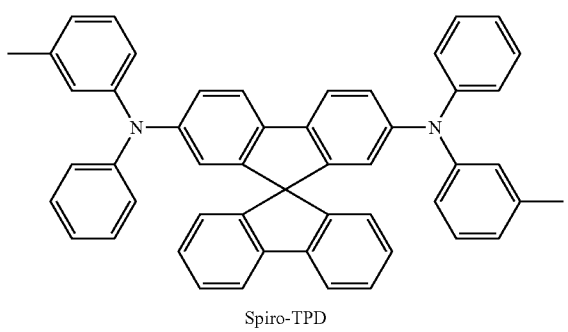

Spiro-TPD using a Guassian 09 package (Guassian Inc.) at a B3LYP/ 6-31G(d) calculation level. Meanwhile, based on a time-dependent density functional theory (TDDFT), a lowest singlet energy level $S_1$ and a lowest triplet energy level $T_1$ of molecules of each compound were simulated and calculated. Results are shown in Table 1.

TABLE 1

| Compound | HOMO (eV) | LUMO (eV) | $E_{S1}$ (eV) | $E_{T1}$ (eV) |
|---|---|---|---|---|
| Compound 134 | −4.89 | −0.89 | 3.67 | 2.86 |
| Compound 14 | −4.83 | −0.72 | 3.66 | 2.85 |
| Compound 302 | −4.92 | −1.02 | 3.65 | 2.83 |
| Compound 167 | −4.97 | −1.00 | 3.45 | 2.82 |
| Compound 287 | −4.96 | −0.98 | 3.47 | 2.83 |
| Compound 380 | −4.99 | −1.01 | 3.43 | 2.82 |
| Compound 194 | −4.90 | −0.92 | 3.65 | 2.85 |
| Compound 470 | −4.92 | −0.98 | 3.64 | 2.83 |
| Compound 464 | −5.00 | −0.92 | 3.57 | 2.87 |
| Compound 7 | −4.99 | −0.89 | 3.64 | 2.86 |
| Compound 373 | −4.98 | −0.83 | 3.68 | 2.90 |
| Compound 359 | −4.93 | −0.91 | 3.60 | 2.88 |
| Compound 330 | −4.94 | −1.03 | 3.64 | 2.85 |
| Spiro-TPD | −4.56 | −0.85 | 3.24 | 2.50 |

As can be seen from Table 1, all the compounds provided by the present disclosure have appropriate HOMO energy levels (−4.80 to −5.05 eV) and better match an adjacent layer, which helps the transport of holes, reduces a hole injection barrier, and thereby reduces a voltage of element; the compounds have relatively shallow LUMO energy levels (>−1.05 eV), which can effectively block electrons; the compounds have relatively high triplet energy levels ($E_{T1}$>2.8 eV), which can effectively block excitons going beyond a light-emitting layer, confine the excitons in the light-emitting layer, improve an exciton utilization rate, thereby ensuring that the element has relatively high light-emitting efficiency. The compounds provided by the present disclosure each has a spiro ring structure, can reduce the stacking of molecules and avoid the crystallization of the molecules, and have excellent thermal stability and thin film stability, so that the compounds are more stably applied in the element and help to improve a lifetime of the element.

The following are several examples of applications of the organic compounds of the present disclosure in OLED elements.

Application Example 1

This application example provides an OLED element, whose structure is shown in FIG. 1. The OLED element includes a substrate 1, an anode 2, a hole injection layer 3, a first hole transport layer 4, a second hole transport layer 5, a light-emitting layer 6, a hole blocking layer 7, an electron transport layer 8, an electron injection layer and a cathode 10 which are stacked in sequence. An arrow in FIG. 1 represents a light-outgoing direction of the element.

The OLED element was prepared by specific steps described below.

(1) A glass substrate 1 with an indium tin oxide (ITO) anode 2 (which has a thickness of 100 nm) was cut to give a size of 50 mm×50 mm×0.7 mm, sonicated in isopropyl alcohol and deionized water for 30 minutes separately, and cleaned under ozone for 10 minutes. The cleaned glass substrate was installed onto a vacuum deposition apparatus.

(2) A material of the hole injection layer, HAT-CN, was deposited by means of vacuum evaporation on the ITO anode 2 as the hole injection layer 3 with a thickness of 10 nm.

(3) A hole transport material, compound b: TAPC, was deposited by means of vacuum evaporation on the hole injection layer 3 as the first hole transport layer 4 with a thickness of 100 nm.

(4) A compound 134 provided in Preparation Example 1 was deposited by means of vacuum evaporation on the first hole transport layer 4 as the second hole transport layer 5 with a thickness of 10 nm.

(5) A light-emitting host material, compound c, and a doping material, compound d, were co-deposited by means of vacuum evaporation on the second hole transport layer 5 as the light-emitting layer 6 with a thickness of 30 nm, where a doping ratio was 3% (a mass ratio).

(6) Compound e, BCP, was deposited by means of vacuum evaporation on the light-emitting layer 6 as the hole blocking layer 7 with a thickness of 5 nm.

(7) Compound f and compound g, Liq, were deposited by means of vacuum evaporation on the hole blocking layer 7 as the electron transport layer 8 with a thickness of 30 nm, where a doping mass ratio was 1: 1.

(8) Compound h, LiF, was deposited by means of vacuum evaporation on the electron transport layer 8 as the electron injection layer 9 with a thickness of 5 nm.

(9) An aluminum electrode was deposited by means of vacuum evaporation on the electron injection layer 9 as the cathode 10 with a thickness of 100 nm.

The compounds used for preparing the OLED element were as follows:

compound a

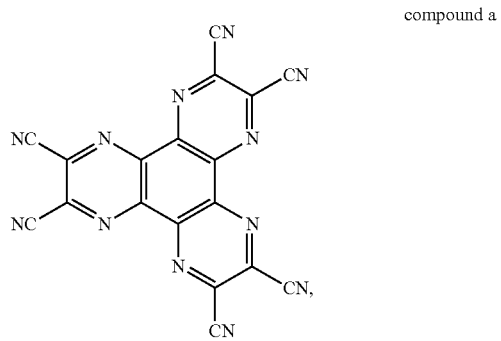

compound b

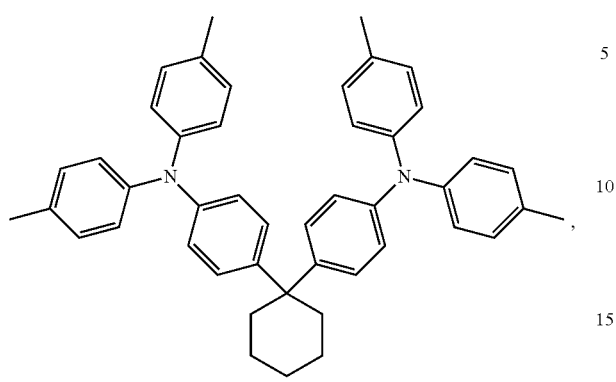

compound c

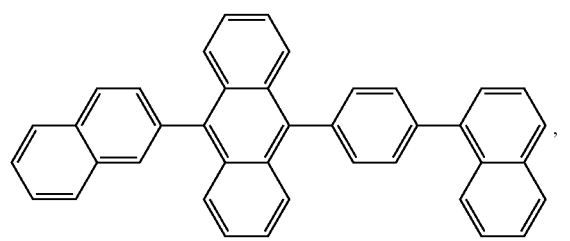

compound d

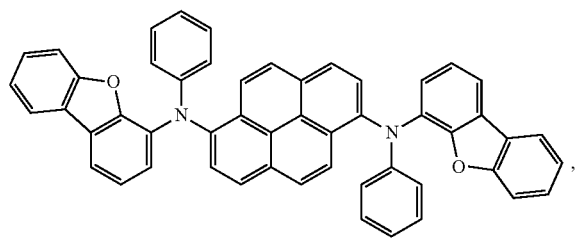

compound e

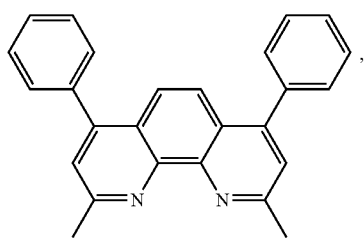

compound g

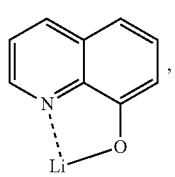

Compound f

Application Example 2

This application example provides an OLED element and differs from Application Example 1 in that the compound 134 in step (4) was replaced with compound 14 on the premise that other preparation steps were the same.

Application Example 3

This application example provides an OLED element and differs from Application Example 1 in that the compound 134 in step (4) was replaced with compound 302 on the premise that other preparation steps were the same.

Application Example 4

This application example provides an OLED element and differs from Application Example 1 in that the compound 134 in step (4) was replaced with compound 167 on the premise that other preparation steps were the same.

Application Example 5

This application example provides an OLED element and differs from Application Example 1 in that the compound 134 in step (4) was replaced with compound 287 on the premise that other preparation steps were the same.

Application Example 6

This application example provides an OLED element and differs from Application Example 1 in that the compound 134 in step (4) was replaced with compound 380 on the premise that other preparation steps were the same.

Application Example 7

This application example provides an OLED element and differs from Application Example 1 in that the compound 134 in step (4) was replaced with compound 194 on the premise that other preparation steps were the same.

Application Example 8

This application example provides an OLED element and differs from Application Example 1 in that the compound 134 in step (4) was replaced with compound 470 on the premise that other preparation steps were the same.

Application Example 9

This application example provides an OLED element and differs from Application Example 1 in that the compound 134 in step (4) was replaced with compound 464 on the premise that other preparation steps were the same.

Application Example 10

This application example provides an OLED element and differs from Application Example 1 in that the compound 134 in step (4) was replaced with compound 7 on the premise that other preparation steps were the same.

Application Example 11

This application example provides an OLED element and differs from Application Example 1 in that the compound 134 in step (4) was replaced with compound 373 on the premise that other preparation steps were the same.

Application Example 12

This application example provides an OLED element and differs from Application Example 1 in that the compound 134 in step (4) was replaced with compound 359 on the premise that other preparation steps were the same.

Application Example 13

This application example provides an OLED element and differs from Application Example 1 in that the compound 134 in step (4) was replaced with compound 330 on the premise that other preparation steps were the same.

Comparative Example 1

This comparative example provides an OLED element and differs from Application Example 1 in that the compound 134 was replaced with a compound spiro-TPD

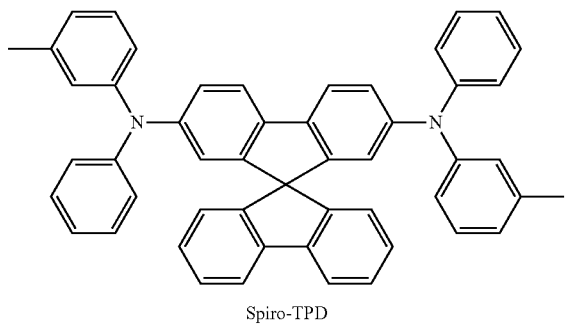

Spiro-TPD

Performance evaluation of OLED elements

A Keithley 2365A digital nanovoltmeter was used for testing currents of the OLED element at different voltages, and then the currents were divided by a light-emitting area to obtain current densities of the OLED element at different voltages. A Konicaminolta CS-2000 spectroradiometer was used for testing the brightness and radiant energy flux densities of the OLED element at different voltages. According to the current densities and brightness of the OLED element at different voltages, current efficiency CE/CIEy (cd/A) and a working voltage V at the same current density (10 mA/cm$^2$) were obtained. A lifetime LT95 (under a testing condition of 500 mA/cm$^2$) was obtained by measuring time when the brightness of the OLED element reached 95% of its initial brightness. Test data is shown in Table 2.

TABLE 2

| OLED Element | Second Hole Transport Layer | V (V) | CE/CIEy (cd/A) | Lifetime LT95 (h) |
|---|---|---|---|---|
| Application Example 1 | Compound 134 | 3.84 | 73 | 64 |
| Application Example 2 | Compound 14 | 3.83 | 74 | 65 |
| Application Example 3 | Compound 302 | 3.86 | 71 | 63 |
| Application Example 4 | Compound 167 | 3.82 | 74 | 67 |
| Application Example 5 | Compound 287 | 3.83 | 73 | 66 |
| Application Example 6 | Compound 380 | 3.81 | 75 | 69 |
| Application Example 7 | Compound 194 | 3.85 | 73 | 63 |
| Application Example 8 | Compound 470 | 3.84 | 72 | 64 |
| Application Example 9 | Compound 464 | 3.86 | 70 | 60 |
| Application Example 10 | Compound 7 | 3.89 | 68 | 65 |
| Application Example 11 | Compound 373 | 3.88 | 69 | 68 |
| Application Example 12 | Compound 359 | 3.87 | 71 | 66 |
| Application Example 13 | Compound 330 | 3.87 | 70 | 61 |
| Comparative Example 1 | Spiro-TPD | 3.98 | 60 | 56 |

As can be seen from Table 2, the OLED elements provided by the present disclosure have relatively low driving voltages, relatively high light-emitting efficiency, and relatively long lifetimes, where the working voltage is less than or equal to 3.9 V, the current efficiency CE/CIEy is greater than or equal to 68 cd/A, and the lifetime LT95 is greater than or equal to 60 h. Compared with that in Comparative Example 1, the OLED elements using the compounds of the present disclosure have reduced working voltages and improved efficiency and lifetimes because the compounds of the present disclosure have appropriate HOMO energy levels, better match an adjacent layer, and higher triplet energy levels (>2.8 eV), which can effectively transport holes to the light-emitting layer, effectively recombine holes and electrons into excitons, confine the excitons in the light-emitting layer, and effectively improve the efficiency of OLED elements. Meanwhile, the structures of the compounds of the present disclosure effectively reduce the stacking of molecules, which ensures that the compounds have excellent thermal stability and thin film stability, so that the OLED elements work more stably and have improved lifetimes.

Another application example of the present disclosure provides a display device including the display panel described above.

Figure 2:
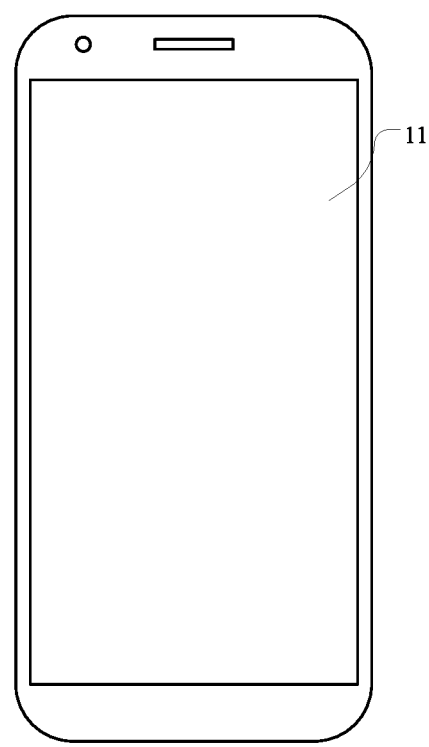
FIG. 2 is a schematic diagram of a display device according to an application example of the present disclosure.

In the present disclosure, the OLED element may be applied in the display device. The display device may be a display of a mobile phone, computer, television, smart watch, smart car, and VR or AR helmet, and displays of various smart apparatuses, etc. FIG. 2 is a schematic diagram of a display device according to an application example of the present disclosure, where 11 is the display of the mobile phone.

The invention claimed is:

1. A compound, having a structure represented by Formula V:

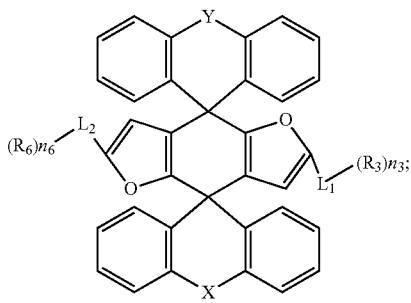

formula V $R_3$ and $R_6$ are each independently selected from

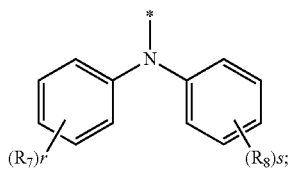

$R_7$ and $R_8$ are each independently selected from any one of C1 to C20 alkyl, C1 to C20 alkoxy, C1 to C20 alkylthio or following groups:

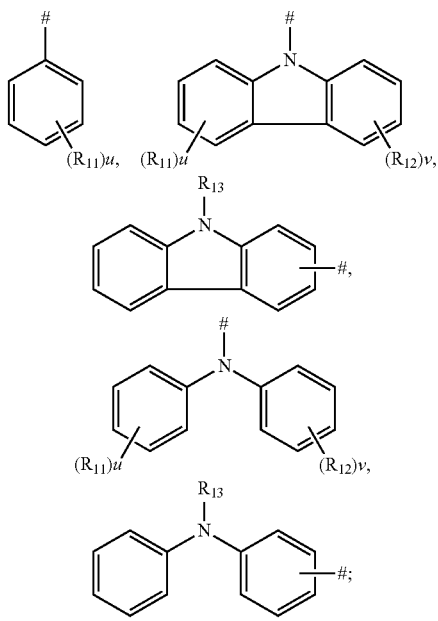

r and s are each independently 0, 1 or 2;
wherein $R_{11}$, $R_{12}$ and $R_{13}$ are each independently selected from any one of C to C20 alkyl, C1 to C20 alkoxy, C1 to C20 alkylthio or phenyl;
u and v are each independently 0, 1 or 2;
* and # each represent a position where groups are joined;
$n_3$ and $n_6$ are each independently an integer from 0 to 4, and $n_3$ and $n_6$ are not 0 at the same time;

$L_1$ and $L_2$ are each independently selected from a single bond; and

X and Y are each independently selected from any one of a single bond or an O atom.

2. The compound according to claim 1, wherein $L_1$ and $L_2$ are each independently a single bond,

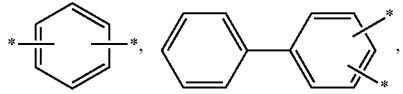

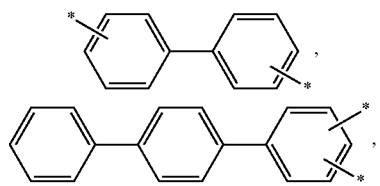

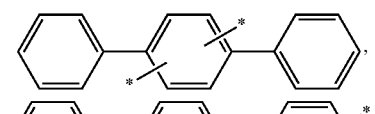

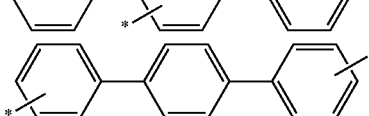

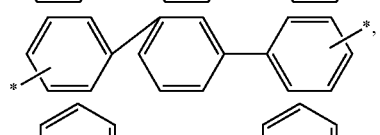

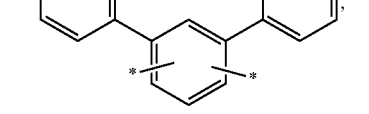

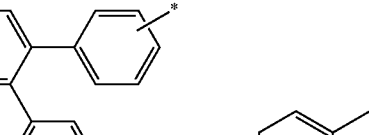

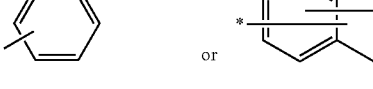

wherein * represents a position where groups are joined.

3. The compound according to claim 1, wherein $n_3$ is equal to no, and $R_3$ and $R_6$ are same groups.

4. The compound according to claim 1, wherein $n_4$ and $n_5$ are each independently an integer from 1 to 4, and $R_4$ and $R_8$ are each independently selected from any one of C1 to C5 alkyl, C1 to C5 alkoxy, C1 to C5 alkylthio or phenyl.

5. The compound according to claim 1, wherein X is the same as Y.

6. The compound according to claim 1, wherein the compound is selected from any one of following compounds:

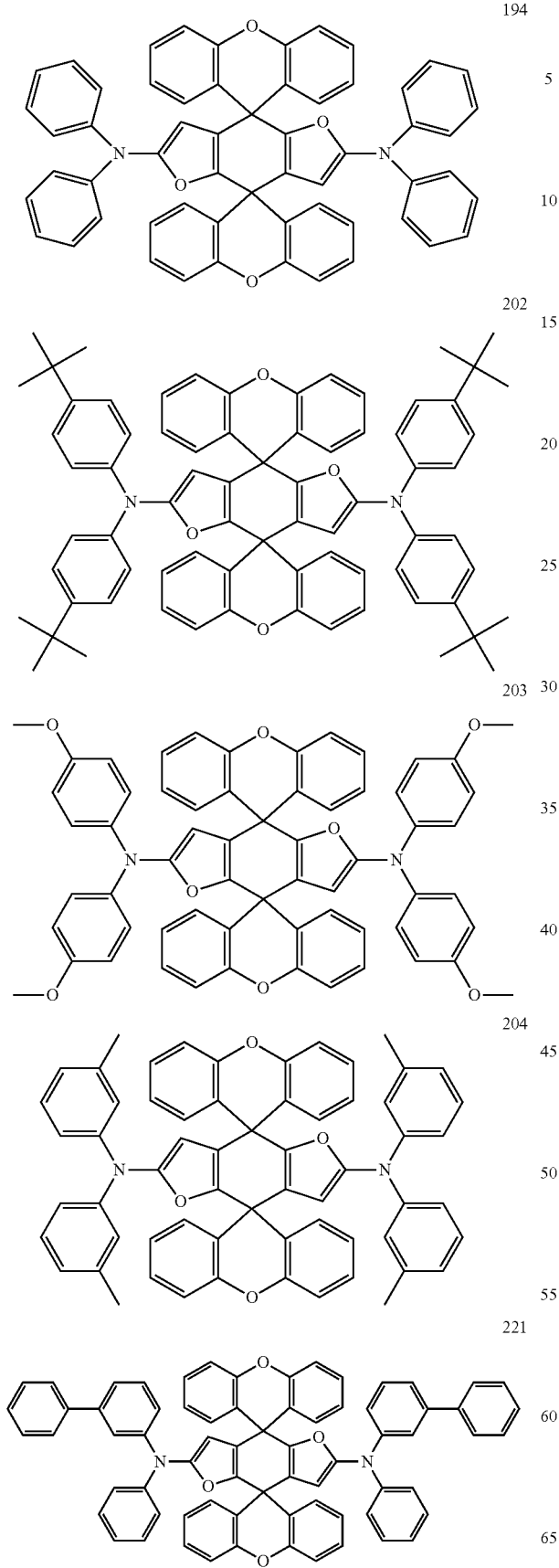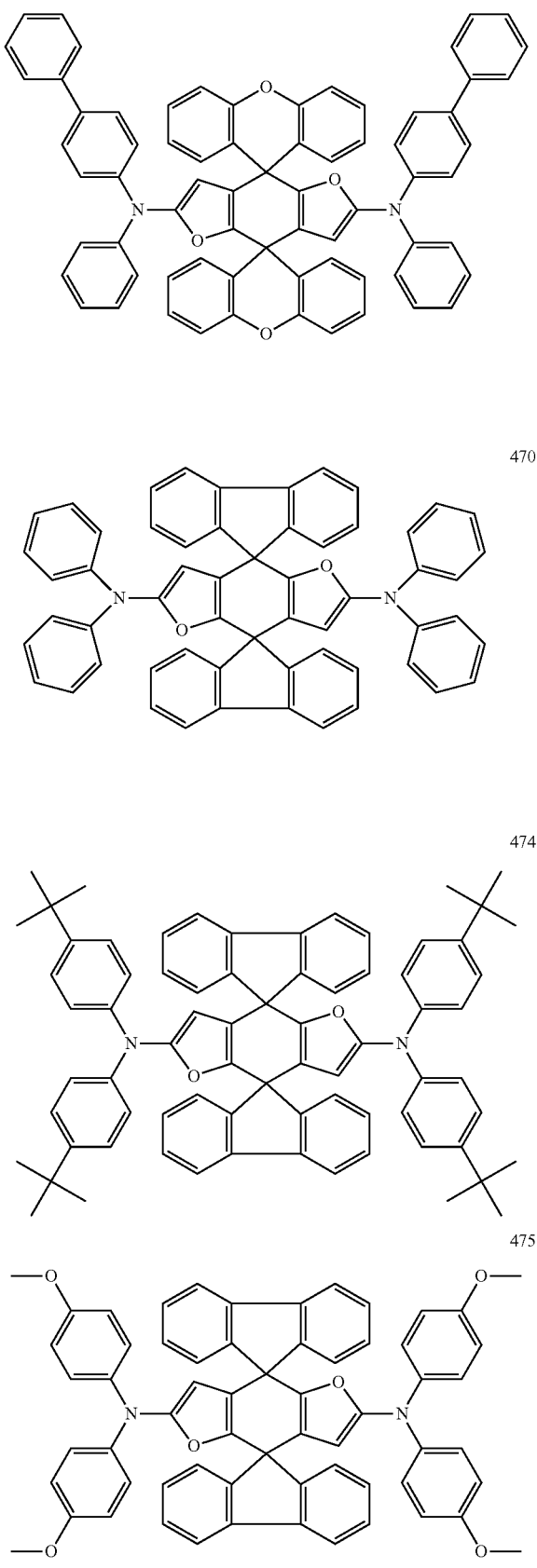

476

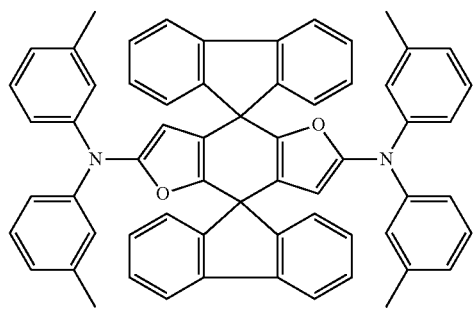

482

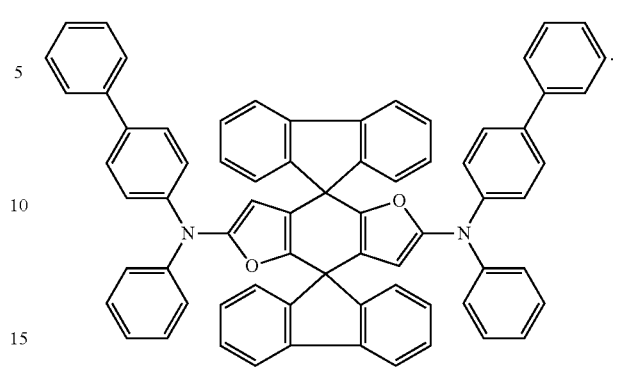

481

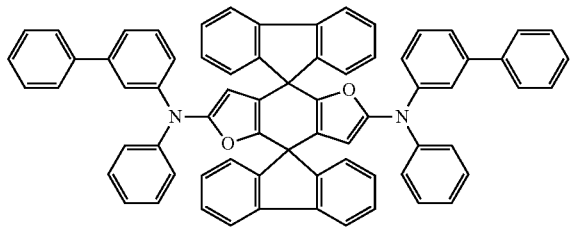

7. An organic light-emitting element, comprising an anode, a cathode and an organic thin film layer disposed between the anode and the cathode: wherein the organic thin film layer comprises a light-emitting layer, and further comprises any one or a combination of at least two of a hole transport layer, an electron blocking layer and an auxiliary light-emitting layer:
wherein at least one of the hole transport layer, the electron blocking layer and the auxiliary light-emitting layer contains at least one of the compounds according to claim 1.

8. The organic light-emitting element according to claim 7, wherein the organic thin film layer further comprises any one or a combination of at least two of a hole injection layer, a hole blocking layer, an electron transport layer and an electron injection layer.

9. A display panel, comprising the organic light-emitting element according to claim 7, the display panel can be used in a display device.

\* \* \* \* \*